US006468759B1

(12) United States Patent
Charych

(10) Patent No.: US 6,468,759 B1
(45) Date of Patent: *Oct. 22, 2002

(54) DIRECT COLORIMETRIC DETECTION OF BIOCATALYSTS

(75) Inventor: Deborah Charych, Albany, CA (US)

(73) Assignee: Regents of the University of California, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/033,557

(22) Filed: Mar. 2, 1998

Related U.S. Application Data

(60) Provisional application No. 60/039,749, filed on Mar. 3, 1997.

(51) Int. Cl.⁷ .................... G01N 33/573; G01N 33/53; G01N 33/543; G01N 33/544; G01N 33/545
(52) U.S. Cl. .................. 435/7.4; 435/7.1; 435/7.72; 435/183; 436/518; 436/528; 436/531; 436/535
(58) Field of Search ................ 435/7.1, 7.4, 7.72, 435/183, 805, 963, 969; 436/37, 71, 829, 501, 518, 523, 531, 529, 528, 532, 535

(56) References Cited

U.S. PATENT DOCUMENTS

| | | | | |
|---|---|---|---|---|
| 4,859,538 A | | 8/1989 | Ribi | 428/474.4 |
| 5,001,048 A | * | 3/1991 | Taylor et al. | 435/4 |
| 5,156,810 A | * | 10/1992 | Ribi et al. | 422/82.01 |
| 5,192,507 A | * | 3/1993 | Taylor et al. | 422/68.1 |
| 5,268,305 A | * | 12/1993 | Ribi et al. | 436/501 |
| 5,366,881 A | * | 11/1994 | Singh et al. | 435/177 |
| 5,415,999 A | | 5/1995 | Saul et al. | 435/7.9 |
| 5,427,915 A | | 6/1995 | Ribi et al. | 435/7.92 |
| 5,480,582 A | | 1/1996 | Pope | 252/301.4 |
| 5,491,097 A | | 2/1996 | Ribi et al. | 436/518 |
| 5,521,101 A | | 5/1996 | Saini et al | 456/518 |
| 5,571,568 A | | 11/1996 | Ribi et al. | 427/487 |
| 5,618,735 A | * | 4/1997 | Saul et al. | 436/518 |
| 5,622,872 A | | 4/1997 | Ribi | 436/518 |
| 5,948,694 A | * | 9/1999 | Reber et al. | 436/518 |
| 6,001,556 A | * | 12/1999 | Charych et al. | 435/5 |

OTHER PUBLICATIONS

Bader et al. Angewandte Chemie 20: 91–92, 1981.*
Bennett et al. J. Mol. Biol. 140: 211–230, 1980.*
Bennett et al. PNAS 75: 4848–4852, 1980.*
Ahmed et al. J. Biochem. Tokyo 120: 1224–1231, Dec., abstract, 1996.*
Kaper et al. Clin. Microbiol. Rev. 8: 48–86, 1995.*
Arora et al. Biocheim. Biophys. Acta 884: 73–83, abstract, 1988.*
Arora et al. Can. J. Microbiol. 26: 243–249, abstract, 1980.*
Hachinohe et al. J. Gen. Virol. 70: 1287–1292, abstract, 1989.*
Cheng et al. Adv. Materials 9: 481–483, May, 1997.*
Charych et al. Chemtech. 26: 24–28, Sep. (E), 1996.*
Charych et al. MRS Bulletin 17: 61–64 (F), 1992.*
Radmacher et al. AIP Conference Proceedings 241: 144–153, 1991.*
The New Technology Profile, Ernest Orlando Lawrence Berkely National Laboratory, IB–915,965.*
Okada et al. Berkeley Scientific 1: 48–50, Spring, 1997.*
Taylor RF. In: Protein Immobilization Fundamentals and Applications, (Ed) RF Taylor, Marcel Dekker Inc., New York, Chapter 8, pp. 63–303, 1991.*
Kahn. Research News, Berkeley Lab., Dec. 10, 1996.*
Charych et al. Chem. Biol. 3: 113–120, Feb. (A), 1996.*
Charych et al. Science 261: 585–588 (B), 1993.*
Charych et al. Mater. Res. Soc. Symp. Proc. 292: 153–161 (C), 1993.*
Spevak et al. Advanced Materials 7: 85–89 (X), 1995.*
Balet et al. Biochim. Biophys. Res. Commun. 150: 561–567, 1988.*
Charych et al. Mater. Res. Soc. Symp. Proc. 330: 295–308 (D), 1994.*
Wilson et al. Langmuir 8: 2361–2364, 1992.*
Pan et al. Langmuir 13: 1365–1367, 1997.*
Jelinek et al. Chem. Biol. 5: 619–629, abstract, 1998.*
Okahata et al. Thin Solid Films 180: 65–72, 1989.*
Shibata et al. Thin Solid Films 179: 433–437, 1989.*
Spevak et al. J. Am. Chem. Soc. 115: 1146–1147 (Y), 1993.*
Pon et al. Biochim. Biophys. Acta 693: 461–465, 1982.*
Kondo et al. Biochim. Biophys. Acta 1124: 1–6, 1992.*
Reichert et al. J. Am. Chem. Soc. 117: 829–830, 1995.*
Dua et al. J. Biol. Chem. 270: 263–268, 1998.*
Mino et al. Langmuir 8: 594–598, 1992.*
Adlish et al., "Identification of a Putative Cell Receptor for Human Cytomegalovirus," *Virology* 176: 337–345 [1990].
Avnir, "Organic Chemistry within Ceramic Matrices: Doped Sol–Gel Materials," *Acc. Chem. Res.* 28: 328–334 [1995].
Bamford et al., "Membranes Exhibiting Molecular Recognition," *Adv. Mater.* 6:500–502 (1994).
Bamford et al., "Studies of a novel membrane for affinity separations," *J. Chromatography* 606:19–31 (1992).
Bayburt et al., "Continuous, Vesicle–Based Fluorimetric Assays of 14– and 85–kDa Phospholipases $A_2$," *Anal. Biochem.* 232:7–23 (1995).
Berman et al., "Total Alignment of Calcite at Acidic Polydiacetylene Films: Cooperativity at the Organic–Inorganic Interface," *Science* 259:515–518 (1995).

(List continued on next page.)

*Primary Examiner*—S. Devi
(74) *Attorney, Agent, or Firm*—Medlen & Carroll, LLP

(57) ABSTRACT

The present invention relates to methods and compositions for the direct detection of membrane conformational changes through the detection of color changes in biopolymeric materials. In particular, the present invention allows for the direct colorimetric detection of membrane modifying reactions and analytes responsible for such modifications and for the screening of reaction inhibitors.

16 Claims, 40 Drawing Sheets

OTHER PUBLICATIONS

Beswick and Pitt, "Optical Detection of Toxic Gases Using Fluorescent Porphyrin Langmuir–Blodgett Films," *J. Colloid Interface Sci.* 124: 146–155 [1988].

Bilewicz and Majda, "Monomolecular Langmuir–Blodgett Films at Electrodes. Formation of Passivating Monolayers and Incorporation of Electroactive Reagents," *Langmuir* 7: 2794–2802 [1991].

Binnig et al., "Atomic Resolution with Atomic Force Microscope," *Europhys. Lett.* 3: 1281–1286 [1987].

Binnig et al., "Atomic Force Microscope," *Phys. Rev. Lett.* 12:930–933 (1986).

Birdi, *Lipid and Biopolymer Monolayers at Liquid Interfaces*; Plenum Press, New York (1989).

Bomalaski and Clark, "Phospholipase $A_2$ and Arthritis," *Arthritis and Rheumatism* 36:190–198 (1992).

Camras et al., "Latanoprost, a Prostaglandin Analog, for Glaucoma Therapy," *Ophthalmology* 103:1916–1924 (1996).

Carel et al., "Structural Requirements for C3d, g/Epstein–Barr Virus Receptor (CR2/CD21) Ligand Binding, Internalization, and Viral Infection," *J. Biol. Chem.* 265: 12293–12299 [1990].

Carey, "Multivariate sensor arrays as industrial and environmental monitoring systems," *Trends Anal. Chem.* 13: 210–218 [1993].

Carey and Kowalski, "Monitoring a Dryer Operation Using an Array of Piezoelectic Crystals," *Anal. Chem.* 60: 541–544 [1988].

Casimir et al., "Preadipocyte differentiation blocked by prostaglandin stimulation of prostanoid $FP^2$ receptor in murine 3T3–L1 cells," *Differentiation* 60:203–210 (1996).

Cheng and Stevens, "Monolayer properties of monosialoganglioside in the mixed diacetylene lipid films on the air/water interface," *Chemistry and Physics of Lipids* 87:41–53 (1997).

Co et al., "Isolation and biochemical characterization of the mammalian reovirus type 3 cell–surface receptor," *Proc. Natl. Acad. Sci.* 82: 1494–1498 [1985].

Dave et al., "Sol–gel Encapsulation Methods for Biosensors," *Anal. Chem.* 66: 1120A–1127A [1994].

Day and Lando, "Morphology of Crystalline Diacetylene Monolayers Polymerized at the Gas–Water Interface," *Macromolecules* 13: 1478–1483 [1980].

Dennis and Wong, *Phospholipase $A_2$: Role and Function in Inflammation*; Plenum, New York (1990).

Dordick, *Biocatalysis for Industry*, Plenum Press (1991).

Downer et al., "Surface–bound biomembranes incorporating receptors: electrochemical and structural characterization," *Biosensor and Bioelect.* 7:429–440 (1992).

Ehnholm and Kuusi, "Preparation, Characterization, and Measurement of Hepatic Lipase," *Meth. Enzymol.* 129:716–738 (1986).

Ehlen et al., "Organic Clathrate–Forming Compounds as Highly Selective Sensor Coatings for the Gravimetric Detection of Solvent Vapors," *Angew. Chem. Int. Ed. Engl.* 32:110–112 (1993).

Eppstein et al., "Epidermal growth factor receptor occupancy inhibits vaccinia virus infection," *Nature* 318: 663–665 [1985].

Finegold and Martin, *Diagnostic Microbiology*, 6th Ed. (1982), CV Mosby St. Louis, pp 13–15.

Frankel et al., "Supramolecular Assemblies of Diacetylenic Aldonamides," *J. Am. Chem. Soc.* 116: 10057–10069 (1994).

Furuki and Pu, "Hybrid gas detector of squarylium dye Langmuir–Blodgett film deposited on a quartz oscillator," *Thin Solid Films* 210: 471–473 [1992].

Gaines, *Insoluble Monolayers at Liquid–Gas Interfaces*, pp. 291–300; Interscience Publishers, New York (1966).

Galiotis et el., "The Solid–State Polymerization and Physical Properties of Bis(ethyl Urethane) of 2.4–hexadiyne–1, 6–diol. II. Resonance Raman Spectroscopy," *J. Polym. Sci.* 21:2483–2494 (1983).

Gelb et al., "Inhibition of phospholipase $A_2$," *FASEB J.* 8:916 (1994).

Grainger et al., "Mixed monolayers of natural and polymeric phospholipids: structural characterization by physical and enzymatic methods," *Biochim. et Biophys. Acta* 1022:146–154 (1990).

Gronow, "Biosensors," *Trends Biochem. Sci.* 9: 336–340 [1984].

Jain et al., "Active–Site Directed Specific Competitive Inhibitors of Phospholipase $A_2$; Novel Transition–State Analogues," *Biochemistry* 30:10256–10268 (1991).

Kaner et al., "Fibroblast Growth Factor Receptor Is a Portal of Cellular Entry for Herpes Simplex Virus Type 1," *Science* 248: 1410–1413 [1990].

Karpe et al., "Thermal–desorption–gas chromatography–mass spectrometry–flame ionization detection–sniffer multi–coupling: A device for the determination of odorous volatile organic compounds in air," *J. Chromatography* A 708: 105–114 [1995].

Kepley et al., "Selective Surface Acoustic Wave–Based Organophosphonate Chemical Sensor Employing a Self–Assembled Composite Monolayer: A New Paradigm for Sensor Design," *Anal. Chem.* 64: 3191–3193 [1992].

Kini, *Venom Phospholipias $A_{2\ Enzymes}$*; Wiley, Chichester (1997).

Kolbe et al., "Atomic force microscopy imaging of T4 bacteriophages on silicon substrates," *Ultramicroscopy* 42–44: 1113–1117 [1992].

Krah et al., "Characterization of Octyl Glucoside–Solubilized Cell Membrane Receptors for Binding Measles Virus," *Virology* 172: 386–390 [1989].

Kuo et al., "Synthesis and Properties of Diacetylenic Glutamate Lipid Monomer and Polymer: Thermochromic Polydiacetylene Free–Standing Films," *Macromolecules* 23:3225–3230 (1990).

Lentz et al., "Is the Acetylcholine Receptors a Rabies Virus Receptor," *Science* 215: 182–184 [1982].

Levesque and Leclerc, "Ionochromic and Thermochromic Phenomena in a Regioregular Polythiophene Derivative Bearing Oligo(oxyethylene) Side Chains," *Chem. Mater.* 8:2843–2849 (1996).

Lin and Gelb, "Competitive Inhibition of Interfacial Catalysis by Phospholipase $A_2$: Differential Interaction of Inhibitors with the Vesicle Interface as a Controlling Factor of Inhibitor Potency," *J. Am. Chem. Soc.* 115:3932–3942 (1993).

Maoz and Sagiv, "On the Formation and Structure of Self––Assembling Monolayers," *J. Colloid Interface Sci.* 100:465–496 (1984).

Marlin et al., "A soluble form of intercellular adhesion molecule–1 inhibits rhinovirus infection," *Nature* 344: 70–72 [1990].

Marsella et al., "Ionoresistivity as a Highly Sensitive Sensory Probe: Investigations of Polythiophenes Functionalized with Calix[4]arene–Based Ion Receptors," *J. Am. Chem. Soc.* 117:9842–9848 (1995).

Mendelsohn et al., "Cellular Receptor for Poliovirus: Molecular Cloning, Nucleotide Sequence, and Expression of a New Member of the Immunoglobin Superfamily," *Cell* 56: 855–865 [1989].

Miller et al., "Synthesis conditions for encapsulating cytochrome c and catalase in $SiO_2$ sol–gel materials," *J. Non–Cryst. Solids* 202: 279–289 [1996].

Mirsky et al., "Capacitive sensor for lipolytic enzymes," *Thin Solid Films* 284:939–941 (1996).

Miyasaka et al., "Amperometric Glucose Sensor with Glucose Oxidase Immobilized on $SnO_2$ Electrode via a Monolayer of a Photoreactive Nitrophenylazide Derivative," *Chem. Lett.*, p. 627–630 (1990).

New, *Liposomes: A Practical Approach*, Oxford University Press, Oxford, pp 33–104 [1990].

New, *Liposomes: A Practical Approach*; IRL Press, Oxford (1989).

Okahata and Kunitake, "Formation of Stable Monolayer Membranes and Related Structurs in Dilute Aqueous Solution from Two–Headed Ammonium Amphiphiles," *J. Am. Chem. Soc.* 101: 5231–5234 [1979].

Ramirez and Jain, *Proteins: Structure Function and Genetics* 9:229 (1991).

Reynolds et al., "Analysis of Human Synovial Fluid Phospholipase A2 on Short Chain Phosphatidylcholine–Mixed Micelles: Development of a Spectrophotometric Assay Suitable for a Microtiterplate Reader," *Anal. Biochem.* 204:190–197 (1992).

Rhodes et al., "Structure of Polymerizable Lipid Bilayers. 6. Bilayer Structure of Three Polymerizable Diacetylenic Glutamate Lipids," *Langmuir* 10:267–275 (1994).

Roberts, *Langmuir–Blodgett Films*, Plenum, New York, [1990].

Rose–Pehrsson et al., "Detection of Hazardous Vapors Including Mixtures Using Recognition Analysis of Responses from Surface Acoustic Wave Devices," *Anal. Chem.* 60: 2801–2811 [1988].

Rosoff, *Vesicles*; Marcel Dekker Inc., New York (1996).

Ruff et al., "CD4 receptor binding peptides that block HIV infectivity cause human monocyte chemotaxis," *FEBS Lett.* 211: 17–22 [1987].

Rufini et al., "β–Bungarotoxin–Mediated Liposome Fusion: Spectroscopic Characterization by Fluorescence and ESR," *Biochemistry* 29:9644–9651 (1990).

Sacerdote et al., "Vasoactive Intestinal Peptide 1–12: A Ligand for the CD4 (T4)/Human Immunodeficiency Virus Receptor," *J. Neuroscience Res.* 18:102–107 [1987].

Shepley et al., "Monoclonal antibody identification of a 100–kDa membrane protein in HeLa cells and human spinal cord involved in poliovirus attachment," *Proc. Natl. Acad. Sci.* 85: 7743–7747 [1988].

Smith and Ekiel, *Phosphorous–31 NMR, Principles and Applications*, pp. 447–475; Academic Press, Orlando (1984).

* cited by examiner

| SOLUBILITY IN WATER | ABILITY TO FORM FILMS AND LIPOSOMES | FILM AND LIPOSOME COLOR | BASIC COLORIMETRIC RESPONSE |
|---|---|---|---|
| HIGH | YES | BLUE | YES |
| LOW | NO | NA | NA |
| LOW | NO | NA | NA |
| HIGH | YES | BLUE | YES |
| HIGH | YES | BLUE | YES |

| SOLUBILITY IN WATER | ABILITY TO FORM FILMS AND LIPOSOMES | FILM AND LIPOSOME COLOR | BASIC COLORIMETRIC RESPONSE |
|---|---|---|---|
| HIGH | YES | BLUE | YES |
| HIGH | YES | DARK BLUE | YES |
| VERY HIGH | YES | DARK BLUE | NO |
| VERY HIGH | NA | NA | NA |

FIG. 10B

PROPERTIES AND COLORIMETRIC RESPONSE OF GM1 BIOSENSING MONOLAYER ASSEMBLY

| FILM COMPOSITION | INITIAL ABSORBANCE | MONOLAYER TRANSFER RATE | CR IN BUFFER | CR IN ANALYTE |
| --- | --- | --- | --- | --- |
| 100% PDA | 0.052 | 0.94 | 0.02 | 0.02 |
| 5% GM1/95% PDA | 0.049 | 0.89 | 0.03 | 0.03 |
| 20% GM1/80% PDA | 0.018 | 0.34 | 0.03 | 0.04 |
| 5% SA-PDA/95% PDA | 0.038 | 0.77 | 0.06 | 0.07 |
| 20% SA-PDA/80% PDA | 0.032 | 0.62 | 0.14 | 0.15 |
| 5% GM1/5% SA-PDA/90% PDA | 0.036 | 0.87 | 0.06 | 0.28 |
| 20% GM1/5% SA-PDA/75% PDA | 0.014 | 0.33 | 0.10 | 0.13 |

| Solvent | Saturation concentration in water (wt%) | Solvent | Saturation concentration in water (wt%) |
|---|---|---|---|
| hexane | 0.0011 | 1-octanol | 0.054 |
| cyclohexane | 0.0055 | 1-hexanol | 0.077 |
| diethylether | 6.0 | 1-butanol | 7.45 |
| toluene | 0.051 | $CCl_4$ | 0.077 |
| benzene | 0.179 | $CHCl_3$ | 0.815 |
| | | $CH_2Cl_2$ | 1.3 |

ACIDIC HEAD GROUP 2.4 (PDA)

2.5 (GLY-PDA)

NEUTRAL HEAD GROUP 2.6 (EA-PDA)

2.7

BASIC HEAD GROUP 2.8 (EDA-PDA)

2.9 (PEG-PDA)

ZWITTERIONIC HEAD GROUP 2.10

HYDROPHOBIC HEAD GROUP 2.11

2.12

2.13

DIRECT COLORIMETRIC DETECTION OF BIOCATALYSTS

This application claims priority benefit of U.S. provisional application No. 60/039,749, filed Mar. 3, 1997, which is hereby incorporated herein by reference in its entirety.

This invention was made in part during work partially supported by the U.S. Department of Energy under DOE Contract No.: DE-AC03-76SF00098. The government has certain rights in the invention.

FIELD OF THE INVENTION

The present invention relates to methods and compositions for the direct detection of membrane conformational changes through the detection of color changes in biopolymeric materials. In particular, the present invention allows for the direct colorimetric detection of membrane modifying reactions and analytes responsible for such modifications and for the screening of reaction inhibitors.

BACKGROUND OF THE INVENTION

Measuring and identifying the activity of various enzymes and other molecules involved in membrane rearrangement (e.g., lipid cleavage, polymerization, lipid flipping, transmembrane signalling, vesicle formation, lipidation, glycosylation, ion channeling, molecular rearrangement, and phosphorylation, among others) is important for the development of methods and compositions for regulating membrane biology and associated processes (e.g., signal transduction). Such methods and compositions will find use in regulating and treating numerous conditions (e.g., cancer, diabetes, viral infection, and obesity to name a few) and physiological processes (e.g., memory, aging, and metabolism to name a few).

Interfacial catalysis provides one example of such membrane reorganization and illustrates the benefits and limitations of current technologies in characterizing and exploiting these membrane reorganizations. Interfacial catalysis on biomembranes covers a range of enzyme classes such as lipolytic enzymes, acyltransferases, protein kinases, and glycosidases, and plays a key role in extra- and intracellular processes. In particular, lipolytic enzymes are involved in important biochemical processes including fat digestion and signal transduction. Recent interest in one such enzyme, phospholipase $A_2$ ($PLA_2$) (See e.g., Kini, *Venom Phospholipase $A_2$ Enzymes*, Wiley, Chichester [1997]; and Waite, *The Phospholipases*, Plenum Press, New York [1987]) is motivated by its role in the release of arachidonate and lysophospholipids from membranes. These compounds are the precursors for the biosynthesis of eicosanoids (e.g., prostaglandins, leukotrienes, and hydroperoxy fatty acids) that have been implicated in a range of inflammatory diseases such as asthma, ischaemia, and rheumatoid arthritis (See e.g., Bomalaski and Clark, Arthritis and Rheumatism 36, 190 [1993]; Ramirez and Jain, Proteins: Structure Function, and Genetics, 9, 229 [1991]; and Dennis and Wong, *Phospholipase $A_2$: Role and Function in Inflammation*, Plenum, New York [1990]) and are likely involved in a host of other physiological processes ranging from vision (See e.g., Camras et al., Ophthamology 103, 1916 [1996]), platelet aggregation (See e.g., Wu, J. Formos. Med. Assoc. 95, 661 [1996]), adipocyte differentiation (See e.g., Casimir et al., Differentiation 60, 203 [1996]), and luteolysis (See e.g., Tsai and Wiltbank, Biol. Reprod. 57, 1016 [1997]). Accordingly, the identification of $PLA_2$ inhibitors is an active area of current research that may lead to the development of novel therapeutics and new biochemical insights into the mechanisms of enzyme activity (Dennis, supra; Gelb et al., FASEB Journal 8, 916 [1994]; and Lin and Gelb, J. Am. Chem. Soc. 115, 3932 [1993]).

$PLA_2$ catalyzes the hydrolysis of an acyl ester bond exclusively at the 2-acyl position in glycerophospholipids, yielding free fatty acid and lysophospholipid. Typical methods for measuring this activity include discontinuous radiochemical (Ehnholm and Kuusi, Meth. Enzymol, 129, 716 [1986]), fluorescent (Bayburt et al., Analytical Biochemistry, 232, 7 [1995]), and spectrophotometric techniques (Reynolds et al., Analytical Biochemistry 204, 190 [1992]). In these measurements, labeled acyl phospholipids are used as substrates, and enzyme activity is evaluated by the radioactivity, fluorescence, or absorbance of the cleaved fatty acids. Some procedures, and particularly radiolabel methods, may require that the cleaved fatty acids be extracted and isolated from the unreacted substrate by thin layer chromatography of HPLC. The extraction step and the need for synthetic labeled substrates are disadvantages when considering rapid analysis of enzyme activity, for example in high throughput assays that screen potential enzyme inhibitors. Furthermore, phospholipase catalysis is sensitive to the chemical structure of the phospholipid substrate (Grainger et al., Biochimica et Biophysica Acta 1022, 146 [1990]; and Wu and Cho, Analytical Biochemistry 221, 152 [1994]). Therefore the use of non-labeled naturally occurring substrates is highly desirable.

This need for non-labeled naturally occurring substrates applies not only to phospholipase $A_2$ characterization, but also to other phospholipases (e.g., phospholipase C and phospholipase D), lipases in general (e.g., triacylglycerol lipases, lipoprotein lipases, and pancreatic lipases), other membrane modifing enzymes (e.g., lipolytic enzymes, acyltransferases, protein kinases, and glycosidase), and any other natural or artificial membrane modifying events. In particular, methods and compositions that provide simple detection of the modifying events and that allow high throughput screening of inhibitors are desired.

SUMMARY OF THE INVENTION

The present invention relates to methods and compositions for the direct detection of membrane conformational changes through the detection of color changes in biopolymeric materials. In particular, the present invention allows for the direct colorimetric detection of membrane modifying reactions and analytes responsible for such modifications and for the screening of reaction inhibitors.

The presently claimed invention provides methods for detecting a reaction, comprising: providing biopolymeric material comprising reaction substrate and a plurality of self-assembling monomers, and a reaction means; exposing the reaction means to the biopolymeric material; and detecting a color change in the biopolymeric material which indicates at least a partial occurrence of the reaction. In some embodiments, the method further comprises the step of quantifying the color change in the biopolymeric material.

In some embodiments, the reaction means comprises a lipid cleavage means. In particular embodiments, the cleavage means comprises a lipase. In specific embodiments, the lipase is selected from the group consisting of phospholipase $A_2$, phospholipase C, and phospholipase D.

The presently claimed invention provides methods wherein the biopolymeric materials are selected from the group consisting of liposomes, films, tubules, helical assemblies, fiber-like assemblies, and solvated polymers. In some embodiments, the self assembling monomers of the biopolymeric materials comprise diacetylene monomers. In some embodiments, the self assembling monomers comprise diacetylene monomers selected from the group consisting of 5,7-docosadiynoic acid, 5,7-pentacosadiynoic acid, 10,12-pentacosadiynoic acid, and combinations thereof. In other embodiments, the self-assembling monomers are selected from the group consisting of acetylenes, alkenes, thiophenes, polythiophenes, siloxanes, poly-silanes, anilines, pyrroles, polyacetylenes, poly (para-phylenevinylene), poly (para-phylene), vinylpyridinium, and combinations thereof.

The presently claimed invention provides methods wherein the biopolymeric material further comprises one or more ligands. In some embodiments, the ligand is selected from the group consisting of proteins, antibodies, carbohydrates, nucleic acids, drugs, chromophores, antigens, chelating compounds, short peptides, pepstatin, Diels-Alder reagents, molecular recognition complexes, ionic groups, polymerizable groups, linker groups, electron donors, electron acceptor groups, hydrophobic groups, hydrophilic groups, receptor binding groups, trisaccharides, tetrasaccharides, ganglioside $G_{M1}$, ganglioside $G_{T1b}$, sialic acid, and combinations thereof. In certain embodiments, the ligands have affinity for the reaction means.

The presently claimed invention also provides methods wherein the biopolymeric material further comprises one or more dopants. In some embodiments, the dopant is selected from the group consisting of surfactants, polysorbate, octoxynol, sodium dodecyl sulfate, polyethylene glycol, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cholesterol, steroids, cerebroside, lysophosphatidylcholine, D-erythroshingosine, sphingomyelin, dodecyl phosphocholine, N-biotinyl phosphatidylethanolamine and combinations thereof. In specific embodiments, the dopants comprise diacetylene derivatives selected from the group consisting of sialic acid-derived diacetylene, lactose-derived diacetylene, amino acid-derived diacetylene, and combinations thereof.

In some embodiments, the biopolymeric material further comprises a support, wherein the biopolymeric material is immobilized to the support. In particular embodiments, the support is selected from the group consisting of polystyrene, polyethylene, teflon, mica, sephadex, sepharose, polyacrynitriles, filters, glass, gold, silicon chips, and silica.

The presently claimed invention further provides methods for detecting the presence of an analyte, comprising providing biopolymeric material comprising analyte substrate and a plurality of self-assembling monomers; exposing a sample suspected of containing the analyte to the biopolymeric material; and detecting a color change in the biopolymeric material, which indicates the presence of the analyte. In some embodiments, the analyte comprises a lipid cleavage means. In particular embodiments, the cleavage means comprises a lipase. In specific embodiments, the lipase is selected from the group consisting of phospholipase $A_2$, phospholipase C, and phospholipase D. In some embodiments, the biopolymeric material further comprises one or more ligands. In certain embodiments, the ligands have affinity for the analyte.

The presently claimed invention further provides methods for detecting inhibitors, comprising: providing biopolymeric material comprising reaction substrate and a plurality of self-assembling monomers, a reaction means, and a sample suspected of containing an inhibitor; combining the biopolymeric material and the sample suspected of containing an inhibitor; exposing the biopolymeric material and the sample suspected of containing an inhibitor to the reaction means; and detecting a color change in the biopolymeric material, thereby detecting the activity of the inhibitor. In some embodiments, the detecting a color change in the biopolymeric material comprises comparing the color change to one or more control samples. In some embodiments, the method further comprises the step of quantitating the color change in the biopolymeric material.

In some embodiments, the reaction means comprises a lipid cleavage means. In particular embodiments, the cleavage means comprises a lipase. In specific embodiments, the lipase is selected from the group consisting of phospholipase $A_2$, phospholipase C, and phospholipase D.

DESCRIPTION OF THE FIGURES

FIG. 21 shows the properties of polydiacetylene monolayers with and without sialic acid-derived PDA and ganglioside $G_{M1}$.

DEFINITIONS

Figure 1:
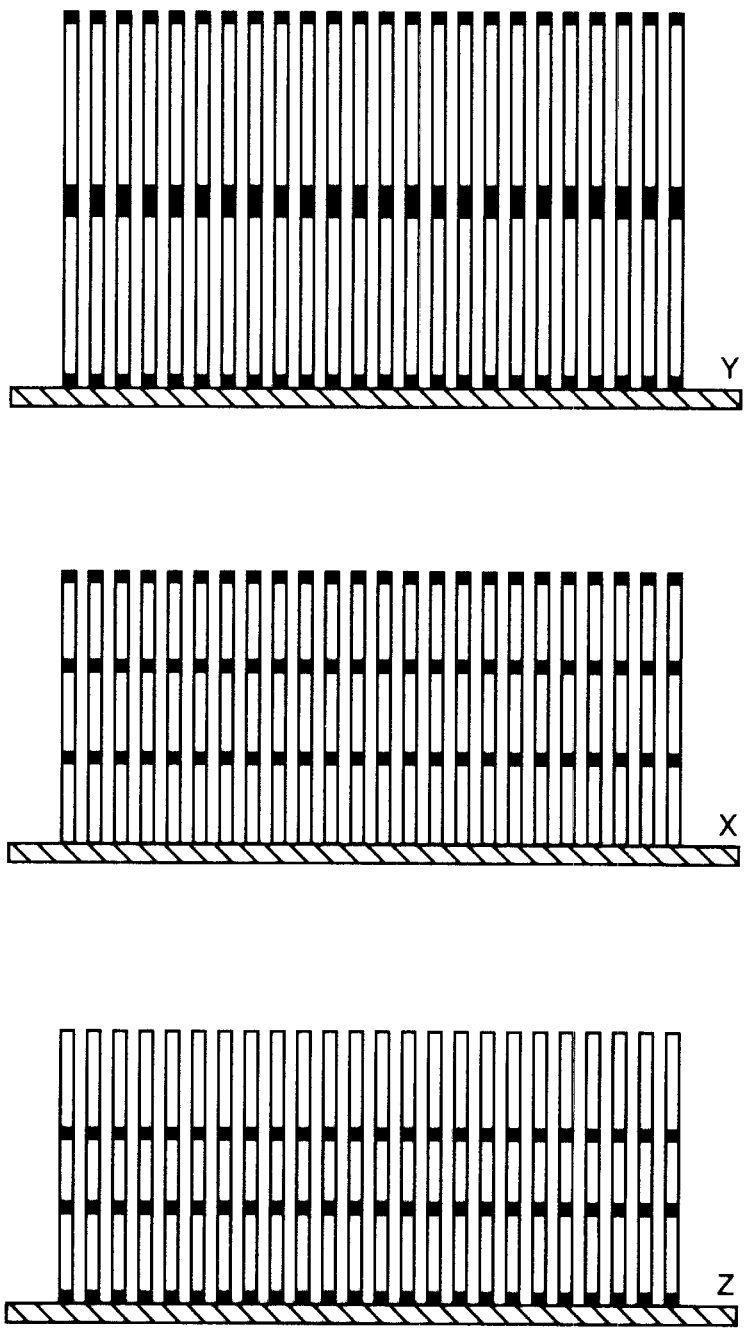
FIG. 1 shows a schematic representation of biopolymeric films. Y is a centrosymmetric multilayer film, while films X and Z are noncentrosymmetric multilayers.

To facilitate an understanding of the present invention, a number of terms and phrases are defined below:

As used herein, the term "reaction" refers to any change or transformation in which a substance (e.g, molecules, membranes, and molecular assemblies) combines with other substances, interchanges constituents with other substances, decomposes, rearranges, or is otherwise chemically altered. As used herein, the term "reaction means" refers to any means of initiating and/or catalyzing a reaction. Such reaction means include, but are not limited to, enzymes, temperature changes, and pH changes. The phrase "affinity for said reaction means" refers to compounds with the ability to specifically associate (e.g, bind) to a given reaction mean, although not necessarily a substrate for the reaction means. For example, a PLA$_2$ antibody has affinity for PLA$_2$, but is not the substrate for the enzyme.

As used herein, the term "immobilization" refers to the attachment or entrapment, either chemically or otherwise, of material to another entity (e.g, a solid support) in a manner that restricts the movement of the material.

As used herein, the terms "material" and "materials" refer to, in their broadest sense, any composition of matter.

As used herein, the term "biopolymeric material" refers to materials composed of polymerized biological molecules (e.g., lipids, proteins, carbohydrates, and combinations thereof). Such materials include, but are not limited to, films, vesicles, liposomes, multilayers, aggregates, membranes, and solvated polymers (e.g, polythiophene aggregates such as rods and coils in solvent). Biopolymeric material can contain molecules that are not part of the polymerized matrix (i.e., molecules that are not polymerized).

As used herein the term "protein" is used in its broadest sense to refer to all molecules or molecular assemblies containing two or more amino acids. Such molecules include, but are not limited to, proteins, peptides, enzymes, antibodies, receptors, lipoproteins, and glycoproteins.

As used herein the term "antibody" refers to a glycoprotein evoked in an animal by an immunogen (antigen). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "biopolymeric films" refers to polymerized organic films that are used in a thin section or in a layer form. Such films can include, but are not limited to, monolayers and bilayers. Biopolymeric films can mimic biological cell membranes (e.g., in their ability to interact with other molecules such as proteins or analytes).

As used herein, the term "sol-gel" refers to preparations composed of porous metal oxide glass structures. Such structures can have biological or other material entrapped within the porous structures. The phrase "sol-gel matrices" refers to the structures comprising the porous metal oxide glass with or without entrapped material. The term "sol-gel material" refers to any material prepared by the sol-gel process including the glass material itself and any entrapped material within the porous structure of the glass. As used herein, the term "sol-gel method" refers to any method that results in the production of porous metal oxide glass. In some embodiments, "sol-gel method" refers to such methods conducted under mild temperature conditions. The terms "sol-gel glass" and "metal oxide glass" refer to glass material prepared by the sol-gel method and include inorganic material or mixed organic/inorganic material. The materials used to produce the glass can include, but are not limited to, aluminates, aluminosilicates, titanates, ormosils (organically modified silanes), and other metal oxides.

As used herein, the term "direct calorimetric detection" refers to the detection of color changes without the aid of an intervening processing step (e.g., conversion of a color change into an electronic signal that is processed by an interpreting device). It is intended that the term encompass visual observing (e.g., observing with the human eye) as well as detection by simple spectrometry.

As used herein, the term "analytes" refers to any material that is to be analyzed. Such materials can include, but are not limited to, ions, molecules, antigens, bacteria, compounds, viruses, cells, antibodies, and cell parts.

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s). This is in contrast to "non-selective binding," whereby interactions are arbitrary and not based on structural compatibilities of the molecules.

As used herein, the term "biosensors" refers to any sensor device that is partially or entirely composed of biological molecules. In a traditional sense, the term refers to "an analytical tool or system consisting of an immobilized biological material (such as enzyme, antibody, whole cell, organelle, or combination thereof) in intimate contact with a suitable transducer device which will convert the biochemical signal into a quantifiable electrical signal" (Gronow, Trends Biochem. Sci. 9: 336 [1984]).

As used herein, the term "transducer device" refers to a device that is capable of converting a non-electrical phenomenon into electrical information, and transmitting the information to a device that interprets the electrical signal. Such devices can include, but are not limited to, devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave.

As used herein, the term "miniaturization" refers to a reduction in size, such as the size of a sample to increase utility (e.g., portability, ease of handling, and ease of incorporation into arrays).

As used herein, the term "stability" refers to the ability of a material to withstand deterioration or displacement and to provide reliability and dependability.

As used herein, the term "conformational change" refers to the alteration of the molecular structure of a substance. It is intended that the term encompass the alteration of the structure of a single molecule or molecular aggregate (e.g., the change in structure of polydiacetylene upon interaction with an analyte).

As used herein, the term "small molecules" refers to any molecule with low molecular weight (i.e., less than 10,000 atomic mass units and preferably less than 5,000 atomic mass units) that binds to ligands, interacts with ligands, or interacts with biopolymeric material in a manner that creates a conformational change.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), CV Mosby St. Louis, pp 13–15).

As used herein, the term "membrane" refers to, in its broadest sense, a sheet or layer of material. It is intended that the term encompass all "biomembranes" (ie., any organic membrane including, but not limited to, plasma membranes, nuclear membranes, organelle membranes, and synthetic membranes). Typically, membranes are composed of lipids, proteins, glycolipids, steroids, sterols and/or other components. As used herein, the term "membrane fragment" refers to any portion or piece of a membrane. The term "polymerized membrane" refers to membranes that have undergone partial or complete polymerization.

As used herein, the terms "membrane rearrangement" and "membrane conformational change" refer to any alteration in the structure of a membrane. Such alterations can be caused by physical perturbation, heating, enzymatic and chemical reactions, among other events. Reactions that can result in membrane rearrangement include, but are not limited to lipid cleavage, polymerization, lipid flipping, transmembrane signalling, vesicle formation, lipidation, glycosylation, ion channeling, molecular rearrangement, and phosphorylation. Enzymatic catalysis that results in membrane rearrangement can result from free enzymes interacting with the biopolymeric material (e.g., reacting with an enzyme substrate in the biopolymeric material) and can result from enzymatic activity present in certain analytes (e.g., viruses, bacteria, and toxins among others).

As used herein, the term "lipid cleavage" refers to any reaction that results in the division of a lipid or lipid-comprising material into two or more portions. "Lipid cleavage means" refers to any means of initiating and/or catalyzing lipid cleavage. Such lipid cleavage means include, but are not limited to enzymes, free radical reactions, and temperature changes.

As used herein, the term "polymerization" encompasses any process that results in the conversion of small molecular monomers into larger molecules consisting of repeated units. Typically, polymerization involves chemical crosslinking of monomers to one another.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "volatile organic compound" or "VOC" refers to organic compounds that are reactive (i.e., evaporate quickly, explosive, corrosive, etc.), and typically are hazardous to human health or the environment above certain concentrations. Examples of VOCs include, but are not limited to, alcohols, benzenes, toluenes, chloroforms, and cyclohexanes.

As used herein, the term "enzyme" refers to molecules or molecule aggregates that are responsible for catalyzing chemical and biological reactions. Such molecules are typically proteins, but can also comprise short peptides, RNAs, ribozymes, antibodies, and other molecules.

As used herein, the term "substrate," in one sense, refers to a material or substance on which an enzyme or other reaction means acts. In another sense, it refers to a surface on which an sample grows or is attached. The term "reaction substrate" refers to the substrate for a reaction means (e.g., a "substrate lipid" reacted by a lipid cleavage means). As used herein, the term "analyte substrate" refers to a material or substance upon which an analyte reacts. For example, the analyte can be an enzyme and the analyte substrate is an enzyme substrate. In another sense, the analyte can be a pathogen and the analyte substrate comprises a material or sample that is altered by a "reaction means" associated with the pathogen.

As used herein, the term "lipase" refers to any of a group of hydrolytic enzymes that acts on ester bonds in lipids. Such lipases include, but are not limited to, pancreatic lipase that catalyses the hydrolysis of triacylglycerols, lipoprotein lipase that catalyzes the hydrolysis of triacylglycerols to glycerol and free fatty acids, and phospholipases, among others. The term "phospholipase" refers to enzymes that cleave phospholipids by the hydrolysis of carbon-oxygen or phosphorus-oxygen bonds. Phospholipases include, but are not limited to, phospholipases $A_1$, $A_2$, C, and D.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "peptide" refers to any substance composed of two or more amino acids.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "chromophore" refers to molecules or molecular groups responsible for the color of a compound, material, or sample.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the term "chelating compound" refers to any compound composed of or containing coordinate links that complete a closed ring structure. The compounds can combine with metal ions, attached by coordinate bonds to at least two of the nonmetal ions.

As used herein, the term "molecular recognition complex" refers to any molecule, molecular group, or molecular complex that is capable of recognizing (i.e., specifically interacting with) a molecule. For example, the ligand binding site of a receptor would be considered a molecular recognition complex.

As used herein, the term "ambient condition" refers to the conditions of the surrounding environment (e.g., the temperature of the room or outdoor environment in which an experiment occurs).

As used herein, the term "room temperature" refers, technically, to temperatures approximately between 20 and 25 degrees centigrade. However, as used generally, it refers to the any ambient temperature within a general area in which an experiment is taking place.

As used herein, the terms "home testing" and "point of care testing" refer to testing that occurs outside of a laboratory environment. Such testing can occur indoors or outdoors at, for example, a private residence, a place of business, public or private land, in a vehicle, under water, as well as at the patient's bedside.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, the phrase "free floating aggregates" refers to aggregates that are not immobilized.

As used herein, the term "encapsulate" refers to the process of encompassing, encasing, or otherwise associating two or more materials such that the encapsulated material is immobilized within or onto the encapsulating material.

As used herein, the term "optical transparency" refers to the property of matter whereby the matter is capable of transmitting light such that the light can be observed by visual light detectors (e.g., eyes and detection equipment).

As used herein, the term "biologically inert" refers to a property of material whereby the material does not chemically react with biological material.

As used herein, the term "organic solvents" refers to any organic molecules capable of dissolving another substance. Examples include, but are not limited to, chloroform, alcohols, phenols, and ethers.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils.

As used herein, the term "films" refers to any material deposited or used in a thin section or in a layer form.

As used herein, the term "vesicle" refers to a small enclosed structures. Often the structures are membranes composed of lipids, proteins, glycolipids, steroids or other components associated with membranes. Vesicles can be naturally generated (e.g., the vesicles present in the cytoplasm of cells that transport molecules and partition specific cellular functions) or can be synthetic (e.g., liposomes).

As used herein, the term "liposome" refers to artificially produced spherical lipid complexes that can be induced to segregate out of aqueous media.

As used herein, the term "biopolymeric liposomes" refers to liposomes that are composed entirely, or in part, of biopolymeric material.

As used herein, the term "tubules" refers to materials comprising small hollow cylindrical structures.

As used herein, the terms "solvated polymer," "solvated rod," and "solvated coil" refer to polymerized materials that are soluble in aqueous solution.

As used the term "multilayer" refers to structures comprised of two or more monolayers. The individual monolayers may chemically interact with one another (e.g., through covalent bonding, ionic interactions, van der Waals' interactions, hydrogen bonding, hydrophobic or hydrophilic assembly, and stearic hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies. "Surfactant molecular assemblies" refers to an assembly of surface active agents that contain chemical groups with opposite polarity, form oriented monolayers at phase interfaces, form micelles (colloidal particles in aggregation colloids), and have detergent, foaming, wetting, emulsifying, and dispersing properties.

As used herein, the term "homopolymers" refers to materials comprised of a single type of polymerized molecular species. The phrase "mixed polymers" refers to materials comprised of two or more types of polymerize molecular species.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the term "dopant" refers to molecules that are added to biopolymeric materials to change the material's properties. Such properties include, but are not limited to, colorimetric response, color, sensitivity, durability, robustness, amenability to immobilization, temperature sensitivity, and pH sensitivity. Dopant materials include, but are not limited to, lipids, cholesterols, steroids, ergosterols, polyethylene glycols, proteins, peptides, or any other molecule (e.g., surfactants, polysorbate, octoxynol, sodium dodecyl sulfate, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cerebroside, lysophosphatidylcholine, D-erythroshingosine, sphingomyelin, dodecyl phosphocholine, N-biotinyl phosphatidylethanolamine, and other synthetic or natural components of cell membranes) that can be associated with a membrane (e.g., liposomes and films).

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the terms "head group" and "head group functionality" refer to the molecular groups present an the ends of molecules (e.g., the carboxylic acid group at the end of fatty acids).

As used herein, the term "hydrophilic head-group" refers to ends of molecules that are substantially attracted to water by chemical interactions including, but not limited to, hydrogen-bonding, van der Waals' forces, ionic interactions, or covalent bonds. As used herein, the term "hydrophobic head-group" refers to ends of molecules that self-associate with other hydrophobic entities, resulting in their exclusion from water.

As used herein, the term "carboxylic acid head groups" refers to organic compounds containing one or more carboxyl (—COOH) groups located at, or near, the end of a molecule. The term carboxylic acid includes carboxyl groups that are either free or exist as salts or esters.

As used herein, the term "detecting head group" refers to the molecular group contained at the end of a molecule that is involved in detecting a moiety (e.g., an analyte).

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the phrase "polymeric assembly surface" refers to polymeric material that provides a surface for the assembly of further material (e.g., a biopolymeric surface of a film or liposome that provides a surface for attachment and assembly of ligands).

As used herein, the term "formation support" refers to any device or structure that provides a physical support for the production of material. In some embodiments, the formation support provides a structure for layering and/or compressing films.

As used herein, the term "diacetylene monomers" refers to single copies of hydrocarbons containing two alkyne linkages (i.e., carbon/carbon triple bonds).

As used herein, the terms "standard trough" and "standard Langmuir-Blodgett trough" refer to a device, usually made of teflon, that is used to produce Langmuir films. The device contains a reservoir that holds an aqueous solution and moveable barriers to compress film material that are layered onto the aqueous solution (See e.g., Roberts, *Langmuir-Blodgett Films*, Plenum, New York, [1990]).

As used herein, the term "crystalline morphology" refers to the configuration and structure of crystals that can include, but are not limited to, crystal shape, orientation, texture, and size.

As used herein, the term "domain boundary" refers to the boundaries of an area in which polymerized film molecules are homogeneously oriented. For example, a domain boundary can be the physical structure of periodic, regularly arranged polydiacetylene material (e.g., striations, ridges, and grooves).

As used herein, the term "domain size" refers to the typical length between domain boundaries.

As used the terms "conjugated backbone" and "polymer backbone" refer to the ene-yne polymer backbone of polymerized diacetylenic films that, on a macroscopic scale, appears in the form of physical ridges or striations. The term "polymer backbone axis" refers to an imaginary line that runs parallel to the conjugated backbone. The terms "intra-backbone" and "interbackbone" refer to the regions within a given polymer backbone and between polymer backbones, respectively. The backbones create a series of lines or "linear striations," that extend for distances along the template surface.

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., $C_8$–$C_9$). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nM) but greater than that of X-rays (i.e., greater than approximately 0.1 nM). Ultraviolet radiation possesses greater energy than visible light and is therefore, more effective at inducing photochemical reactions.

As used herein, the term "chromatic transition" refers to the changes of molecules or material that result in an alteration of visible light absorption. In some embodiments, chromatic transition refers to the change in light absorption of a sample, whereby there is a detectable color change associated with the transition. This detection can be accomplished through various means including, but not limited to, visual observation and spectrophotometry.

As used herein, the term "thermochromic transition" refers to a chromatic transition that is initiated by a change in temperature.

As used herein, the term "solid support" refers to a solid object or surface upon which a sample is layered or attached. Solid supports include, but are not limited to, glass, metals, gels, and filter paper, among others. "Hydrophobized solid support" refers to a solid support that has been chemically treated or generated so that it attracts hydrophobic entities and repels water.

As used herein, the term "film-ambient interface" refers to a film surface exposed to the ambient environment or atmosphere (i.e., not the surface that is in contact with a solid support).

As used herein, the term "formation solvent" refers to any medium, although typically a volatile organic solvent, used to solubilize and distribute material to a desired location (e.g., to a surface for producing a film or to a drying receptacle to deposit liposome material for drying).

As used herein, the term "micelle" refers to a particle of colloidal size that has a hydrophilic exterior and hydrophobic interior.

As used herein, the term "topochemical reaction" refers to reactions that occur within a specific place (e.g., within a specific portion of a molecule or a reaction that only occurs when a certain molecular configuration is present).

As used herein, the term "molding structure" refers to a solid support used as a template to design material into desired shapes and sizes.

As used herein, the terms "array" and "patterned array" refer to an arrangement of elements (i.e., entities) into a material or device. For example, combining several types of biopolymeric material with different analyte recognition groups into an analyte-detecting device, would constitute an array.

As used herein the term "interferants" refers to entities present in an analyte sample that are not the analyte to be detected and that, preferably, a detection device will not identify, or would differentiate from the analyte(s) of interest.

As used herein, the term "badge" refers to any device that is portable and can be carried or worn by an individual working in an analyte detecting environment.

As used herein, the term "device" refers to any apparatus (e.g., multi-well plates and badges) that contain biopolymeric material. The biopolymeric material may be immobilized or entrapped in the device. More than one type of biopolymeric material can be incorporated into a single device.

As used herein, the term "halogenation" refers to the process of incorporating or the degree of incorporation of halogens (i.e., the elements fluorine, chlorine, bromine, iodine and astatine) into a molecule.

As used herein, the term "aromaticity" refers to the presence of aromatic groups (i.e., six carbon rings and derivatives thereof) in a molecule.

As used herein, the phrase "water-immiscible solvents" refers to solvents that do not dissolve in water in all proportions. The phrase "water-miscible solvents" refers to solvents that dissolve in water in all proportions.

As used herein, the terms "positive," "negative," and "zwitterionic charge" refer to molecules or molecular groups that contain a net positive, negative, or neutral charge, respectively. Zwitterionic entities contain both positively and negatively charged atoms or groups whose charges cancel (i.e., whose net charge is 0).

As used herein, the term "biological organisms" refers to any carbon-based life forms.

As used herein, the term "in situ" refers to processes, events, objects, or information that are present or take place within the context of their natural environment.

As used the term "aqueous" refers to a liquid mixture containing water, among other components.

As used herein, the term "solid-state" refers to reactions involving one or more rigid or solid-like compounds.

As used herein, the term "regularly packed" refers to the periodic arrangement of molecules within a compressed film.

As used herein, the term "filtration" refers to the process of separating various constituents within a test sample from one another. In one embodiment, filtration refers to the separation of solids from liquids or gasses by the use of a membrane or medium. In alternative embodiments, the term encompasses the separation of materials based on their relative size.

As used herein, the term "inhibitor" refers to a material, sample, or substance that retards or stops a chemical reaction. The term "reaction means inhibitor" refers to inhibitors that are capable of retarding or stopping the action or activity of a given reaction means (e.g, an enzyme).

As used herein, the term "inhibitor screening" refers to any method used to identify and/or characterize inhibitors. Preferably, inhibitor screening methods provide "high throughput screening," the ability to screen a large number of samples suspected of containing inhibitors in a short period of time. It may also be desired that the inhibitor screening method provide quantifiable results to provide comparisons of inhibitor efficiency.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

GENERAL DESCRIPTION OF THE INVENTION

The present invention relates to methods and compositions for the direct detection of membrane conformational changes through the detection of color changes in biopolymeric materials. In particular, the present invention allows for the direct colorimetric detection of membrane modifying reactions and analytes responsible for such modifications and for the screening of reaction inhibitors. Upon disruption of the membrane structure of the biopolymeric materials, the materials undergo a detectable (e.g., visually detectable) color change. The present invention provides for the direct colorimetric detection of a variety of membrane disrupting events including, but not limited to, lipid cleavage, polymerization, lipid flipping, transmembrane signalling, vesicle formation, lipidation, glycosylation, ion channeling, molecular rearrangement, and phosphorylation among others. Experiments can be conducted, and results can be interpreted by an untrained observer, and the methods can be conducted under ambient conditions, making them amenable to numerous uses including, but not limited to, home testing diagnostics, field work, detection of air-borne or water-borne materials, military applications, doctor's office or point of care testing, and many other applications. The present invention provides detecting technology that does not require an energy source and is cost-efficient, stable, accurate, reliable, consistent, and robust. These enhanced qualities provide an ideal basis for use in screening new compound libraries (e.g., drug screens), identification and characterization of enzyme inhibitors, drug testing, water supply testing, and any application in which a rapid and accurate calorimetric screen is desired.

In preferred embodiments, the biopolymeric materials of the presently claimed invention offer a one-step approach to measuring enzyme activity through detection of a color change of diacetylene 'signaling' lipids that surround the natural enzyme substrate. The strategy does not require additional chemical reagents or post-hydrolysis analytical methods. Furthermore, enzyme inhibitors can be rapidly identified by simply monitoring the color changes of aqueous vesicle suspensions in a standard 96-well microtiter plate or equivalent.

Conjugated polymers (CPs) such as polydiacetylene (PDA), polythiophene, and polypyrrole display a remarkable array of color transitions arising from thermal changes (thermochromism) (Levesque and Leclerc, Chem. Mater. 8, 2843 [1996]), mechanical stress (mechanochromism) (Galiotis et al., J. Polymer Science 21, 2483 [1983]), or ion-binding (ionochromism) (Levesque, supra; and Marsella et al., Am. Chem. Soc. 117, 9842 [1995]). The color changes can be ascribed to a change in the effective conjugation length of the delocalized π-conjugated polymer backbone (Tanaka et al., Macromolecules 22, 1208 [1989]). The application of these 'smart' materials for the detection of biological targets (biochromisms) (See e.g., Charych et al., Chemistry & Biology 3, 113 [1996]; Reichert et al., J. Am. Chem. Soc. 117, 829 [1995]; Charych et al., Science 261, 585 [1993]; Pan and Charych, Langmuir 13, 1365 [1997]; Cheng and Stevens, Chemistry and Physics of Lipids 87, 41 [1997]; and Cheng and Stevens, Advanced Materials 9, 481 [1997]) is only beginning to be exploited. These materials exhibit rapid response times, selectivity, and optical signals that are easily monitored. As free-floating aggregates in solution, these lipid-based detectors show promise as simple assay systems. As immobilized films, liposomes, or other forms, these detectors provide durable, robust calorimetric sensors that can be easily incorporated into small detection devices (e.g., a detection badge).

Unlike other polymerized lipid based technologies (See e.g., U.S. Pat. Nos. 5,268,305 and 4,859,538) the methods and compositions of the presently claimed invention provide a visually detectable calorimetric change in the polymerized materials and do not require the use of a transducing device. These other technologies rely on lipid materials that are associated with transducer devices that use photometry, fluorimetry, chemiluminescence, fiber optics, grating coupler, surface plasmon resonance, potentiometric and amperometric electrodes, filed effect transistors, piezoelectric sensing, or surface acoustic wave for identifying changes in the polymerized material, interpreting the signal, and converting it into information that can be read and understood by a human. There are major drawbacks to these devices, such as their dependence on the transducing device, which prevents miniaturization and requires a power source. These disadvantages make such devices too complex, expensive, or unmanageable for many routine detection applications such as field work or home use. Additionally, many of these devices are limited by the lack of stability and availability of the biological materials.

In some embodiments, the presently claimed invention provides novel biochromatic detection methods comprising chemical modification of PDA-vesicles by interfacial enzymes such as phospholipase $A_2$ ($PLA_2$). These methods offer a new pathway of inducing the biochromic effect. In preferred embodiments, the color change of the vesicle solution is driven by hydrolysis of a natural, unlabeled enzyme substrate embedded in the PDA matrix. In other embodiments, the presently claimed invention demonstrates that the biochromatic transition of the PDA vesicles is suppressed by the addition of a known phospholipase inhibitor, providing applications in high throughput drug discovery.

The present invention also provides an array of biopolymeric materials incorporated into a single device, such that each individual section of biopolymeric material respond differently to different reactions or to a given reaction. Such arrays can be designed so that the presence of a certain reaction will produce a color change in a known location in the device, or that will produce a color change specific to the given reaction (e.g., purple to orange for reaction X and blue to red for reaction Y). It is also contemplated that other arrays will be used with the present invention, including such easily understood patterns as a "+" sign to indicate that presence of a particular substance, compound, or reaction. It is not intended that the present invention be limited to any particular array design or configuration. Thus, the present invention provides methods and compositions for the characterization of membrane rearrangements that overcome many of the disadvantages of currently available technologies (e.g., indirect detection, sample purification, cost, and use of radioactivity or other hazardous materials).

DETAILED DESCRIPTION OF THE INVENTION

The presently claimed invention comprises methods and compositions related to biopolymeric materials that change color in response to membrane rearrangements (e.g., lipid cleavage). These biopolymeric materials comprise many forms including, but not limited to, films, vesicles, tubules, multilayered structures, and solvated rods and coils. These materials are comprised of polymerized self-assembling monomers. In some embodiments, the biopolymeric materials comprise more than one species of self-assembling monomer. Some of these self-assembling monomers may lack polymerizable groups. In other embodiments, the materials further comprise dopant material(s) that alter the properties of the sensor. Dopants include, but are not limited to, polymerizable self-assembling monomers, non-polymerizable self-assembling monomers, lipids, sterols, membrane components, and any other molecule that optimizes the biopolymeric material (e.g., material stability, durability, colorimetric response, and immobilizability). The biopolymeric material may further comprise ligands (e.g., proteins, antibodies, carbohydrates, and nucleic acids). The ligands can provide attachment sites for recruiting molecules to the biopolymeric surface or can be used as binding sites for analytes, whereby the binding event causes a colorimetric change in the biopolymeric material. The various embodiments of the presently claimed invention provide the ability to colorimetrically detect a broad range reactions and analytes. With certain biopolymeric materials, a color transition in response to a reaction can be viewed by simple visual observation or, if desired, by color sensing equipment. The present invention further provides a variety of means of immobilizing the biopolymeric material to provide stability, durability, and ease of handling and use. In some embodiments, a variety of different polymeric materials are combined into a single device to produce an array. The array can be designed to detect and differentiate differing types or quantities of reactions or analytes (i.e., the array can provide quantitative and/or qualitative data). The methods and compositions of the presently claimed invention find use in a broad range of analyte detection circumstances and are particularly amenable to situations where simple, rapid, accurate, and cost-efficient detection is required.

The description of the invention is divided into: I. Forms of Biopolymeric Materials; II. Self-Assembling Monomers; III. Dopants; IV. Ligands; V. Detection of Colorimetric Changes; VI. Detection of Membrane Conformational Changes; VII. Immobilization of Biopolymeric Materials; and VIII. Arrays. The biopolymeric materials described in these sections can be designed to detect the presence of analytes (e.g., pathogens, chemicals, and proteins) or can be designed to detect membrane rearrangements (e.g., lipid cleavage events). In some embodiments, it may be desired to have biopolymeric materials that accomplish both of these functions. The optimization of the biopolymeric materials (e.g., optimization of colorimetric response, color, and stability) with regards to the detection of analytes or membrane rearrangements is often generally applicable to both scenarios. Where there are differences, it is noted.

I. Forms of Biopolymeric Materials

The biopolymeric material of the presently invention can take many physical forms including, but not limited to, liposomes, films, and multilayers, as well as braided, lamellar, helical, tubular, and fiber-like shapes, and combinations thereof. In some embodiments, the biopolymeric materials are solvated polymers in aggregate forms such as rods and coils. Each of these classes is described below, highlighting their advantages and the difficulties overcome during the development of these materials.

A. Films

In some embodiments, the biopolymeric material used in the presently claimed invention comprise biopolymeric film. As described in Example 1, biopolymeric films were prepared by layering the desired matrix-forming material (e.g., self-assembling organic monomers) onto a formation support. In preferred embodiments, the formation support was a standard Langmuir-Blodgett trough and the matrix-forming material was layered onto an aqueous surface created by filling the trough with an aqueous solution. The material was then compressed and polymerized to form a biopolymeric film. In preferred embodiments, the compression was conducted in a standard Langmuir-Blodgett trough using moveable barriers to compress the matrix-forming material. Compression was carried out until a tight-packed monolayer of the matrix-forming material was formed. Films provide a very sensitive colorimetric screen for analytes.

As described in Example 1, in some embodiments, the matrix-forming material, located within the formation support, was polymerized by ultra-violet irradiation. All methods of polymerization are contemplated by the present invention and include, but are not limited to, gamma irradiation, x-ray irradiation, chemical crosslinking, and electron beam exposure.

In some embodiments, diacetylene monomers (DA) were used as the self-assembling monomer. The diacetylene monomers (DA) were polymerized to polydiacetylene (p-PDA or PDA) using ultraviolet irradiation. In preferred embodiments, the ultraviolet radiation source is kept sufficiently far from the film to avoid causing heat damage to the film. The crystalline morphology of the polymerized film can be readily observed between crossed polarizers in an optical microscope, although this step is not required by the present invention. The conjugated backbone of alternating double and triple bonds (i.e., ene-yne) that was generated following polymerization, gave rise to intense absorptions in the visible spectrum and led to a distinct blue/purple appearance of the polymerized diacetylene film.

In certain embodiments the visibly blue films were then transferred to hydrophobized solid supports, such that the carboxylic acid head groups were exposed at the film-ambient interface (Charych et al., Science 261: 585 [1993]) to undergo further analysis, although the method of the present invention does not require this step. Linear striations typical of PDA films can be observed in the polarizing optical microscope. The material may also be characterized using atomic force microscopy or other characterization means (See e.g., Example 2).

The presently claimed invention contemplates all other means of making films, as several other methods are known in the art. For example, films can be made by solvent casing (i.e., slow evaporation of the solvent). Also, lipid monomers can be made with silane or thiol anchoring groups, which allows dipping of solid supports into the solution to form a coated solid support. Diacetylene monomers are anchored by the silane and thiol groups and are then polymerized. This method eliminates the need for a trough.

B. Liposomes

In other embodiments, the biopolymeric material used in the presently claimed invention comprises biopolymeric liposomes. Liposomes were prepared using a probe sonication method (New, *Liposomes: A Practical Approach*, Oxford University Press, Oxford, pp 33–104 [1990]), although any method that generates liposomes is contemplated. Self-assembling monomers, either alone, or associated with a desired ligand, were dried to remove the formation solvents and resuspended in deionized water. The suspension was probe sonicated and polymerized. The resulting liposome solution contained biopolymeric liposomes.

Figure 2A:
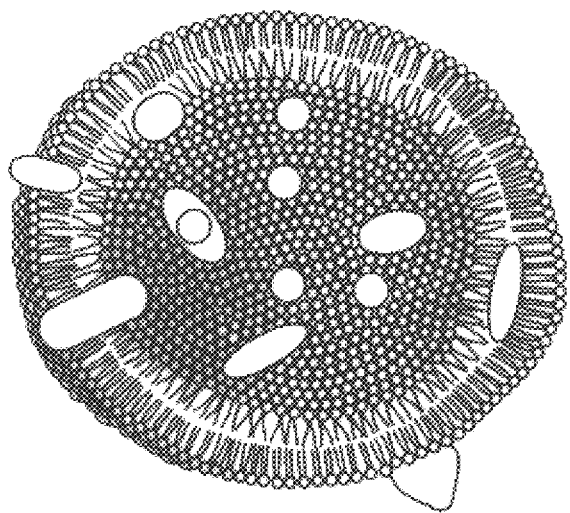
FIGS. 2A and 2B shows a schematic representation of biopolymeric liposomes. Part A is a cross-section two-dimensional view and part B is a three-dimensional view of half of a liposome.
Figure 2B:
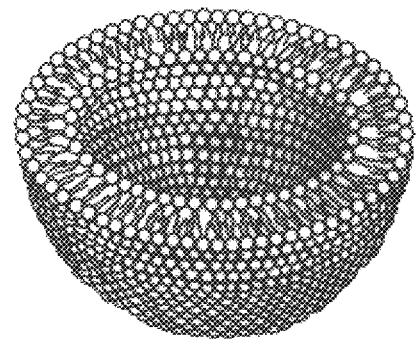

Liposomes differ from monolayers and films in both their physical characteristics and in the methods required to generate them. Monolayers and films (or multilayers) made from amphiphilic compounds are planar membranes and form a two-dimensional architecture. Monolayers and films, in this context, are solid state materials that are supported by an underlying solid substrate as shown in FIG. 1. Film Y is a centrosymmetric multilayer film, while films X and Z are noncentrosymmetric multilayers. Such materials are described in numerous articles and have been reviewed in text such as Ulman (Ulman, *An Introduction to Ultrathin Organic Films: From Langmuir-Blodgett to Self-Assembly*, Academic Press, Inc., Boston, [1991]) and Gaines (Gaines, *Insoluble Monolayers at Liquid-Gas Interfaces*, Interscience Publishers, New York, [1966]). In contrast to films and monolayers, liposomes are three-dimensional vesicles that enclose an aqueous space as shown in FIG. 2. FIG. 2 shows A) a cross-section two-dimensional view; and B) a three-dimensional view of half of a liposome. These materials are described in numerous articles and have been reviewed in texts such as New (New, *Liposomes: A Practical Approach*, IRL Press, Oxford, [1989]), and Rosoff (Rosoff, *Vesicles*, Marcel Dekker, Inc., New York, [1996]) among others. Liposomes can be constructed so that they entrap materials within their aqueous compartments. Films and monolayers do not enclose an aqueous space and do not entrap materials within a compartment. The liposomes are typically more stable and robust than the films made of the same material.

Liposomes and films are prepared using different methods. Liposomes are prepared by dispersal of amphiphilic molecules in an aqueous media and remain in the liquid phase. In contrast, monolayers and films are prepared by immobilizing amphiphilic molecules at the air-water interface. A solid support is then passed through the interface to transfer the film to the solid support. Liposomes exist within homogenous aqueous suspensions and may be created in a variety of shapes such as spheres, ellipsoids, squares, rectangles, and tubules. Thus, the surface of a liposome is in contact with liquid only—primarily water. In some respects, liposomes resemble the three-dimensional architecture of natural cell membranes. If liposomes are dried to their solid state, they may lose their shape and no longer exist in a liposomal state (i.e., are no longer "liposomes"). In contrast, films exist as planar heterogeneous coatings, immobilized onto a solid support. The surface of a monolayer or film can be in contact with air, other gases, or other liquids. Films can be dried in air and maintain their planar monolayer or multilayer structure and thus remain as "films."

Figure 3A:
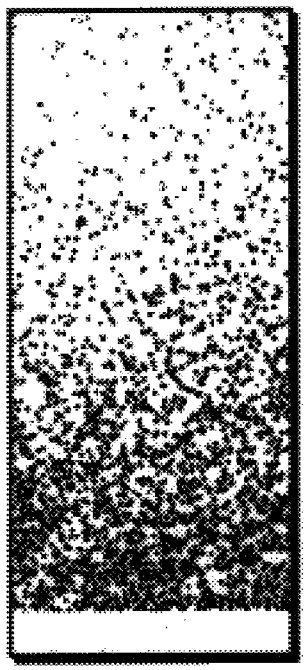
FIG. 3 shows biopolymeric 1) liposomes and 2) films comprising the same biopolymeric material and exposed to the same analyte.
Figure 3B:
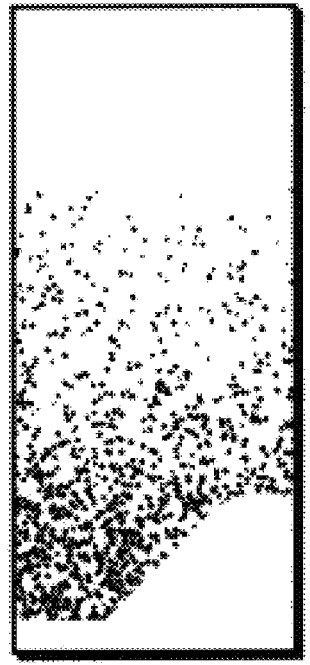

A much higher concentration of polymerized material can be achieved with liposome solutions compared to monolayer assemblies, due to their greater cross-sectional density. Liposomes have the advantage, generally, of making the color change more visually striking and increasing the colorimetric response (See e.g., FIG. 3 showing the colorimetric response of immobilized sialic-acid-containing liposomes (1) and films (2) to the presence of influenza virus).

In designing methods to generate the liposomes of the present invention, several difficulties had to be overcome. While it was initially hoped that liposomes could be generated with the self-assembling monomer material (e.g., diacetylenes) used in various film embodiments (i.e., film embodiments of the present invention discussed above and in Example 1), it was not known whether this would be possible, largely due to the differences in liposomal and film architecture. Liposomes are three-dimensional instead of two-dimensional. Therefore, it was not clear whether 1) the diacetylenic lipids would actually form liposomes at all; 2) whether they would polymerize if they were capable or forming liposomes; and/or 3) whether they would exhibit colorimetric properties even if they could be polymerized.

Regarding the first point, it was not clear that the single-chained diacetylenic lipids would actually form liposomes. This is because the majority of the literature shows that single chain molecules tend to form micelles (i.e., loosely packed single-bilayer suspensions), whereas only double chain molecules can form liposomes. Furthermore, as described by New (New, supra), the double chain molecules typically used in liposome formation are derived from natural cell membranes and usually have a classical phospholipid structure incorporating such molecular components as phosphodiglycerides and sphingolipids, unlike the diacetylenic lipids of the present invention.

Figure 4:
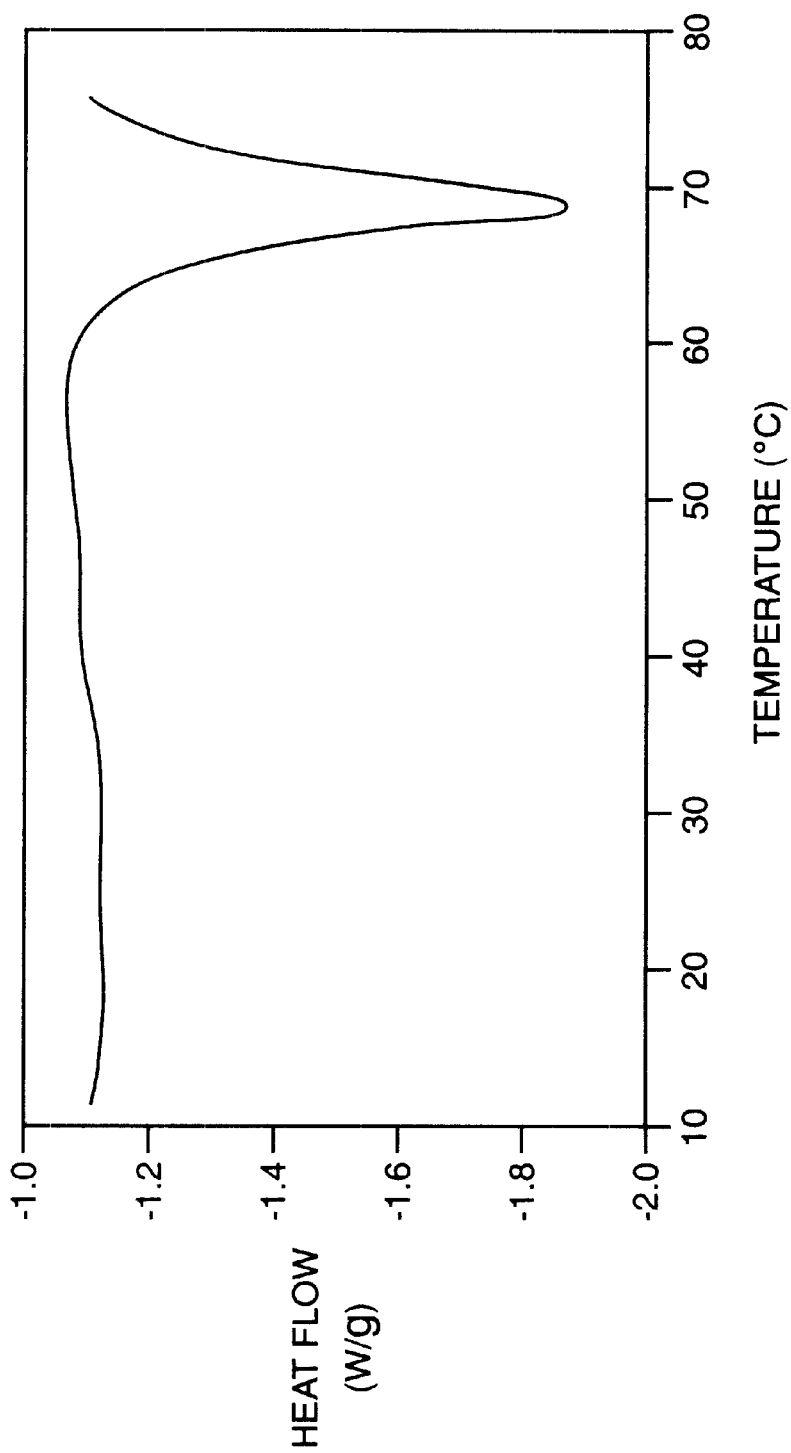
FIG. 4 shows a heating curve depicting the large main phase transition for unpolymerized liposomes prepared from PDA monomer.

Initially, attempts to form liposomes with diacetylenic lipids using standard methods such as vortexing or bath sonications were tried (i.e., methods that are similar to those commonly applied to phospholipids). These methods failed to form liposomes and resulted in the formation of an insoluble, non-dispersed, non-characterizable mixture. This mixture did not exhibit colorimetric properties. Applying differential scanning calorimetry, it was determined that the $t_m$ (main phase transition temperature) of the lipids was much higher than their natural phospholipid counterparts. For example, FIG. 4 shows a heating curve depicting the large main phase transition for unpolymerized liposomes prepared from lysine-derivated PDA monomer. Therefore, it was necessary to employ higher energy methods such as ultrasonic probe sonication and heating, to raise the temperature above $t_m$ and to disperse the lipid. Under these conditions (e.g., as described in Example 1) liposomes were formed, as evidenced by light scattering and transmission electron microscopy with a size in accordance with a liposome (i.e., approximately 100 nm).

Figure 5:
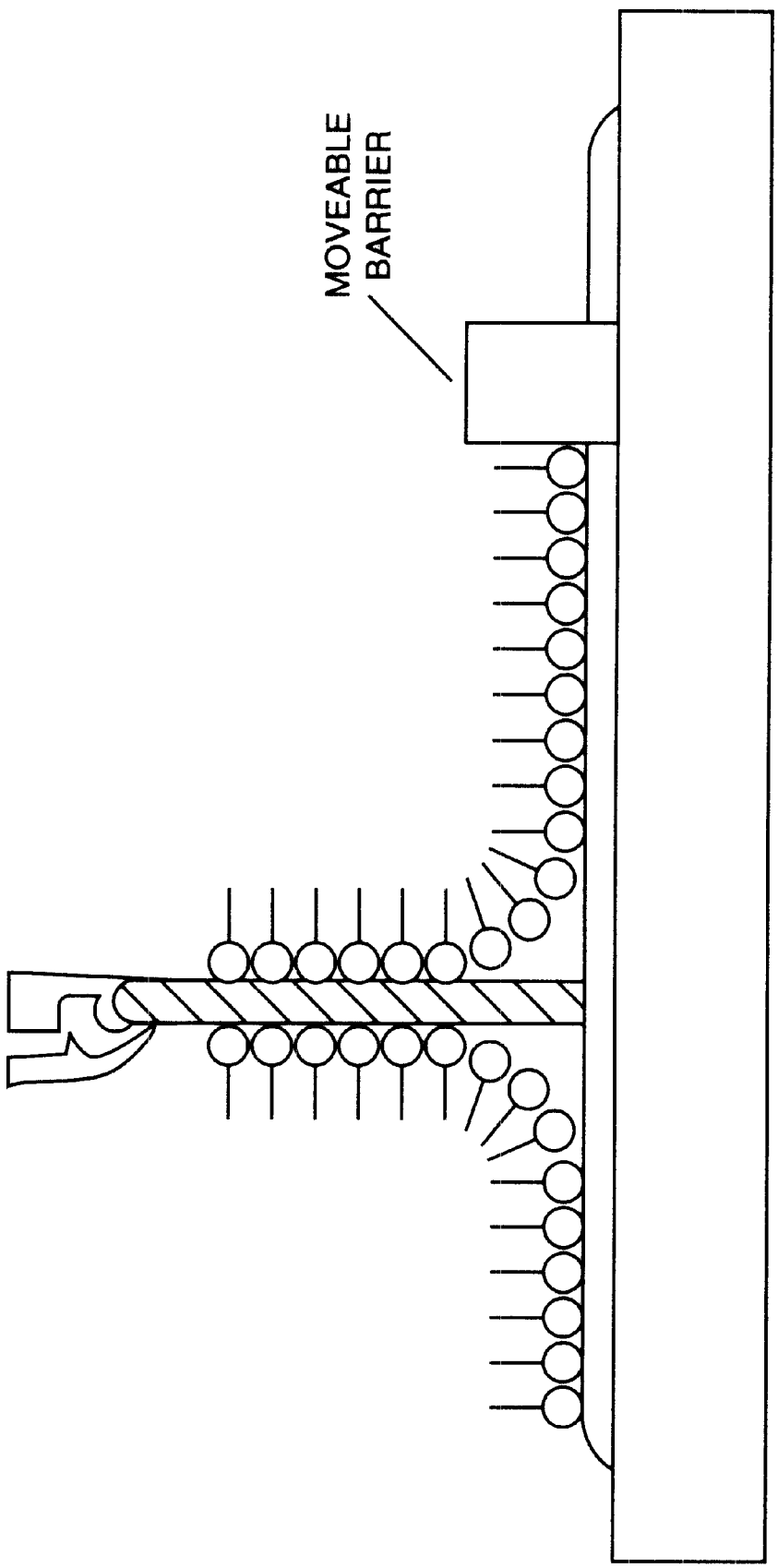
FIG. 5 shows a schematic representation of a Langmuir Blodgett apparatus where a compressed film is being transferred to a vertical plate.

Regarding the second point, polymerization requires that the lipids pack in a precise distance and orientation with respect to one another. The polymerization of polydiacetylene is therefore a "solid state" or topochemical polymerization. This is why the molecules must be closely packed to allow cross-linking. This precise packing can be controlled in monolayer and films at the air-water interface using moveable barriers of Langmuir apparatus that can compress the film to the desired packing as shown in FIG. 5, in which a compressed film is being transferred to a vertical plate. In the case of liposome formation, no such external compression is possible. The lipids assemble and occupy an equilibrium distance and orientation with respect to one another. Therefore, prior to the development of the present invention, it was not clear that the distance and packing between the molecules in the liposome material would be sufficient to allow the polymerization reaction to take place.

Figure 6:
FIG. 6 shows a micrograph of liposomes cooled only to room temperature.
Figure 7:
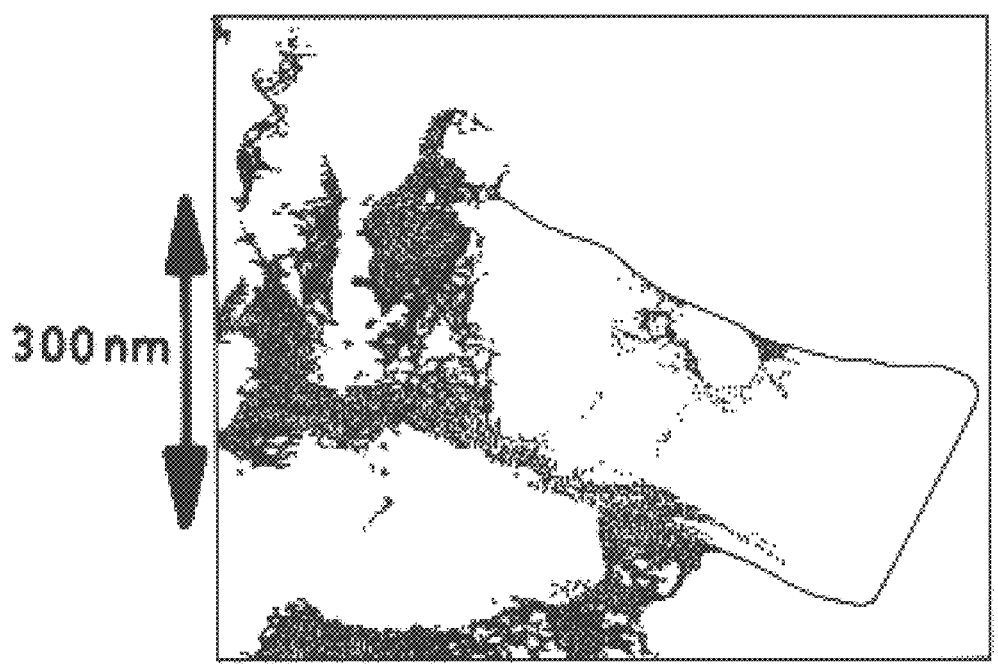
FIG. 7 shows a micrograph of liposomes prepared with cooling to 4° C.

Initially, the most difficult aspect was cross-linking the liposome diacetylenic monomeric lipids, to generate a polydiacetylene conjugated polymer (ie., polymerized liposomes). It is the conjugated polymer backbone that provides the liposomes with the desired color, and potentially allows the detection of biological analytes through an observable color change produced by the binding of the analyte to the liposomes. However, after the liposomes were formed (i.e., using the methods described above) and cooled to room temperature, it was found that they did not polymerize at all upon exposure to ultraviolet light. This was surprising because, in principle, the lipids should have crystallized and returned to their solid-like state when cooled to room temperature (i.e., once the lipids returned to this state, they should have undergone the topochemical polymerization as described above). However, they did not, as apparently the lipids were still fluid. Further analysis by transmission electron microscopy (TEM) proved that the liposomes were not crystallized. These room temperature liposomes aggregated into larger globules, characteristic of non-stabilized fluid phase liposomes as shown in the micrograph of FIG. 6. Based upon these observations, it was hypothesized that there was a hysteresis effect in the heating/cooling curve of these materials. This proved to be correct, leading to the development of "supercooling" methods. In these methods, the liposomes were cooled to 4° C., resulting in the successful crystallization of the lipids. After the cooling step was carried out, it was found that the liposomes could be polymerized, even when raised back to room temperature. Polymerization was evidenced by the blue color of the material, and the absorbance at approximately 630 nm. In contrast to the liposomes that were not supercooled, these liposomes crystallized into squares, rectangles, ellipses, or spheres that maintained their structure indefinitely, as shown in the micrograph of FIG. 7.

All of the above experimentation for production of suitable liposomes for various embodiments of the present invention (i.e., experimentation described above), is in direct contrast to the methods used to produce films. Films can be formed and polymerized at the same (i.e., ambient) temperature.

Regarding the third point, even with the polymerized liposomes, prior to the development of the present invention, it was not known whether they would exhibit color changes in response disruption of the biopolymeric membrane. For instance, it was not known whether the different lipid packing architecture of liposomes would permit the color changes observed with the film embodiments. It was only through further experimentation that optimal liposomes were developed for colorimetric detection of analytes.

C. Other Forms

In other embodiments, it is contemplated that variations in the heating and cooling rates, agitation methods, and materials of the biopolymeric material will provide other nanostructures. Such nanostructures include, but are not limited to, multilayers, braided, lamellar, helical, tubular, and fiber-like shapes, and combinations thereof. Such structures can, in some embodiments, be solvated polymers in aggregate forms such as rods and coils. For example, it has been shown that the chain length of the monomers effects the type of aggregate that forms in solution (Okahata and Kunitake, J. Am. Chem. Soc. 101: 5231 [1979]). Generation of these other forms with surfactant materials has been described for double chains (Kuo et al., Macromolecule 23: 3225 [1990]), lamellae (Rhodes et al., Langmuir 10: 267 [1994]), hollow tubules and braids (Frankel et al., J. Am. Chem. Soc. 116 [1994]). In some embodiments, colorimetric tubules were generated. As described in Example 1, tubules were prepared similarly to liposome, except that 1–10% of an organic solvent (e.g., ethanol) was added to the solution prior to sonication. The present invention also contemplates other shapes suitable for particular uses as desired.

In other embodiments, soluble polymers of polythiophenes can be generated. In some embodiments, sugar groups, peptides, or other ligands can be synthesized as thiophene derivatives and then polymerized as co-polymers. Alternately, NHS derivatives of thiophene can be polymerized and ligand groups can be attached after the polymer has formed (described below). The thiophene polymers are rendered water soluble by the addition of acid groups. Thus they can be synthesized to freely dissolve in aqueous solution, creating a colorimetric solution.

II. Self-assembling Monomers

In certain embodiments, the present invention contemplates a variety of self-assembling monomers that are suitable for formation of biopolymeric materials. Such monomers include, but are not limited to, acetylenes, diacetylenes (e.g., 5,7-docosadiynoic acid, 5,7-pentacosadiynoic acid, and 10,12-pentacosadiynoic acid), alkenes, thiophenes, polythiophenes, imides, acrylamides, methacrylates, vinylether, malic anhydride, urethanes, allylamines, siloxanes, poly-silanes, anilines, pyrroles, polyacetylenes, poly (para-phylenevinylene), poly (para-phylene), and vinylpyridinium. Lipids containing these groups can be homopolymers or mixed polymers. Furthermore, monomers with a variety of head groups are contemplated, including, but not limited to carboxylic acid, hydroxyl groups, primary amine functionalities, amino acid derivatives, and hydrophobic groups. Certain head groups may act as recognition sites for binding to analytes, allowing direct colorimetric detection, simply through exposure of the biopolymeric material to the analyte.

The biopolymeric material of the present invention may comprise a single species of self-assembling monomer (e.g., may be made entirely of 5,7-pentacosadiynoic acid) or may comprise two or more species. To produce biopolymeric material with more than one type of self-assembling monomer, solvents containing the individual monomers are combined in the desired molar ratio. This mixture is then prepared as described above (e.g., layering onto the aqueous surface of a Langmuir-Blodgett device for film preparation or evaporated and resuspended in aqueous solution for liposome preparation). In some embodiments the self-assembling monomers may be chemically linked to another molecule (e.g., a ligand).

In preferred embodiments, diacetylene monomers are used as the self-assembling monomers of the biopolymeric material of the present invention. The present invention contemplates a variety of diacetylenes including, but not limited to 5,7-docosadiynoic acid (5,7-DCDA), 5,7-pentacosadiynoic acid (5,7-PCA), and 10,12-pentacosadiynoic acid (10,12-PCA).

Figure 8:
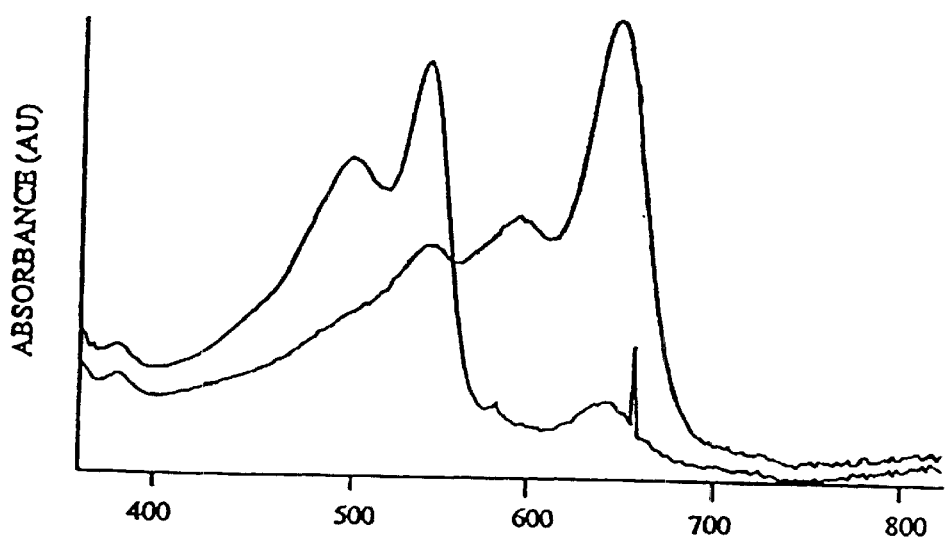
FIG. 8 shows the chemical structure of 5,7-pentacosadiynoic acid.

The presently claimed invention further contemplates the optimization of the biopolymeric material to maximize response to given reaction conditions. Although it is not necessary to understand the mechanism in order to use the present invention, and it is not intended that the present invention be so limited, it is contemplated that the chemistry of the particular lipid used in the biopolymeric material plays a critical role in increasing or decreasing the sensitivity of the colorimetric transition. For example, a positional variation of the chromophoric polymer backbone can alter sensitivity to a given analyte. This may be accomplished by moving the diacetylene group closer to the interfacial region as illustrated in FIG. 8, showing 5,7-pentacosadiynoic acid (as opposed to 10,12-pentacosadiynoic acid). Altering the placement of the polymerizable group to the 5,7- position in the monomer, dramatically improved calorimetric sensitivity in some embodiments (See e.g., Example 3). In addition, shorter or longer chain lengths of PDA were shown to have an effect on the sensitivity of the biopolymeric material for analyte detection, presumably due to changes in packing. In some analyte-detecting embodiments, such improved sensitivity allowed detection of small analytes (e.g., bacterial toxins such as cholera toxin from Vibrio cholerae and pertussis toxin, as well as antibodies). It is contemplated that further optimization will generate sensitive materials for the detection of many reactions, rearrangements, and analytes.

A. Polymerizable Group Placement in Monomer Carbon Chain

The carbon chain length that positions the head group a specific distance from the polymer backbone in the final polymerized material is dependent on the position of the polymerizable group in an unassembled monomer. In the case of diacetylene liposomes, it has been shown that a diacetylene group positioned from between the 18–20 positions to the 3–5 position in the monomers produced progressively more sensitive liposomes when used for the detection of analytes. Liposomes produced from monomers with the diacetylene groups from the 10–12 position to the 4–6 position provides particularly efficient control of sensitivity. Diacetylene groups positioned in about the 5–7 position are preferred for certain embodiments, such as cholera toxin detection. The production protocol for the monomer determines at which position the diacetylene group will be placed in the final monomer product.

B. Total Carbon Chain Length

The total carbon chain length in the unassembled monomer also influences the level of sensitivity of the liposome product, although to a lesser extent than the position of the polymerizable group in the monomer carbon chain. The shorter chain length typically provides for greater sensitivity for, as determined in analyte-detecting embodiments. The monomers that are ideally useful in construction of the inventive colorimetric liposomes can range from between $C_{12}$ to $C_{25}$ in length, although both longer and shorter chain lengths are contemplated by the presently claimed invention. A preferred range of monomer carbon chain length in the present invention is $C_{20}$ to $C_{23}$.

The influence of monomer chain lengths and positioning of the polymerizable group on the chain has been demonstrated in several experiments. It was shown that in the case of 10,12-diacetylene derivative, $C_{23}$ chains provided a final colorimetric liposomes product that changed color at a lower analyte level than those produced from monomers with a $C_{25}$ chain. In the case of 5,7-diacetylene derivatives, the $C_{22}$ length chain provided a greater sensitivity than the $C_{24}$ length chain. Thus, the chain length is designed so as to be suitable for the optimal detection conditions of interest.

III. Dopants

The biopolymeric materials of the present invention may further comprise one or more dopant materials. Dopants are included to alter and optimize desire properties of the biopolymeric materials. Such properties include, but are not limited to, colorimetric response, color, sensitivity, durability, robustness, amenability to immobilization, temperature sensitivity, and pH sensitivity. Dopant materials include, but are not limited to, lipids, cholesterols, steroids, ergosterols, polyethylene glycols, proteins, peptides, or any other molecule (e.g., surfactants, polysorbate, octoxynol, sodium dodecyl sulfate, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cerebroside, lysophosphatidylcholine, D-erythroshingosine, sphingomyelin, dodecyl phosphocholine, N-biotinyl phosphatidylethanolamine, and other synthetic or natural components of cell membranes) that can be associated with a membrane (e.g., liposomes and films). For example, the embodiments provided in Example 4 demonstrate that the addition of sialic acid-derived diacetylene monomers to liposomes comprising ganglioside and PDA provided a dramatic increase in colorimetric sensitivity and quantifiability to the detection of low levels of analyte. This improvement in colorimetric response using dopant is extremely beneficial when un-doped materials produce only weak signals. Such is often the case when the target lipids (e.g., lipids that contain the ligand or that are the substrate of an enzymatic reaction) are not covalently linked to the polymer backbone (e.g., ganglioside ligands).

In some embodiments, dopants are added to alter the color of the biopolymeric material. For example, the present invention provides liposomes that change from blue to red, but also blue to orange, purple to red, purple to orange, green to red, and green to orange. For example, glutamine derivatized PDA produced very dark blue (ie., almost black) liposomes. In other embodiments, green liposomes were produced with cycles of annealing (i.e., heating to approximately 80° C.) and cooling (i.e., to ambient temperatures) prior to polymerization. The advantage with the multi-color approach is that sensors can be made where a specific reaction turns the material a specific color.

Different dopant materials can be combined in a single biopolymeric material preparation. For example, the present invention provides a dopant cocktail that is a mix of glucose and sialic acid-derived polydiacetylene. The glucose component of the dopant mixture appears to act primarily to prevent non-specific adhesion to the surface of the inventive liposome and may also enhance sensitivity. The polydiacetylene bound sialic acid component appears to functionally destabilize the surface to provide a dramatic increase in sensitivity for analyte detection. By using this co-dopant approach, both specificity of adhesion and sensitivity can be optimized, without unduly compromising the structural integrity of the biopolymeric material.

Although it is not necessary to understand the mechanism in order to use the present invention, and it is not intended that the present invention be so limited, it is contemplated that the addition of dopant lowers the activation barrier of the chromatic transition and/or provides a connection between the ligands (i.e., if ligands are present) and the conjugated backbone, enabling the reactions to induce the calorimetric transition. One theory elucidated during the development of the present invention is that dopants with bulky headgroups (e.g., sialic acid-derived lipid monomers) are subject to various solvent interactions at the matrix surface, destabilizing the structure of the blue film and thus allowing relatively small perturbations provided by the localized membrane rearrangements to complete the colorimetric transition. Another possible explanation for the improved calorimetric response observed using dopants with bulky headgroups is that the stearic effects induced by the molecular recognition event (i.e., the interaction of an analyte or other molecule with the biopolymeric material) may interfere with the headgroups of the dopants, thus propagating the perturbation caused by the analyte.

In certain embodiments, the dopant comprises a diacetylene or a modified diacetylene (e.g., sialic acid derived diacetylene). It should be noted that in this case, the derivatized lipid is used to modify the properties of the biopolymeric material and is not used as a molecular recognition site for an analyte detection (e.g., as in the case of sialic acid ligand used to detect influenza virus). For example, a diacetylene-based polymeric material containing only sialic acid derivatized monomer or lactose derivatized monomer did not respond to neurotoxins (e.g., botulinum neurotoxin), indicating that there was an insufficient interaction between the neurotoxins and the derivatized diacetylene lipid to induce the color change. However, when the same material was provided with a ligand having affinity for neurotoxin (e.g., ganglioside $G_{M1}$ a colorimetric response was detected in the presence of neurotoxin. In this example, the sialic acid and lactose derived lipids are "dopants" and the ganglioside $G_{M1}$ is a ligand.

It is contemplated that a wide variety of dopant materials will find use in optimizing the properties of the biopolymeric material used in various embodiments of the present invention. Materials that are constituents of cell membrane structures in nature are generally useful as dopants in the present invention. For instance, steroids (e.g., cholesterols) represent potential dopants that can provide desired degrees of destabilization or stabilization to the biopolymeric material. Surfactant type compounds also may serve as dopants, whether or not they are polymerized to self-assembling monomers that make up the polymer back bone. For example, the detergent TWEEN 20, which does not contain a polymerizable group, has been shown to provide a very dramatic intensity to the blue color of the liposomes of certain embodiments of the present invention. An alternative surfactant that can be used as dopants are peptide-detergents (i.e., small amphipathic molecules that have a hydrophobic region mimicking the membrane spanning regions of membrane proteins). These small peptides (typically 20–25 amino acids in length) can be incorporated into the biopolymeric material to alter the stability or sensitivity of the calorimetric response of the material. Since peptide-detergents are bulkier in the hydrophobic region of the material, they are capable of producing a more pronounced effect on film stability or sensitivity than many other surfactant molecules.

The most appropriate percentage of dopant incorporated into the structure of the biopolymeric material is dependent on the particular system being developed, and the needs of the testing situation. For instance, sensitivity may be compromised to some extent in the favor of long shelf life, or to accommodate rigorous field conditions. The acceptable percentage of dopant is theoretically limited only to that which will not preclude sufficient incorporation of the indicator polydiacetylene molecules to produce the necessary optical density and color change or to that which will disrupt the stability of the polymeric structures.

Molar percentages of dopant can vary from as low as 0.01% where increases of sensitivity have been observed in certain embodiments, to as high as 75%, after which the structural integrity of the biopolymeric material typically begins to deteriorate. However, there may be specific embodiments where the percentage of dopant is greater than 75% or lower than 0.01%. A preferred range for dopant is 2%–10%. In certain embodiments of the present invention, the optimal percentage of dopant is about 5% (See e.g., Example 4, section II). For example, for the detection of cholera toxin, it was found that a film comprising 2% lactose-derivatized polydiacetylene (PDA), 5% ganglioside, and 93% PDA resulted in a strong blue to red color change when the film was incubated with the analyte.

In selecting appropriate incorporation methods for the dopant, there are several competing considerations. For example, for the sonication bath method for production of certain liposome embodiments, the incorporation is very controlled, and requires several hours of processing. This relatively slow, gentle incorporation method allows the incorporation of comparatively large or complex dopant materials. However, the sonication bath approach is only suitable when it is intended that a relatively low percentage of dopant is to be incorporated. The point probe method allows the incorporation of a much higher percentage of dopant material over a shorter period of time, typically from one to ten minutes. However, this method is typically limited to incorporation of small to intermediate sized dopant materials. The temperature chosen for incorporation are selected based on the particular analytical system and liposome parameters desired. A practitioner will be able to select parameters such as pH, choice of dilutents, and other factors based on the particular system and desired characteristics of the biopolymeric material.

A series of derivatized polydiacetylene dopant molecules have been synthesized with a wide range of physical characteristics. These dopants are not the same as filler molecules typically observed in biological membranes (i.e., cholesterol, proteins, lipids, detergents). They differ in that they provide unique and specific functionality to a given sensor system. The design of several dopants that provide specific functionality to the non-synthetic embodiments are described below and in Example 4.

Figure 9:
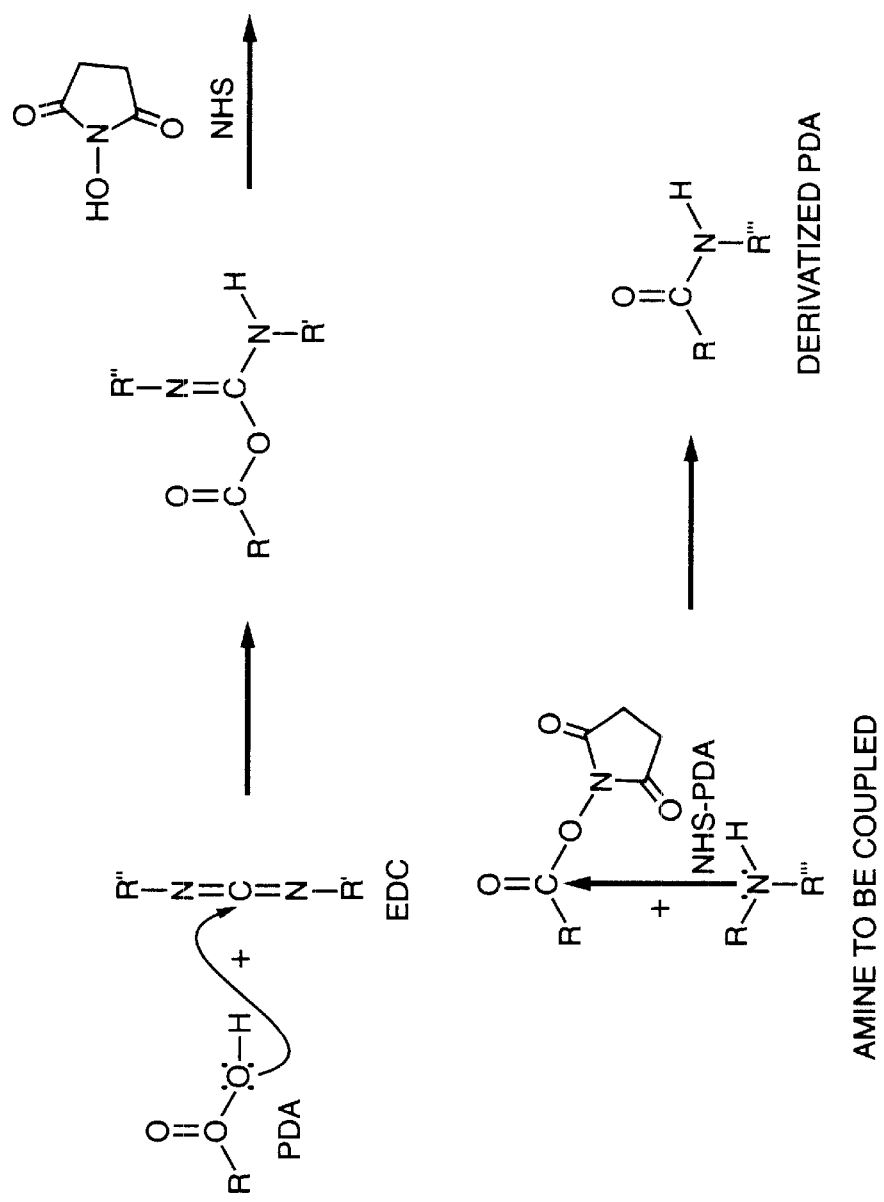
FIG. 9 shows a synthesis reaction for modifying the free amino group of a molecule for coupling to a lipid monomer.
Figure 10A:
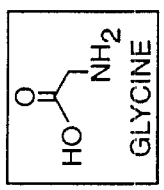
FIG. 10 shows the properties of biopolymeric materials composed of amino acid-derivated diacetylene monomers.
Figure 10A:
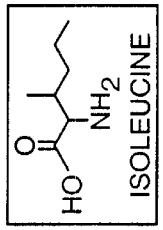
Figure 10A:
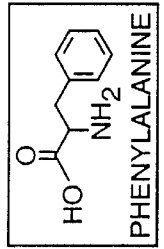
Figure 10A:
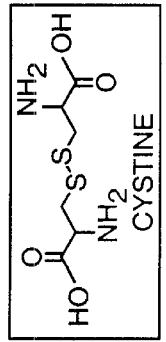
Figure 10A:
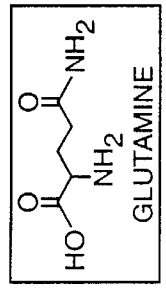

A simple system has been designed so that the PDA molecule can easily be derivatized. The synthesis is shown in FIG. 9. Here, 10,12-pentacosadiynoic acid is modified to amine-couple to any molecule with a free amino group. Since all amino acids have a free amino group (lysine has 2 free amino groups), the 20 amino acids were each placed on the head of PDA molecules. Each one of the derivatized PDA molecules has special properties that allow special functionality to be incorporated into the biopolymeric material. For example, glutamine-PDA doped materials were the most sensitive, most water soluble, and most consistent colorimetric sensors. The properties of some of the other amino acid-derivated PDA molecules are described in Example 4. The water solubility, ability to form films and liposomes, color, and colorimetric response for representative amino acid-derived diacetylenes is shown in FIG. 10.

IV. Ligands

The biopolymeric materials of the present invention may further comprise one or more ligands. Ligands can act as the recognition site in the biopolymeric materials for analytes or as anchors for recruiting molecules or localizing reactions to the biopolymeric surface. In some embodiments, upon the interaction of the analyte with the ligand or ligands, a disruption of the polymer backbone of the biopolymeric material occurs, resulting in a detectable color transition. For the detection of lipid cleavage reactions, it may be desired to identify the presence of a particular cleavage means (i.e., analyte) through such a colorimetric change. In some embodiments, biopolymeric material comprising a ligand (e.g., an antibody for a particular lipase) for the cleavage means can be placed in a device next to biopolymeric material that detects the cleavage means reaction itself (described below). In this manner, both the presence and the activity of the cleavage means are detected in a single device.

Figure 11:
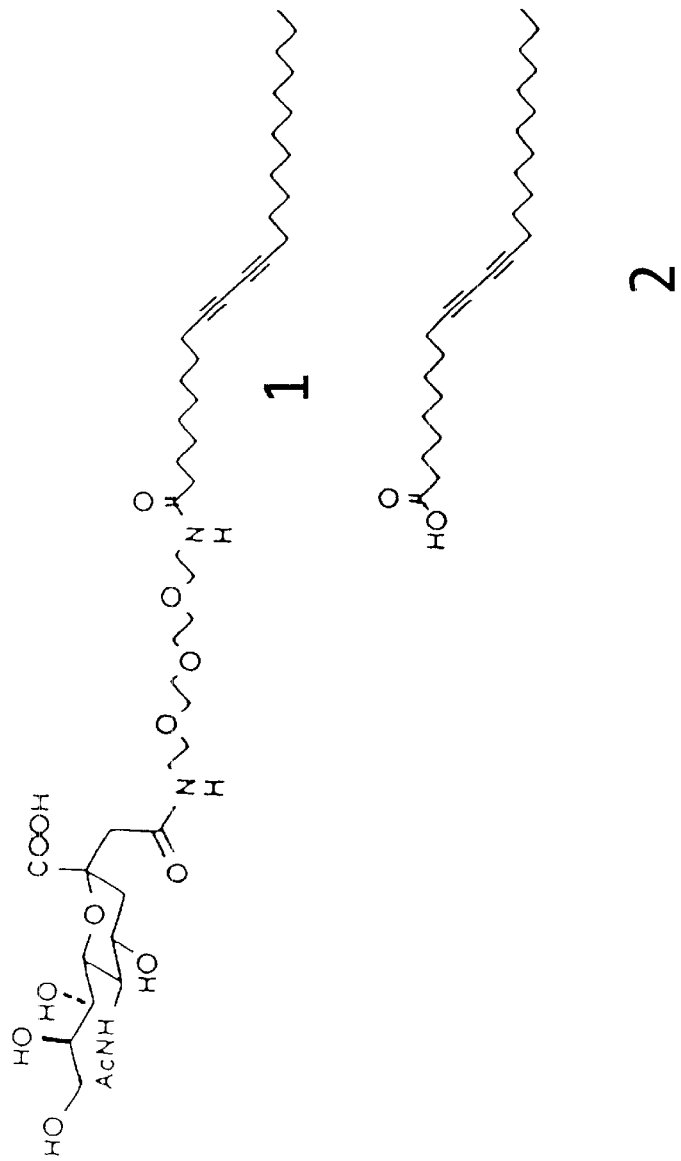
FIG. 11 shows the chemical structure of sialic acid derived 10,12-pentacosadiynoic acid (compound 1) and 10,12-pentacosadiynoic acid (compound 2).

Ligands can be linked by a linking arm to the self-assembling monomers, directly linked to the monomers, incorporated into the biopolymeric matrix prior to or during the polymerization process, or attached to the matrix following polymerization (e.g., by linking ligands to matrix constituents that contain head groups that bind to the ligands or through other means). For example, FIG. 11 provides a schematic depiction of one embodiment of the present invention. Compound 1 shows a receptor-binding ligand (i.e., sialic acid) attached to one terminal end of a spacer molecule. The second terminal end of the spacer molecule is attached to one of several monomers (e.g., 10,12-pentacosadiynoic acid) that have been polymerized so as to form a chromatic detection element. Compound 2 shows the 10,12-pentacosadiynoic acid without an attached ligand.

The ligand group of the present invention can be comprised of a wide variety of materials. The main criterion is that the ligand have an affinity for the analyte of choice. Appropriate ligands include, but are not limited to, peptides, carbohydrates, nucleic acids, biotin, drugs, chromophores, antigens, chelating compounds, short peptides, pepstatin, Diels-Alder reagents, molecular recognition complexes, ionic groups, polymerizable groups, dinitrophenols, linker groups, electron donor or acceptor groups, hydrophobic groups, hydrophilic groups, antibodies, or any organic molecules that bind to receptors. The biopolymeric material can be composed of combinations of ligand-linked and unlinked monomers to optimize the desired colorimetric response (e.g., 5% ligand-linked dicosadynoic acid [DCDA] and 95% DCDA). Additionally, multiple ligands can be incorporated into a single biopolymeric matrix. As is clear from the broad range of ligands that can be used with the present invention, an extremely diverse group of analytes can be detected.

In some embodiments, the self-assembling monomers are not associated with ligands, but are directly assembled, polymerized, and used as colorimetric sensors. Such biopolymeric materials can find use in the detection of certain classes of analytes including, but not limited to, volatile organic compounds (VOCs).

In some embodiments, ligands are incorporated to detect a variety of pathogenic organisms including, but not limited to, sialic acid to detect HIV (Wies et al., Nature 333: 426 [1988]), influenza (White et al., Cell 56: 725 [1989]), Chlamydia (Infect. Imm. 57: 2378 [1989]), *Neisseria meningitidis, Streptococcus suis*, Salmonella, mumps, newcastle, and various viruses, including reovirus, Sendai virus, and myxovirus; and 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect reovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpes virus (Kaner et al., Science 248: 1410 [1990]); oligomannose to detect *Escherichia coli*; ganglioside $G_{M1}$ to detect *Neisseria meningitidis*; and antibodies to detect a broad variety of pathogens (e.g., *Neisseria gonorrhoeae, V. vulnificus, V. parahaemolyticus, V. cholerae*, and *V. alginolyticus*).

One skilled in the art will be able to associate a wide variety of ligand types with the biopolymeric materials of the present invention. Methods of derivatizing lipids with a diverse range of compounds (e.g., carbohydrates, proteins, nucleic acids, and other chemical groups) are well known in the art. The carboxylic acid on the terminal end of lipids can be easily modified to form esters, phosphate esters, amino groups, ammoniums, hydrazines, polyethylene oxides, amides, and many other compounds. These chemical groups provide linking groups for carbohydrates, proteins, nucleic acids, and other chemical groups (e.g., carboxylic acids can be directly linked to proteins by making the activated ester, followed by reaction to free amine groups on a protein to form an amide linkage). Examples of antibodies attached to Langmuir films are known in the art (See e.g., Tronin et al., Langmuir 11: 385 [1995]; and Vikholm et al., Langmuir 12: 3276 [1996]). There are numerous other means to couple materials to membranes, or incorporate materials within a membrane, including for example, coupling of proteins or nucleic acids to polymer membranes (See e.g., Bamford et al. Adv. Mat. 6: 550 [1994]); coupling of proteins to self-assembled organic monolayers (See e.g., Wilmer et al., Adv. Mat. 5: 912 [1993]), and incorporating proteins into membranes (See e.g., Downer et al., Biosensor and Bioelect. 7: 429 [1992]); among others. Protocols for attaching ligands (e.g., proteins, nucleic acids, and carbohydrates) to the colorimetric materials of the present invention are demonstrated in Example 5.

For example, the methods of the present invention provide a system to easily attach protein molecules, including antibodies, to the surface of polydiacetylene thin films and liposomes, thereby providing biopolymeric materials with "protein" ligands. Such ligands include, but are not limited to, peptides, proteins, lipoproteins, glycoproteins, enzymes, receptors, channels, and antibodies. Upon binding an analyte (e.g., enzyme substrate, receptor ligand, antigen, and other protein), a disruption of the polymer backbone of the biopolymeric material may occur, resulting in a detectable color change. The present invention contemplates protein ligands that are incorporated into the biopolymeric material and those chemically associated with the surface of the biopolymeric material (e.g., chemically linked to the surface head group of a monomer in the biopolymeric monomer).

V. Detection of Colorimetric Changes

The colorimetric change resulting from disruption of the biopolymeric material can be detected using many methods. In preferred embodiments of the presently claimed invention, a color shift was observed simply by visual observation. Thus, the present invention may be easily used by an untrained observer such as an at-home user.

In alternative embodiments, spectral test equipment well known in the art is employed to detect changes in spectral qualities beyond the limits of simple visual observation, including optical density to a particular illuminating light wavelength. For example, using a spectrometer, the spectrum of the material was measured before and after analyte introduction, and the colorimetric response (%CR) was measured. The visible absorption spectrum of the material prior to analyte exposure was measured as $B_o = I_x(I_y + I_x)$ where "B" represents the percentage of a given color phase at wavelength $I_x$ compared to a reference wavelength $I_y$. The spectrum was then taken following analyte exposure and a similar calculation was made to determine the $B_{final}$. The colorimetric response was calculated as %CR=$[(B_o - B_{final})/B_o] \times 100\%$.

Additionally, the presently claimed invention can be, if desired, attached to a transducer device. The association of self-assembled monomer materials with transducers has been described using optical fibers (See e.g., Beswick and Pitt, J. Colloid Interface Sci. 124: 146 [1988]; and Zhao and Reichert, Langmuir 8: 2785 [1992]), quartz oscillators (See e.g., Furuki and Pu, Thin Solid Films 210: 471 [1992]; and Kepley et al., Anal. Chem. 64: 3191 [1992]), and electrode surfaces (See e.g., Miyasaka et al., Chem. Lett., p. 627 [1990]; and Bilewicz and Majda, Langmuir 7: 2794 [1991]). However, unlike these examples, the present invention provides a double-check (i.e., confirmation method) by observation of color change in the material.

In some embodiments, the biopolymeric materials of the present invention can be coated on thin PzT materials that oscillate at a resonance frequency, producing a microelectromechanical system (MEMS system). Thus, alterations in the biopolymeric material can be detected as a change in resonant frequency with calorimetric change providing a confirmation of event.

Sensitivity can also be enhanced by coupling the lipid-polymer to a photoelectric device, colorimeter, or fiber optic tip that can read at two or more specific wavelengths. Also, the device can be linked to an alternative signalling device such as a sounding alarm or vibration to provide simple interpretation of the signal.

As described above, in addition to detecting the activity of analytes (e.g., lipid cleavage activity of lipases and membrane modification activity of transferases), it may also be desired to detect the presence of analytes. The biopolymeric materials of the presently claimed invention can be used to detect a large variety of analytes including, but not limited to, small molecules, microorganisms, membrane receptors, membrane fragments, volatile organic compounds (VOCs), enzymes, drugs, antibodies, and other relevant materials by the observation of color changes that occur upon analyte binding. The presently claimed invention works under very mild testing conditions, providing the ability to detect small biomolecules in a near natural state and avoiding the risks associated with modification or degradation of the analyte.

VI. Detection of Membrane Conformational Changes

As described above, the presently claimed invention provides methods for detecting conformational alterations in the biopolymeric material by observation of calorimetric changes. Such conformational changes can be caused by the binding of an analyte to a ligand (described above) and through the chemical modification of the biopolymeric material by chemical reactions (e.g., enzymatic catalysis).

In some embodiments, the presently claimed invention provides a simple protocol using biopolymeric material and offers a practical approach to detecting interfacial catalysis, identifying inhibitors, and screening enzymes and other catalytic entities (e.g., catalytic antibodies) to characterize their catalytic capabilities. These methods use natural, unlabeled substrates, and catalysis or inhibition is signaled by the presence or lack of a color transition of the surrounding lipid-polymer assembly. The one-step nature of the technique allows for convenient adaptation to high throughput compound screening. This method is generally applicable to factors that affect enzyme recognition and activity, and influence membrane reorganization.

Polymerized mixed vesicles are highly stable against chemical and physical degradation and offer a convenient, economical alternative to enzymatic assays that employ radiolabled substrates. The vesicle stock solutions described by the present invention have been stored for over six months without affecting the results of the assay.

Specific applications of the presently claimed invention are described below to illustrate the broad applicability of the invention to a range of conformational changes and to demonstrate its specificity, and ease of use. Phospholipase $A_2$, phospholipase C, phospholipase D, bungarotoxin, and other enzyme activities are illustrated. These examples are intended to merely illustrate the broad applicability of the present invention; it is not intended that the present invention be limited to these particular embodiments.

I. Phospholipase $A_2$ Activity $PLA_2$ activity has previously been studied in a variety of model membrane systems such as polymerized vesicles (Dua et al., J. Biol. Chem. 270, 263 [1995]), micelles (Reynolds et al. supra), and monolayers (Grainger et al, supra; and Mirsky et al., Thin Solid Films 284, 939 [1996]) using labeling techniques (e.g., radioactivity and fluorescence). The presently claimed invention provides biopolymeric materials incorporating $PLA_2$ substrate lipids for the calorimetric detection of $PLA_2$ enzyme activity.

Figure 12A:
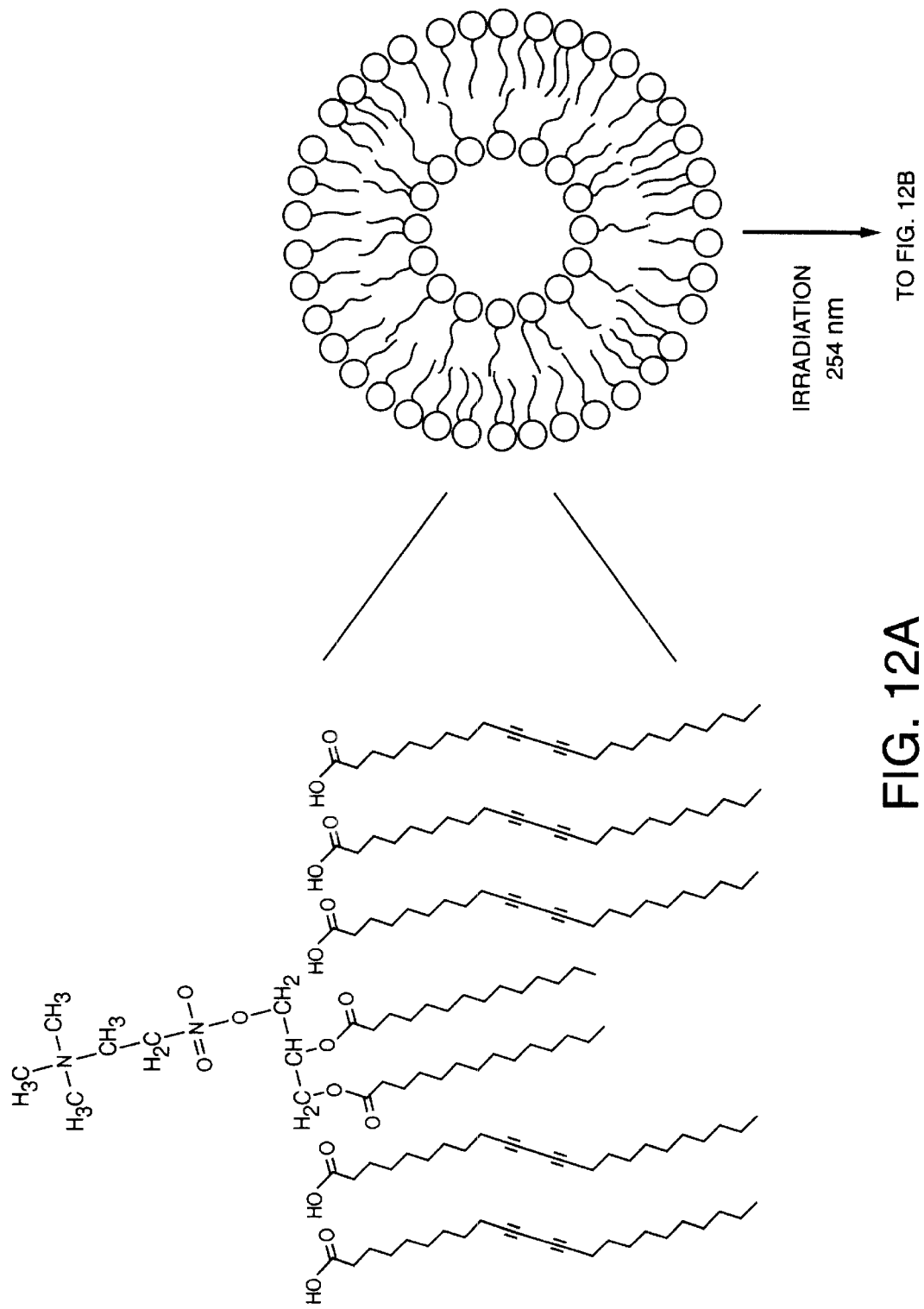
FIG. 12 shows substrate lipid (i.e., DMPC) in a diacetylenic lipid matrix before (top) and after (bottom) polymerization.
Figure 12B:
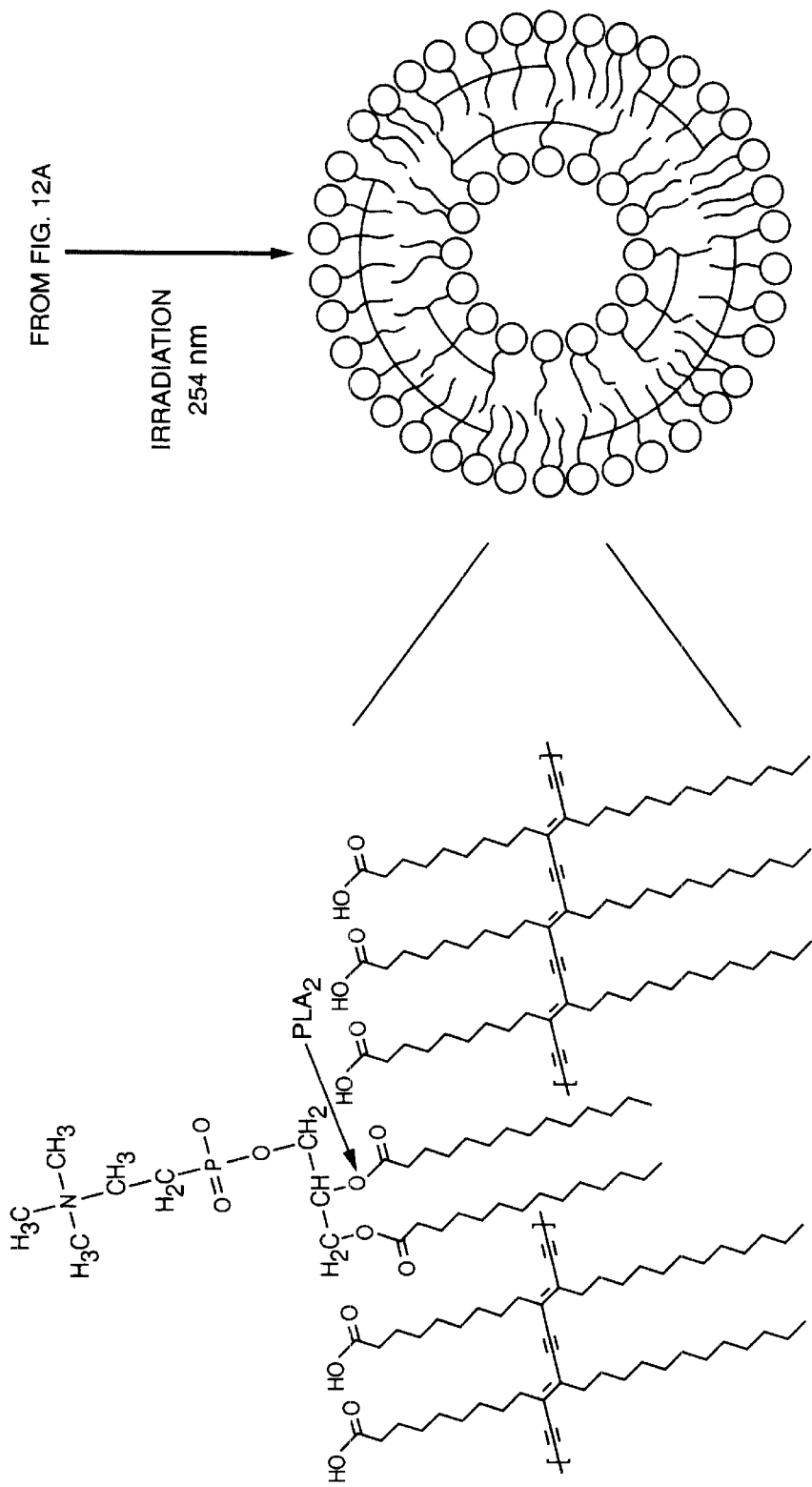
Figure 13:
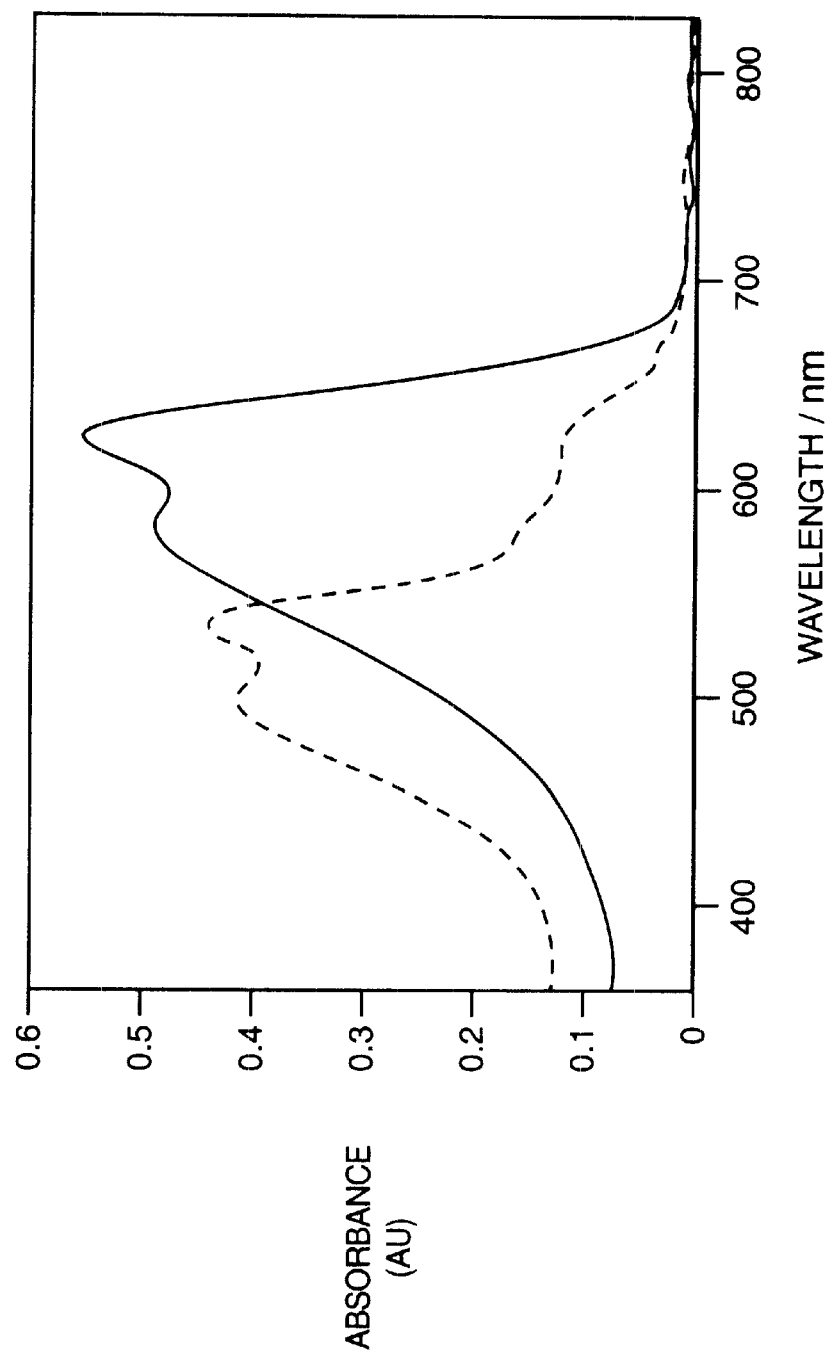
FIG. 13 shows the visible absorption spectrum of the liposomes of FIG. 12 before (solid line) and after (dashed line) exposure to phospholipase $A_2$.

Biopolymeric materials were prepared with a combination of polymerizable matrix lipid (e.g., 10,12-tricosadiynoic acid) and various mole fractions (0–40%) of $PLA_2$ substrate lipid (e.g., dimyristoylphosphatidylcholine [DMPC]) as described in Examples 1 and 10. In some embodiments, the biopolymeric materials containing the $PLA_2$ substrate lipid were liposomes as shown in FIG. 12. This figure shows DMPC substrate in a diacetylenic lipid matrix before (top) and after (bottom) polymerization. In their initial state, the vesicles appeared deep blue to the naked eye and absorbed maximally at around 620 nm, as shown in FIG. 13 (solid line). Upon addition of $PLA_2$ to the DMPC/PDA vesicles, the suspension rapidly turned red (i.e., within minutes) and exhibited a maximum absorption at approximately 540 nm as shown in FIG. 13 (dashed line).

Figure 14:
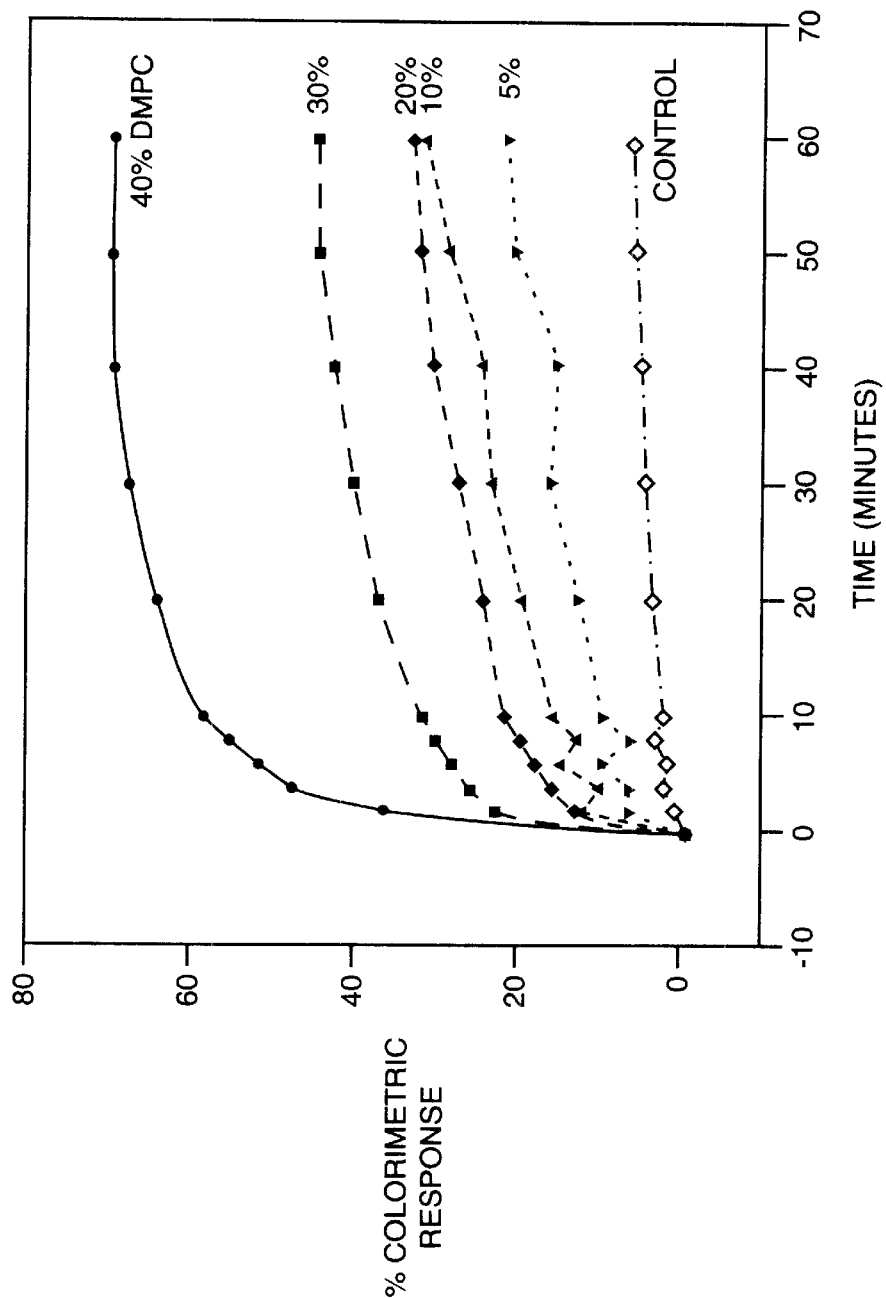
FIG. 14 shows the change in colorimetric response of the liposomes of FIG. 12 with varying concentrations of DMPC in response to phospholipase $A_2$ exposure.

The color change was modulated by altering the mole percentage of the natural lipid DMPC in the PDA vesicle as shown in FIG. 14. A relative color change of 10% or more is clearly observed with the naked eye. Within minutes, liposomes containing greater than 20% DMPC exhibited strong colorimetric responses. Liposomes with low molar ratios of DMPC (e.g., 5%) also showed visually detectable calorimetric response after longer incubations. Vesicles that did not contain DMPC, remained largely in their blue phase upon addition of $PLA_2$ as shown in the control sample.

Biochromic transitions of PDA vesicles and films have been proposed to arise from perturbation of the extended $\pi$-overlap of the conjugated polymer backbone. This structural rearrangement, induced in previous studies by multivalent receptor binding or penetration of peptide domains into the PDA matrix, results in absorption at shorter wavelengths, (i.e., 490–540 nm) (Charych et al., Chemistry and Biology, supra; Pan and Charych, supra; and Cheng and Stevens, Advance Materials, supra). The intense color change observed upon the interaction between the enzyme $PLA_2$ and the mixed DMPC/PDA vesicles indicates, that in this case, chemical modification of the vesicles by interfacial catalysis provides an alternative pathway for inducing the biochromatic transitions. Thus, the presently claimed invention demonstrates a new means of inducing colorimetric change in biopolymeric materials.

Figure 15:
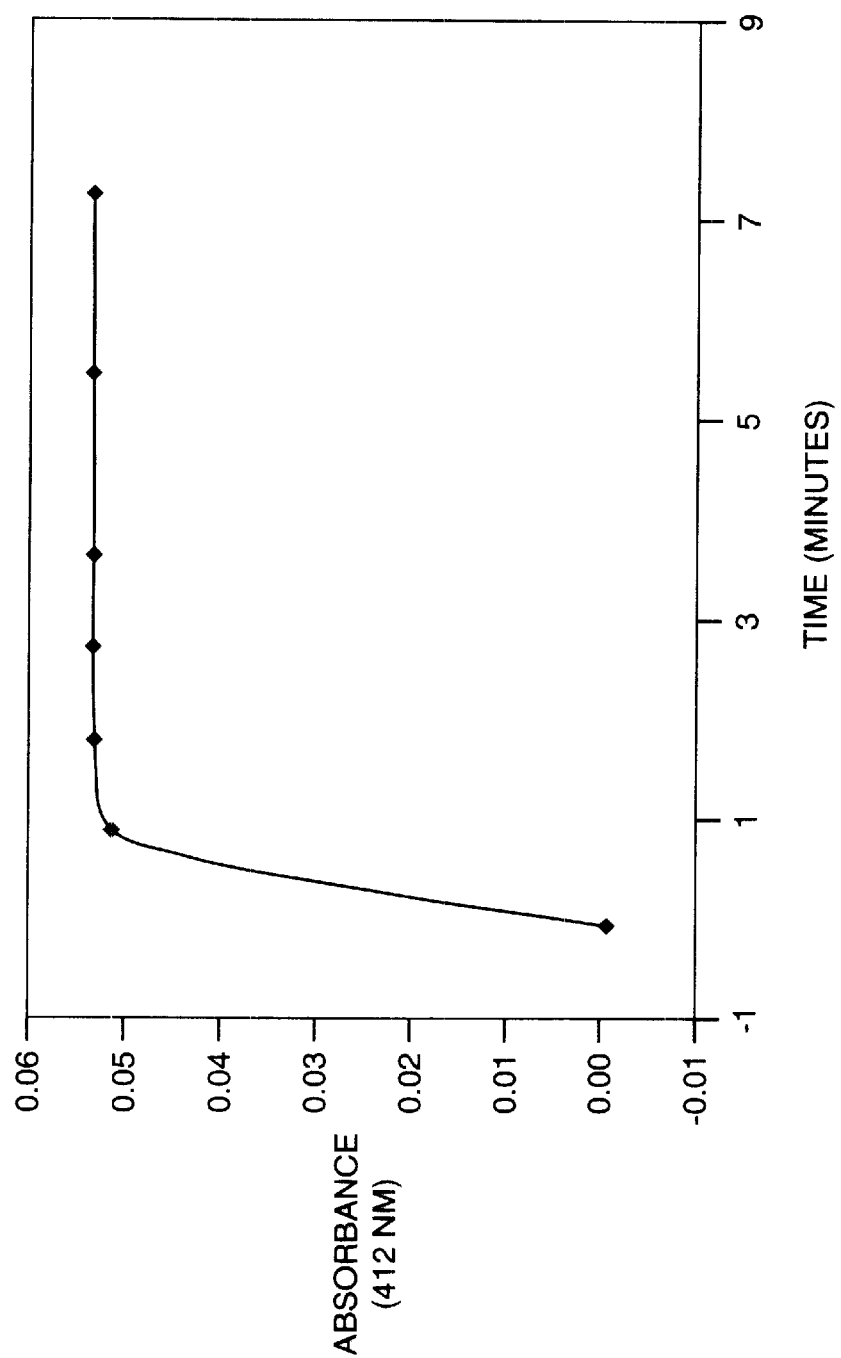
FIG. 15 shows the absorbance at 412 nm of liposomes containing 1,2-bis-(S-decanoyl)-1,2-dithio-sn-glycero-3-phosphocholine (DTPC) following exposure to $PLA_2$ for various lengths of time.

In order to confirm that biocatalysis was occurring at the DMPC/PDA vesicles, $PLA_2$ activity was independently measured using a labeled lipid analog incorporated into the PDA matrix, allowing simultaneous measurement of product formation and colorimetric response of the vesicles. The analog used was thioester 1,2-bis-(S-decanoyl)-1,2-dithio-sn-glycero-3-phosphocholine (DTPC). Cleavage of DTPC by $PLA_2$ produces a soluble thiol-modified lipid that readily reacts with 5,5'-dithiobis-2-nitrobenzoic acid (DTNB) to produce a colored product that characteristically absorbs at 412 nm (Reynolds et al., supra). Indeed, when $PLA_2$ was added to mixed 40% DTPC/PDA vesicles, the hydrolysis products reacting with DTNB gave rise to a significant absorption at 412 nm as shown in FIG. 15. At the same time, the PDA vesicles also changed color, and the suspension exhibited a colorimetric response similar to that of the vesicles containing DMPC shown in FIG. 13. These results confirm that interfacial catalysis by $PLA_2$ occurred at the polymerized mixed vesicles.

Figure 16B:
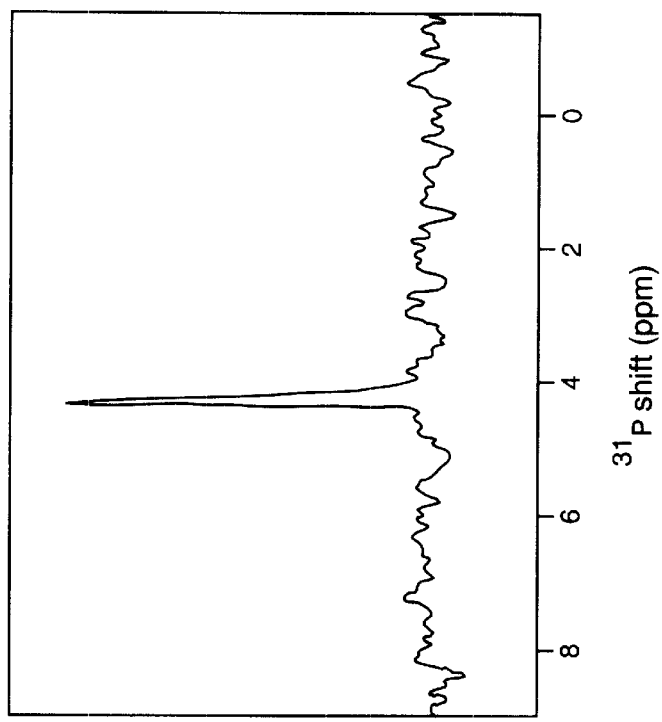
FIGS. 16A and 16B shows $^{31}P$ NMR spectra of the DMPC/PDA vesicles prior to the addition of $PLA_2$ (A), and following the enzymatic reaction (B).
Figure 16A:
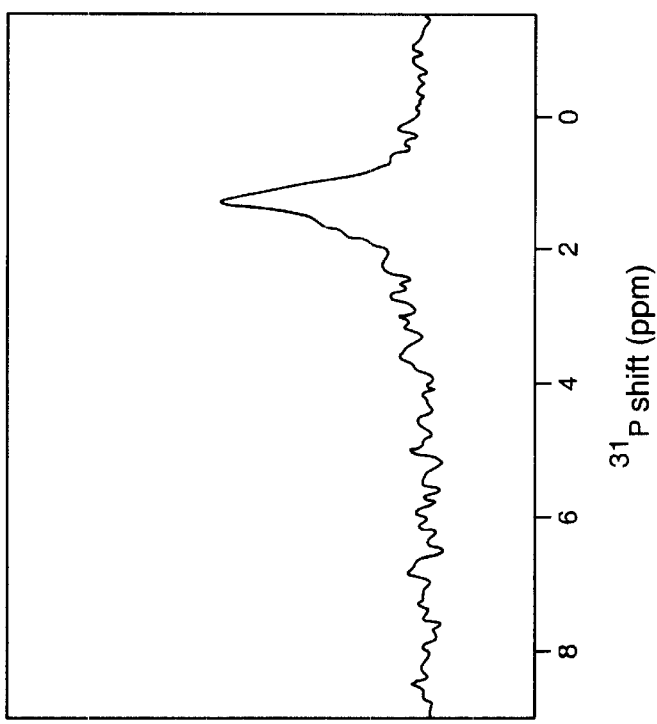

NMR experiments further verified the occurrence of interfacial catalysis by $PLA_2$, and provided information of the fate of the enzymatic reaction products. FIG. 16 features $^{31}P$ NMR spectra of the DMPC/PDA vesicles prior to the addition of $PLA_2$ (FIG. 16A), and following the enzymatic reaction (FIG. 16B). The relatively broad, anisotropic $^{31}P$ resonance from the intact vesicles, FIG. 16A, corresponds to the choline head-group of DMPC embedded in the PDA vesicles. The observation of $^{31}P$ anisotropy in FIG. 16A indicates that DMPC molecules are immobilized within the vesicle matrix. After addition of $PLA_2$, the $^{31}P$ signal was shifted downfield as shown in FIG. 16B. The position of the $^{31}P$ resonance in FIG. 16B coincides with the shift observed for the water-solubilized lyso-myristoylphosphatidylcholine, the hydrolysis product of DMPC. Furthermore, FIG. 16B shows that the $^{31}P$ resonance observed in the suspension of the enzyme-treated vesicles becomes significantly narrower than the $^{31}P$ signal from the initial DMPC/PDA vesicle, FIG. 16A, indicating a higher mobility of the phosphate group following $PLA_2$ catalysis (Smith and Ekiel, Phosphorous-31 NMR, Principles and Applications, Academic Press, Orlando, pp 447 [1984]).

This result suggests dissolution of the lysolipid reaction products following the enzymatic reaction. $^1H$ NMR data indicating the appearance of a distinct lysolipid phase following the reaction with $PLA_2$ further supported this description.

II. Others Phospholipases

Colorimetric detection of interfacial catalysis by other enzymes such as phospholipase C (PLC) and phospholipase D (PLD) has been also achieved using the substrate-modified PDA vesicles, demonstrating that the methodology described by the present invention is generally applicable. These phospholipases cleave the polar head group region of glycerophospholipids, whereas phospholipase $A_2$ cleaves the acyl ester bond exclusively at the 2-acyl position.

The assay test for phospholipase D and C were run under similar conditions as the $PLA_2$ assays. Both PLD and PLC activity were successfully detected by the liposomes assay. The PLD assay yielded a final colorimetric response of approximately 55%. However, the shape of the response curve was more gradual than that of $PLA_2$. Although it is not necessary to understand the mechanism in order to use the present invention, and it is not intended that the present invention be so limited, it is contemplated that either the kinetics of the PLD-catalyzed reaction are different or that the response time between the catalytic event and the color change is slower. The PLC assay yielded a final colorimetric response of 60% and the response curve was similar to that of $PLA_2$. NMR experiments further verified the occurrence of interfacial catalysis by PLC and PLD.

III. Bungarotoxin (BUTX)

$\beta$-bungarotoxin, a snake toxin from *Bungarus multicinctus*, is known to destroy synaptic vesicles and inhibit acetylcholine release. It is classified as a $PLA_2$ toxin and is composed of two subunits: a 12-kDa subunit that exhibits $PLA_2$ activity and a 7.5-kDa subunit that shares sequence homology with protease inhibitors.

Experiments with bungarotoxin and 40% DMPC/60% 10,12-tricosadiynoic acid (TRCDA) liposomes displayed a maximum colorimetric response of approximately 50% after a one hour incubation time. The response curve was similar to that of the $PLA_2$ assay. In addition, after incubation with BUTX, the liposomes in the assay solution not only changed color, but also precipitated. In a previous study, BUTX was shown to induce fusion of small unilamellar liposomes (Rufini et al., Biochemistry 29, 9644 [1990]). The mechanism of the fusion remains unclear, but it seems to be dependent upon the interaction between BUTX, $Ca^{2+}$, and lysophospholipids.

This bungarotoxin assay provides an example of a large molecular assembly possessing enzymatic properties that is capable of producing a colorimetric change in the biopolymeric materials. In some embodiments, it may be desired to add additional bungarotoxin-detecting features to the biopolymeric materials to enhance the colorimetric detection. For example, antibodies raised against bungarotoxin (i.e., ligands) can be incorporated onto the biopolymeric materials in addition to DMPC. Thus, when bungarotoxin is present in a sample, the ligand/analyte interaction and the enzyme/substrate reaction will combine to provide an enhanced colorimetric response.

IV. Other Enzyme Systems

The present invention will find use in detecting, measuring, and characterizing the enzyme activities of many other systems including, but not limited to, lipolytic enzymes, acyltransferases, protein kinases, glycosidases, isomerases, ligases, polymerases, and proteinases, among others. Such enzymes can be free in solution, or be part of larger molecular aggregates, cells, and pathogens. For a general description of biocatalytic events, the reader is directed to Dordick (Dordick, *Biocatalysts for Industry*, Plenum Press [1991]).

For example, glycosidases can be detected to measure their activity or as indicators of the presence of a pathogen. Sialidases such as neuraminidase are found on influenza virus, and other sialidases are associated with Salmonella. By providing biopolymeric materials with substrate for the glycosidases, the presence of the pathogens can be detected. In combination with other detection elements (e.g, sialic acid ligands for detection of influenza virus), extremely sensitive calorimetric sensors can be produced.

Substrates can also be provided to produce detection systems for proteinases. For example, *Candida albicans* can be detected though its protease activity on pepstatin substrates. Also, anthrax spores from *Bacillus anthracis* can be detected by identifying laccase activity though its reaction with a substrate. Laccases are multi-copper-containing enzymes that catalyze oxidative conversion of a variety of substrates, including phenols, poly-phenols, and aromatic amines. Specific substrates include vanillic acid, syringic acid, and 2-2'-azino-bis(3-ethyl-benzthioazoline-6-sulfonic acid). By introducing one or more of these known laccase substrates into the biopolymeric materials of the present invention, a detection assay for antrax spores may be generated.

Other applications include incorporation of nucleic acids onto the biopolymeric material to test the activity of nucleotide polymerases (e.g., DNA polymerase). These assay systems will find use in techniques for identifying and characterizing polymerase inhibitors. From these examples, it is clear that the biopolymeric materials of the present invention find use in the calorimetric detection of a broad array of membrane conformational changes and reactions.

V. Inhibitor Screening

As described above, the presently claimed invention provides methods for detecting the activity of enzymes and other molecules that alter the conformation of biopolymeric membranes. These methods can be expanded to provide an accurate, and fast screening technique for identifying and characterizing inhibitors of the activity responsible for the calorimetric change (e.g., identifying and characterizing protease inhibitors by subjecting candidate inhibitors to biopolymeric materials comprising the protein substrates for the enzymes).

For example, with the detection of $PLA_2$ enzyme activity described above, the color change of the DMPC/PDA vesicles can be suppressed by using inhibitors to $PLA_2$. In the presence of the inhibitor 1-hexadecyl-3-trifluoroethylglycero-2-phosphomethanol (MJ33) (Gelb et al., supra; and Jain et al., Biochemistry 30, 10256 [1991]), the vesicles remained in their blue phase upon addition of $PLA_2$. These color differentials were clearly visualized for $PLA_2$/vesicle suspension in the presence (blue) and absence (red) of MJ33 in a 96-well microtiter plate. The absorbance of the wells was measured using a standard microplate reader, and quantitatively confirmed the suppression of the colorimetric response as shown in FIG. 17. This figure shows the colorimetric response curves for DMPC/PCA vesicles in the absence of inhibitor (solid line, max error 1.9%) and in the presence of MJ33 (dashed line, squares, max error 6.9%). Also shown is the inhibition of $PLA_2$ by replacement of $Ca^{2+}$ with $Zn^{2+}$ (dashed line, diamonds, max error 6.5%).

The inhibition of the blue to red color change by MJ33 indicates that non-specific adhesion does not play a role in the biochromic response, and $PLA_2$ activity is directly responsible for the color change. Inactivation of $PLA_2$ is also observed upon removal of $Ca^{2+}$, the catalytic co-factors for $PLA_2$ (Gelb et al., supra), from the buffer solution. Similarly, $PLA_2$ Prepared in buffer containing $Zn^{2+}$ instead of $Ca^{2+}$ ions does not induce a blue to red color change of the vesicles as shown in FIG. 17 (dashed line, diamonds). The vesicles also do not change color in the presence of other enzymes such as lysozyme and glucose oxidase, both of which produce a colorimetric response below 5% after more than an hour of incubation with the 40% DMPC/PDA vesicles. The specificity of the colorimetric response provides the necessary selectivity for high throughput screening of enzyme inhibitors.

For screening inhibitors, biopolymeric material comprising a substrate for the enzyme being tested, are placed into a multi-chambered device (e.g., a 96-well plate). Each well is incubated with a sample suspected of containing an enzyme inhibitor. The enzyme is then added and the observation of a color change is detected. Successful inhibitors will partially or completely prevent the enzyme from producing a color change in the biopolymeric material. Appropriate control samples (e.g., a sample with no inhibitor and a sample with known inhibitor) are run with the assay to provide confidence in the results.

VI. Designed Catalysts

The biopolymeric materials of the presently claimed invention further provide methods for screening the efficacy and activity of "designed" proteins, peptides, and catalytic antibodies. There is much current activity in engineering enzymes to be stable under specific conditions of solvent and heat, among other conditions. By providing a substrate for such enzymes in the biopolymeric materials of the present invention, a simple, accurate screen of these engineered proteins can be conducted under a variety of test conditions. Likewise, the inventive methods can be used to screen and characterize the reactions of catalytic antibodies.

VII. Immobilization of Biopolymeric Materials

The biopolymeric material of the present invention can be immobilized on a variety of solid supports, including, but not limited to polystyrene, polyethylene, teflon, silica gel beads, hydrophobized silica, mica, filter paper (e.g., nylon, cellulose, and nitrocellulose), glass beads and slides, gold and all separation media such as silica gel, sephadex, and other chromatographic media. In some embodiments, the biopolymeric materials are immobilized in silica glass using the sol-gel process.

Immobilization of the colorimetric biopolymeric materials of the present invention may be desired to improve their stability, robustness, shelf-life, colorimetric response, color, ease of use, assembly into devices (e.g., arrays), and other desired properties. In some embodiments, placement of calorimetric materials onto a variety of substrates surfaces can be undertaken to create a test method similar to the well-known and easy to use litmus paper test. For example, the reflective properties of nylon filter paper greatly enhance the colorimetric properties of the immobilized polydiacetylene liposomes. Filter paper also increases the stability of the liposomes due to the mesh size. In another example, the liposome embodiment of the present invention has been loaded into the ink cartridge of a ink jet printer and used to print biopolymeric liposome material onto paper as though it were ink. The liposome material present on the paper maintained its colorimetric properties. This embodiment demonstrates the ease with which patterned arrays can be generated into any desired shape and size. By using multiple cartridges (e.g., using a color printer), patterned arrays can be generated with different biopolymeric materials.

A. Entrapment of Biopolymeric Material by the Sol-Gel Method

While the sol-gel process has been used for entrapping organic molecules such as dyes and biomolecules in silica gels (See e.g., Avnir, Accounts Chem. Res. 28: 328 [1995]; Yamanaka et al., Am. Chem. Soc. 117: 9095 [1995]; Miller et al., Non-Cryst. Solids 202: 279 [1996]; and Dave et al., Anal. Chem. 66: 1120A [1994]), prior to the development of the present invention, immobilization of self-organized molecular aggregates (e.g., biopolymeric material, self-assembling monomer aggregates, and liposomes) was not realized in sol-gel materials.

Embodiments of the presently claimed invention provide for the successful immobilization of spherical, bilayer lipid aggregates, and liposomes using an aqueous sol-gel procedure. These molecular structures, and particularly liposomes, composed of biological or biomimetic (ie., mimics nature) lipids, are fairly robust under aqueous conditions and ambient temperatures, but can easily degrade in the presence of organic solvents and high temperatures. The sol-gel process provides a facile method of immobilizing molecular aggregates with no detectable structure modification, creating robust structures that are easily fabricated into any desired size or shape.

The silica sol-gel material was prepared by sonicating tetramethylorthosilicate, water, and hydrochloric acid under chilled conditions until a single phased solution was obtained. The use of metal oxides, other than tetramethylorthosilicate, are contemplated by the present invention, so long as they facilitate the entrapment and form substantially transparent glass material. Such metal oxides include, but are not limited to, silicates, titanates, aluminates, ormosils, and others. Buffer was then added to the acidic solution under cooling conditions. The biopolymeric materials, generated as described above, were mixed into the buffered sol solution. This composite was poured into a desired molding structure and allowed to gel at ambient temperatures. It is not intended that the present invention be limited by the type of molding structure used, as it is contemplated that a variety of structures can be applied to generate gels of any desired size and shape including, but not limited to, cuvettes, flat surfaces for generating thin films, plastic, ceramic, or metal moldings to generate badges, etc. It is not intended that the present invention be limited to gelation at ambient temperatures, as any temperature range that facilitates the production of functional analyte-detecting gels is contemplated.

Figure 18:
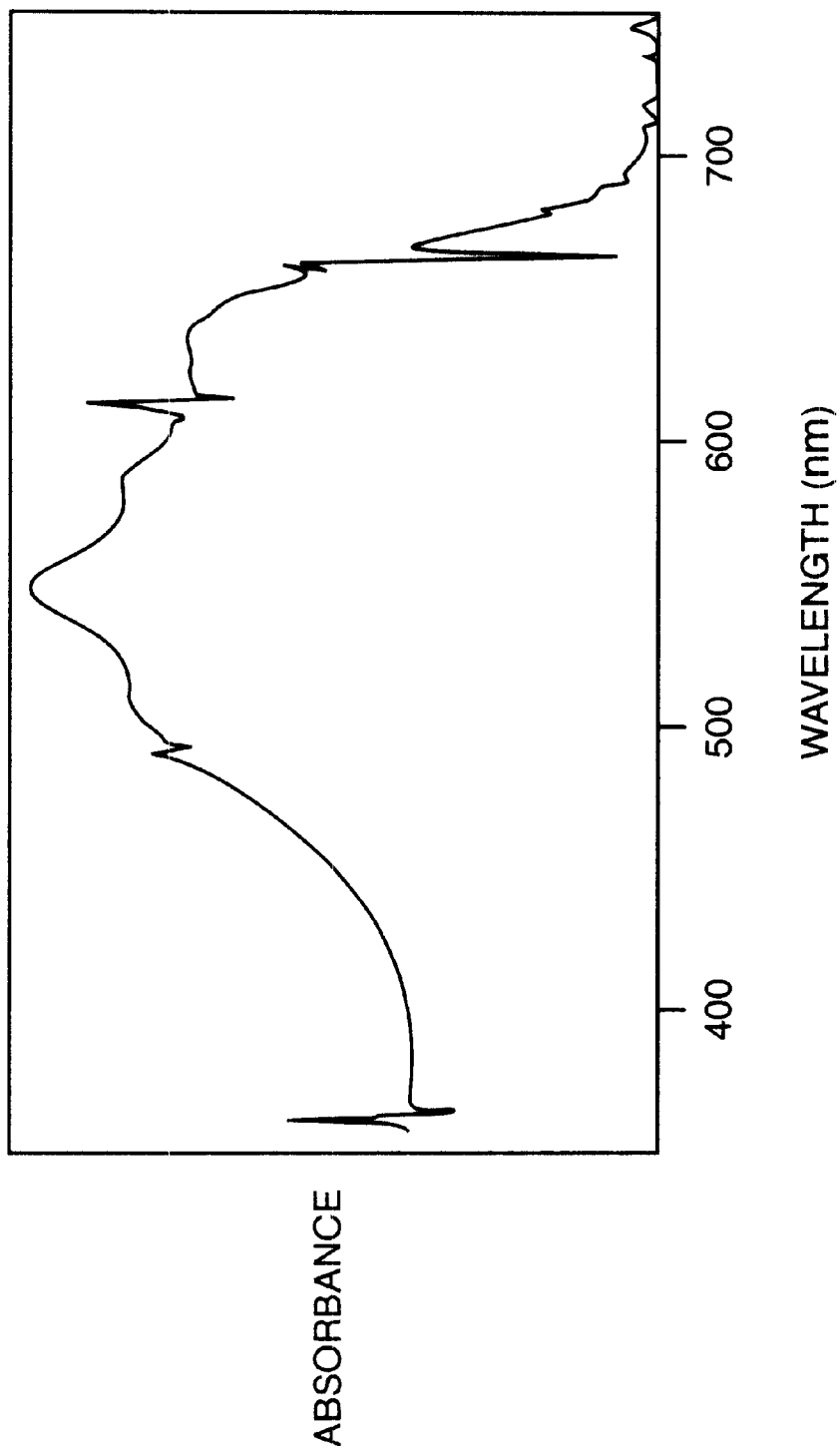
FIG. 18 shows the visible absorption spectra of the polydiacetylene liposomes in a sol-gel matrix.
Figure 19:
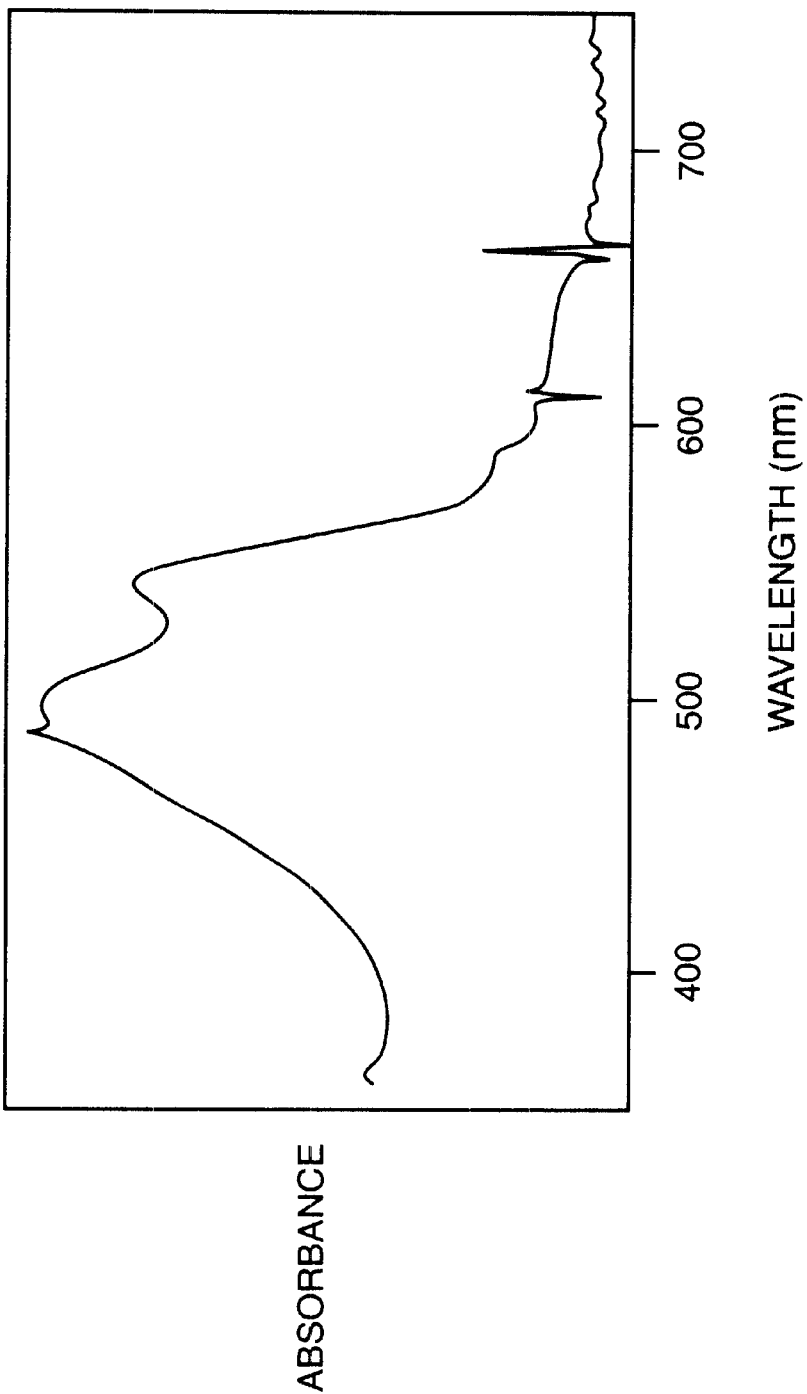
FIG. 19 shows the visible absorption spectra of the material in FIG. 18 following heating of the liposomes to 55° C.

In one embodiment, DCDA liposomes were incorporated into sol-gel glass, although incorporation of any biopolymeric structure is contemplated by the present invention. Following the sol-gel procedure as described above, gelation occurred within a few minutes, producing gels with a violet color. The visible absorption spectra of the polydiacetylene liposomes, as shown in FIG. 18, was unaltered in the sol-gel matrix compared to liposomes in solution. Following heating of the liposomes to 55° C., a blue to red thermochromic transition occurred that was characteristic of polydiacetylene materials. The blue to red phase materials were similarly unchanged in the sol-gel state compared to solution as shown in the spectrum in FIG. 19. Thus, the presently claimed invention provides a sol-gel matrix that is compatible with fragile biopolymeric structures (i.e., liposomes) and maintains those physical properties that were observed in bulk solution.

Additionally, it is contemplated that sol gel prepared materials of various thicknesses will possess unique sensitivities to analytes. Thicker films have a higher surface to volume ratio and therefore may require a higher concentration of analyte to trigger the chromatic transition.

Furthermore, the gelling conditions of the sol-gel preparation can be optimized by varying gelling temperatures, gel materials, and drying conditions to generate material with desired pore sizes. Varying the crosslink density of the material also provides control over pore size. Pore sizes from nanometers to hundreds of nanometers or greater are contemplated by the present invention. Some gels allow size-selective screening of undesired material while maintaining analyte access to the ligand. Also, the sol-gel technique allows structures to be formed that can be molded into any desirable shape, including, but not limited to, cartridges, coatings, monoliths, powders, and fibers.

B. Immobilization by Chemical Linkage

In some embodiments of the present invention, the biopolymeric material can be attached to membranes of poly(ether urethanes) or polyacrylonitrile. These membranes are porous, hydrophilic and can be used for affinity separations or immunodiagnosis. The liposomes of the present invention can be coupled to these membranes by first attaching an activating group such as imidizolyl-carbonyl, succinimido, FMP or isocyanate to the membrane which adds rapidly to nucleophiles (e.g., $-NH_2$, $-SH$, or $-OH$ groups) present in the liposomes. Thus, any liposome preparation which contains these functionalities can be directly attached to the membrane. This procedure is analogous to the coupling of proteins to membranes, the latter of which is well known in the art (See e.g., Bamford et al., Chromatography 606: 19 [1992]).

A variety of other immobilization techniques known in the art can be applied to the biopolymeric material of the present invention. For example, materials which have an $-SH$ functionality can also be immobilized directly to gold surfaces, particles, or electrodes via the thiol-gold bond. In this case, a solution of the liposomes containing the $-SH$ group are incubated with the clean gold surface in water for 12–24 hours with stirring at room temperature. Also, materials can be immobilized to silicon chips or silica gel (e.g., silicon dioxide) using the procedure described in Example 8. Furthermore, materials containing $-NH_2$ functionalities can also be immobilized onto surfaces with standard glutaraldehyde coupling reactions that are often used with the immobilization of proteins. Additionally, liposomes can be attached through their carboxy groups to surfaces comprising polyethyleneimine, a branched polymer with free amine groups.

VIII. Arrays

Certain embodiments of the presently claimed invention contemplate the generation of a large palette of polymerizable lipids with different headgroup chemistries, ligands, dopants, monomers or other properties within a single device to increase selectivity, sensitivity, quantitation, ease of use, and portability, among other desired characteristics and qualities. By using the array format, several advantages can be realized that overcome the shortcomings of a single sensor approach. These include the ability to use partially selective sensors and to measure multicomponent samples. This offers the possibility of sensing a specific sample in the presence of an interfering background, or to monitor two or more samples of interest at the same time. The sensitivities of a given lipid to a given sample can be determined in order to generate identifiable fingerprints characteristic of each sample. For example, the lipid-polymer film of PDA derivative A may convert completely to an orange phase in the presence of sample X (%CR=100), while PDA derivative B may have a %CR of 70 giving rise to a pink color, and PDA derivative C may have a %CR of 40 yielding a purple color and PDA derivative D may not change at all (i.e., therefore, remains blue/purple). The response fingerprint orange/pink/purple/blue-purple would indicate the presence of sample X. Clearly, the higher the number of elements in the array, the greater the chance of a positive identification for a given analyte. By immobilizing the biopolymeric material, materials of any desired size and shape can be created and incorporated into a small, easily read, and interpretable device.

Arrays can be generated that measure both the presence and activity of samples. For example, when characterizing a certain enzyme, one portion of the array can provide analyte-detecting capabilities for the enzyme (e.g., by incorporating a ligand that interacts with the enzyme), while another provides and enzyme activity assay (e.g., by including a substrate for the enzyme within the biopolymeric material). Such arrays can be expanded for use in inhibitor screening techniques where each portion of the array provides quantitative or qualitative data, or provides a control experiment.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); 1 or L (liters); ml (milliliters); $\mu$l (microliters); cm (centimeters); mm (millimeters); $\mu$m (micrometers); nm (nanometers); $\mu$Ci (microcurie); mN (millinewton); Å (angstrom); kDa (kilodalton); ppm (parts per million); N (newton); °C. (degrees Centigrade); wt % (percent by weight); aq. (aqueous); J (Joule); UV (ultraviolet); XPS (x-ray photoelectron spectroscopy); PDA (diacetylene monomer); PCA (pentacosadiynoic acid monomer); DCDA (docosadynoic acid); TRCDA (tricosadiynoic acid); SA-PDA (sialic acidderived PDA); BUTX (bungarotoxin); OTS (octadecyltrichlorosilane); VOC (volatile organic chemical); CR (calorimetric response); pH (hydrogen ion concentration); EDC (ethylcarboiimide hydrochloride); AFM (atomic force microscope); Hz (Hertz); LB (Langmuir-Blodgett); NHS (N-hydroxy succinimide); $CO_2$ (carbon dioxide); $MgSO_4$ (magnesium sulfate); $CdCl_2$ (cadmium chloride); MeOH (methanol); Be (beryllium ions); Mg (magnesium ions); Ca (calcium ions); Ba (barium ions); $N_2$ (nitrogen gas); Sigma (Sigma Chemical Co., St. Louis, Mo.); Perkin-Elmer (Perkin-Elmer Co., Norwalk, Conn.); Fisher (Fisher Scientific, Pittsburgh, Pa.); and Farchan Laboratories (Farchan Laboratories, Inc., Gainesville, Fla.); Park Scientific Instrument (Park Scientific Instruments, Sunnyvale, Calif.); Biorad (Bio-Rad Laboratories, Hercules, Calif.); Gelman (Gelman Sciences, Ann Arbor, Mich.); Pierce (Pierce, Rockford, Ill.); and Bellco Glass (Bellco Glass Inc., Vineland, N.J.).

All compounds were of reagent grade purity and used as supplied unless stated otherwise. Organic solvents were of spectral grade from Fisher Scientific. All aqueous solutions were prepared from water purified through a Barnstead Type D4700 NANOpure Analytical Deionization System with ORGANICfree cartridge registering an 18.0 M-Ohm-cm resistance.

Example 1

Biopolymeric Material Preparation

I. Production of Liposomes

The self-assembling monomers to be incorporated into the liposomes were dissolved in solvent (e.g., chloroform for diacetylenes and methanol for ganglioside $G_{M1}$). Many other volatile solvents find use in the present invention, including, but not limited to, benzene, hexane, and ethylacetate. The solvent solutions were mixed in appropriate volumes in a brown vial (i.e., to prevent light interference during the upcoming drying steps) to achieve the desired lipid mixture (e.g., 5% by mole of $G_{M1}$, 95% diacetylenes) and a total lipid content of approximately 2 $\mu$mol. The solvent was then evaporated by rotary evaporation or with a stream of nitrogen gas. The dried lipids were resuspended in sufficient de-ionized water to produce a 1–15 mM solution of lipid. The solution was then sonicated for 15–60 minutes with a probe sonicator (Fisher sonic dismembrator model 300, 50% output, microtip) as described by New (New, supra). The solution was heated during the sonication (in most cases the sonicating process alone provides sufficient heat) to a temperature above the phase transition of the lipids used (typically 30–90° C.). The resulting mixture was filtered through a 0.8 micromole nylon filter (Gelman) or through a 5 mm Millipore Millex-SV filter and cooled to 4° C. for storage or was polymerized. In one embodiment, prior to polymerization, oxygen in the solution was removed by bubbling nitrogen through the sample for 5–10 minutes.

Polymerization of the stirred liposome solution was conducted in a 1 cm quartz cuvette with a small 254 nm UV-lamp (pen-ray, energy: 1600 microwatt/cm$^2$) at a distance of 3 cm. The chamber was purged with nitrogen during the polymerization to replace all oxygen and to cool the sample. Polymerization times varied between 5 and 30 minutes depending on the desired properties (e.g., color, polymerization degree) of the liposomes. In other embodiments, the solution was placed in a UV-chamber, without purging, and exposed to 0.3–20 J/cm$^2$ of ultraviolet radiation, preferably 1.6 J/cm$^2$, for 5–30 minutes.

In some embodiments, polymerization was conducted in a multi-chambered plate (e.g., ELISA plate). Approximately 200 $\mu$l of sonicated liposome solution was placed in each well of the plate. The plate was placed under a UV lamp with the distance between the plate and the lamp kept at 3 cm. Irradiation times typically lasted for a minute. Prolonged irradiation resulted in formation of pink/purple liposomes, indicating that a color change was initiated by UV light. Such liposomes gave inconsistent results and should be avoided.

II. Production of Films

Polydiacetylene films were formed in a standard Langmuir-Blodgett trough (See e.g., Roberts, *Langmuir Blodgett Films*, Plenum, New York [1990]). The trough was filled with water to create a surface for the film. Distilled water was purified with a millipore water purifier with the resistivity of 18.2 M-Ohm. Diacetylene monomers (e.g., 5,7-docosadiynoic acid, 10,12-pentacosadiynoic acid [Farchan Laboratories], 5,7-pentacosadiynoic acid, combinations thereof, or other self assembling monomers), dissolved in a solvent spreading agent (e.g., spectral grade chloroform [Fisher]), were layered onto the aqueous surface with a syringe, to form a continuous film. Monomers prepared in the concentration range of 1.0 to 2.5 mM, were kept at a temperature of 4° C. in the dark, and were allowed to equilibrate at room temperature before being used in experiments.

Once layered on the water surface, the film was physically compressed using moveable barriers to form a tightly-packed monolayer of the self-assembling monomers. The monolayer was compressed to its tightest packed form (i.e., until a film surface pressure of 20–40 mN/m was achieved). Following compression, the film was polymerized. Certain embodiments (e.g., embodiments with dopants) of the present invention may require surface pressure compression greater or less than 20–40 mN/m.

Ultraviolet irradiation was used to polymerize the monomers, although other means of polymerization are available (e.g, gamma irradiation, x-ray irradiation, and electron beam exposure). Pressure was maintained on the film with the moveable barriers throughout the irradiation process at surface pressure of 20–40 mN/m. An ultraviolet lamp was placed 20 cm or farther from the film and trough. It was found that if the lamp is placed closer to the film, damage to the diacetylene film may occur due to the effects of heating the film. The film was exposed to ultraviolet light with a wavelength of approximately 254 nm for approximately one minute. The polymerization was confirmed by observing the blue color acquired upon polymerized diacetylene formation and detecting the linear striations typical of polymerized diacetylene films with a polarizing optical microscope.

III. Production of Tubules

Self-assembling monomers to be incorporated into the tubules were dissolved in solvent, mixed together, evaporated, and resuspended in water as described above for liposomes. 1–10% by volume of ethanol was added to the solution, although other organic solvents are contemplated by the present invention. The solution was then sonicated (with heating if necessary), filtered, cooled, and polymerized as described above for liposomes.

Example 2

Examination of Biopolymeric Materials

I. Optical Microscopy and X-ray Spectroscopy

Diacetylene films were prepared in a Langmuir Blodgett trough as described above using a combination of PDA monomers and sialic acid-derived PDA monomers. The floating polymerized assembly was lifted by the horizontal touch method onto a glass slide previously coated with a self-assembled monolayer of octadecyltrichlorosilane (OTS) as described (Maoz and Sagiv, J. Colloid Interface Sci. 100: 465 [1984]).

Figure 20:
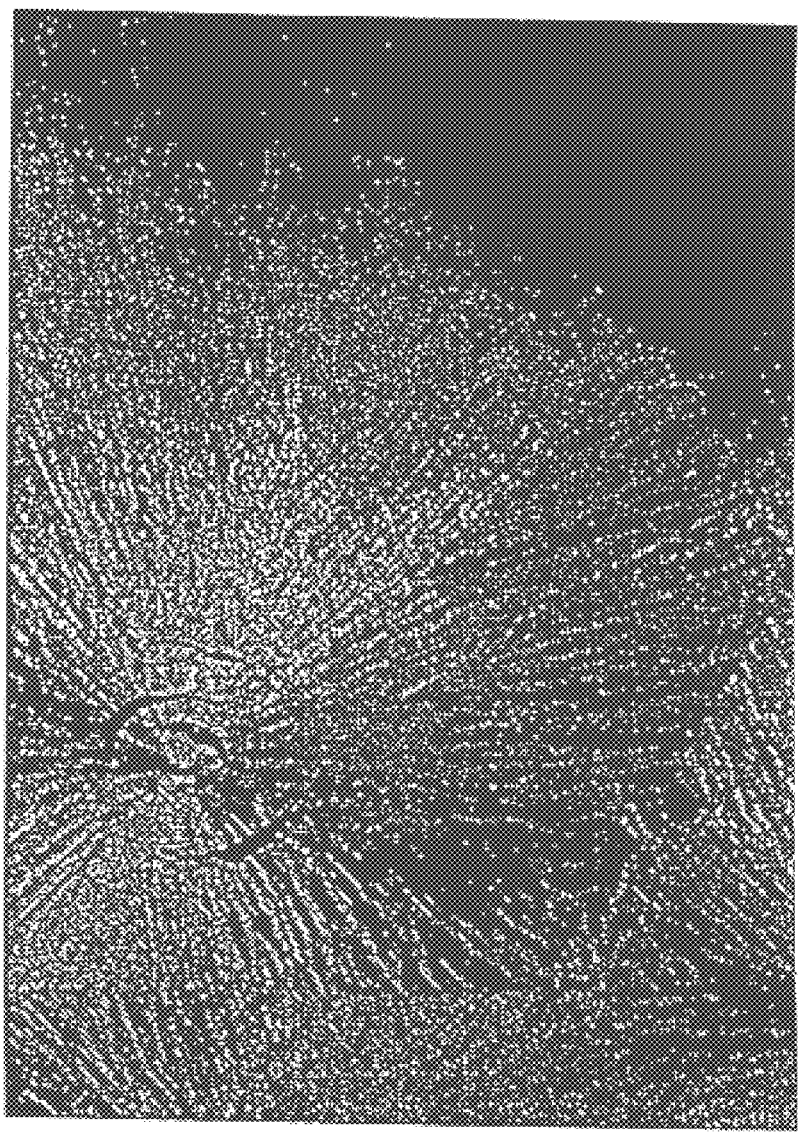
FIG. 20 shows an optical micrograph of diacetylene film.

The slide was then examined by optical microscopy with the use of crossed polarizers as described (Day and Lando, Macromolecules 13: 1478 [1980]). The film exhibited a high degree of order over a macroscopic range (i.e., 50 to 150 $\mu$M) as shown in the optical micrograph of FIG. 20. Large domains up to 150 $\mu$M were visible (1 cm=10 $\mu$M).

The films were further characterized by angle-resolved x-ray photoelectron spectroscopy (XPS) and ellipsometry. The XPS results indicated that the amide nitrogen atoms and the carbonyl carbon atoms of the head groups were localized at the surface relative to the methylene carbons of the lipid chains, demonstrating that the sialoside head group was presented at the surface of the film. Ellipsometric analysis of the polydiacetylene monolayer coated on HF-treated silicon indicated a film thickness of approximately 40 Å, in agreement with the expected value based on molecular modeling.

II. Atomic Force Microscopy

In situ atomic force microscopy was used to reveal the morphology, surface topography, and growth and dissolution characteristics of microscopic biopolymeric crystals, and allowed dynamic observations of nucleation events and the determination. Studies were conducted using standard techniques for in situ studies as described by Binnig et al. (Binnig et al., Phys. Rev. Lett. 12: 930 [1986]; and Binnig et al., Europhys. Lett. 3: 1281 [1987])

Two different atomic force microscopes were used in this study. Images larger than 1 $\mu$m$^2$ were acquired with a commercially available instrument (Park Scientific Instrument). In this case Si ultralevers (Park Scientific Instrument) were used. Commercially available photolithographically patterned glass slides (Bellco Glass) were used to allow imaging of the exact same region of the film after each temperature step. Images smaller than 1 $\mu$m$^2$ were taken with a home-built AFM (Kolbe et al., Ultramicroscopy 42–44: 1113 [1992]). Si$_3$N$_4$ cantilevers with a nominal force constant of 0.1 N/m were used (Park Scientific Instruments). Both microscopes were operated in contact mode, and in the latter case a four-quadrant position-sensitive photodiode allowed the measurement of the cantilever bending and twisting simultaneously. All images were acquired in contact mode under ambient conditions.

Example 3

Optimization of Biopolymeric Materials

The present invention provides a variety of different biopolymeric material forms (e.g., liposomes, films, tubules, etc.), with and without dopant materials, with a variety of ligands, and immobilized in a variety of forms. For each of these embodiments, it is possible to optimize the biopolymeric material to maximize sensitivity, robustness, colorimetric response, and other desired factors. Described below are a few illustrative examples of such optimization. These examples are intended to merely illustrate the flexibility of the present invention. It is not intended that the present invention be limited to these particular embodiments.

I. Mixed Monomers

The biopolymeric material of the presently claimed invention can comprise a sample of pure monomers (e.g., pure diacetylene) or can comprise mixed monomers (e.g., PDA with Ganglioside G$_{M1}$ or dopant). Optimization of the percent composition of mixed monomers can be undertaken to provide biopolymeric material with desired properties. An example of such optimization is provided below for the detection of an analyte (i.e., cholera toxin) with a ganglioside ligand.

To evaluate the calorimetric response of G$_{M1}$/PDA films, different concentration combinations of ligand (i.e., GM$_1$) and PDA were tested. If too much ligand molecule was added (i.e., low concentration of polymerized lipid), the films were unstable and had high background. If the films had too much polymerized lipid molecule, they were too stable and the color change would not occur well. In search of the G$_{M1}$/PDA biosensor composition capable of displaying maximal response, a series of PDA monolayer films were transferred to OTS coated glass slides. The films were evaluated by exposure to cholera toxin and the colorimetric response was measured using UV-Vis spectroscopy. FIG. 21 summarizes the colorimetric properties and response of the G$_{M1}$ biosensing monolayer films studied in these experiments showing the initial absorbance, transfer rate, and colorimetric response in buffer and in response to analyte. The initial absorbance (A$_{init}$), which reflects the maximal peak value of the films at 640 nm, is a function of the film transfer rate and composition. GM$_1$, which does not provide chromatic functionality into the mixed assembly, generally decreases the intensity of the initial blue color. The transfer rate, which is the ratio of the area decreased on the tough surface and the area of the substrate emerged into the subphase, indicates that the PDA films are highly transferable as compared to those of sialic acid-PDA (SA-PDA) and $G_{M1}$ molecules. The blue to red colorimetric response (CR) shows that monolayer films exhibit low CR in buffer solution except when high content of $G_{M1}$ or SA-PDA is used.

II. Optimization of Subionic Phase

Figure 22:
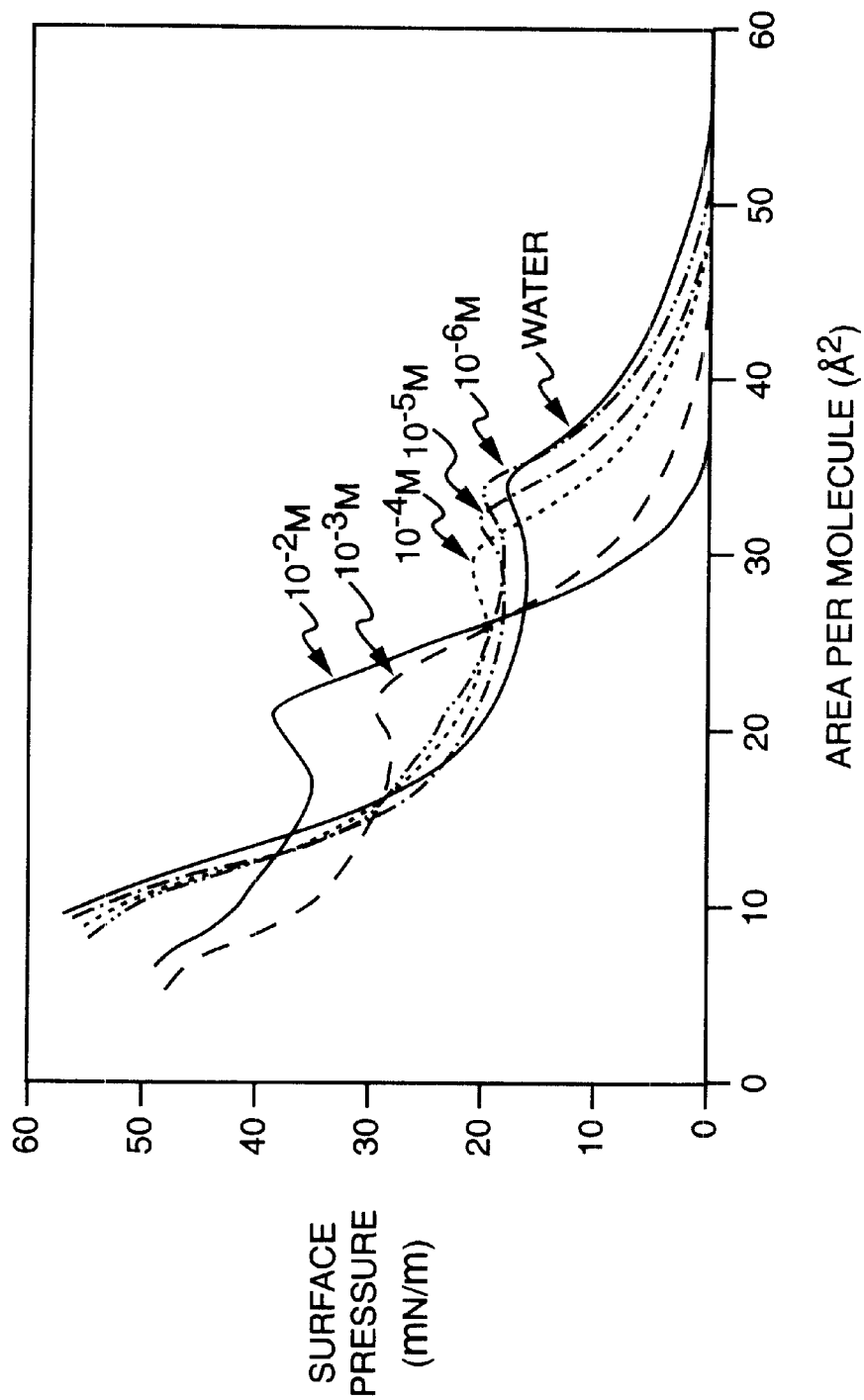
FIG. 22 shows the isotherms of 5% $G_{M1}$/5% SA-PDA/ 90% PDA as a function of subphase concentration of $CdCl_2$.

The ionic content of the aqueous subphase has significant impact on the properties of Langmuir monolayers. The presence of cationic species strengthens the electrostatic interaction of monolayer with anionic headgroups and consequently stabilized the film (Gaines, *Insoluble Monolayers at Liquid-Gas Interface, Interscience Publishers*, New York, pp 291–299 [1966]). FIG. 22 shows the isotherms of 5% $G_{M1}$/5% SA-PDA/90% PDA as a function of subphase concentration of $CdCl_2$. As the concentration of $Cd^{2+}$ is increased, the expanded phase shifts systematically toward the low molecular area, indicating that the monolayer is stabilized at high $Cd^{2+}$ concentration. This behavior results largely from the ionic interactions between $Cd^{2+}$ and partially dissociated anionic carboxylate headgroup of PDA (pKa≈5), while acidic SA-PDA and $G_{M1}$ (pKa≈2.6 for sialic acid on these molecules) probably also contribute to strengthen the effect. Further evidence for this mechanism of monolayer stabilization is seen in the increase in surface pressure as a function of higher ionic concentrations. Many divalent ions (Be, Mg, Ca, Ba, and Cd) have been shown to have an impact on the isotherms of PDA monomers through salt formation, which influences the packing of molecules on a basis of ion size and charge. No immiscible trend was observed for the ternary system of 5% $G_{M1}$/5% SA-PDA/ 90% PDA on aqueous subphases containing up to 0.01 M $Cd^{2+}$, indicating the this mixed monolayer is relatively stable as respect to ionic content. When $Cd^{2+}$ was increased to 0.1 M, however, erratic behavior of the 5% $G_{M1}$/5% SA-PDA/90% PDA monolayer was observed. This is possibly due to formation of aggregated domains as a result of different ability to interact with $Cd^{2+}$ between sialic acid in SA-PDA and $G_{M1}$ and carboxylic in PDA, or precipitation at high salt concentration.

At low $Cd^{2+}$ concentrations (i.e., approximately $10^{-4}M$), the isotherms differ very little in the condensed phase region, indicating that low ionic content in subphase has no significant effect on the structure of the compact films. Increasing the concentration of $Cd^{2+}$ above $10^{-3}M$, resulted in a shift of molecular area in the condensed phase region as shown in FIG. 22, pointing to some structural change in the compact monolayer. In order to explore the role of additives in the mixture for inducing such a structural change, an isotherm of pure PDA on $10^{-2}M$ $Cd^{2+}$ was measured. On the $10^{-2}M$ $Cd^{2+}$ subphase, a steep rise at low molecular area is seen in the isotherm of PDA. However, the slope of the isotherm within the compact region and the molecular area were essentially the same as on water. Such a result is consistent with an ordered film at high salt concentration, where the film characteristics are primarily dictated by the long hydrophobic segment of the molecules. Similar results were obtained for amine-based diacetylene (Walsh and Lando, Langmuir, 10: 252 [1994]). Therefore, the shift in FIG. 22 reflects a mixed electrostatic effect induced by differently dissociated individual components in the films, suggesting a lower stability of the ternary films as compared to the pure PDA films.

III. Optimization of Subphase pH

Figure 23:
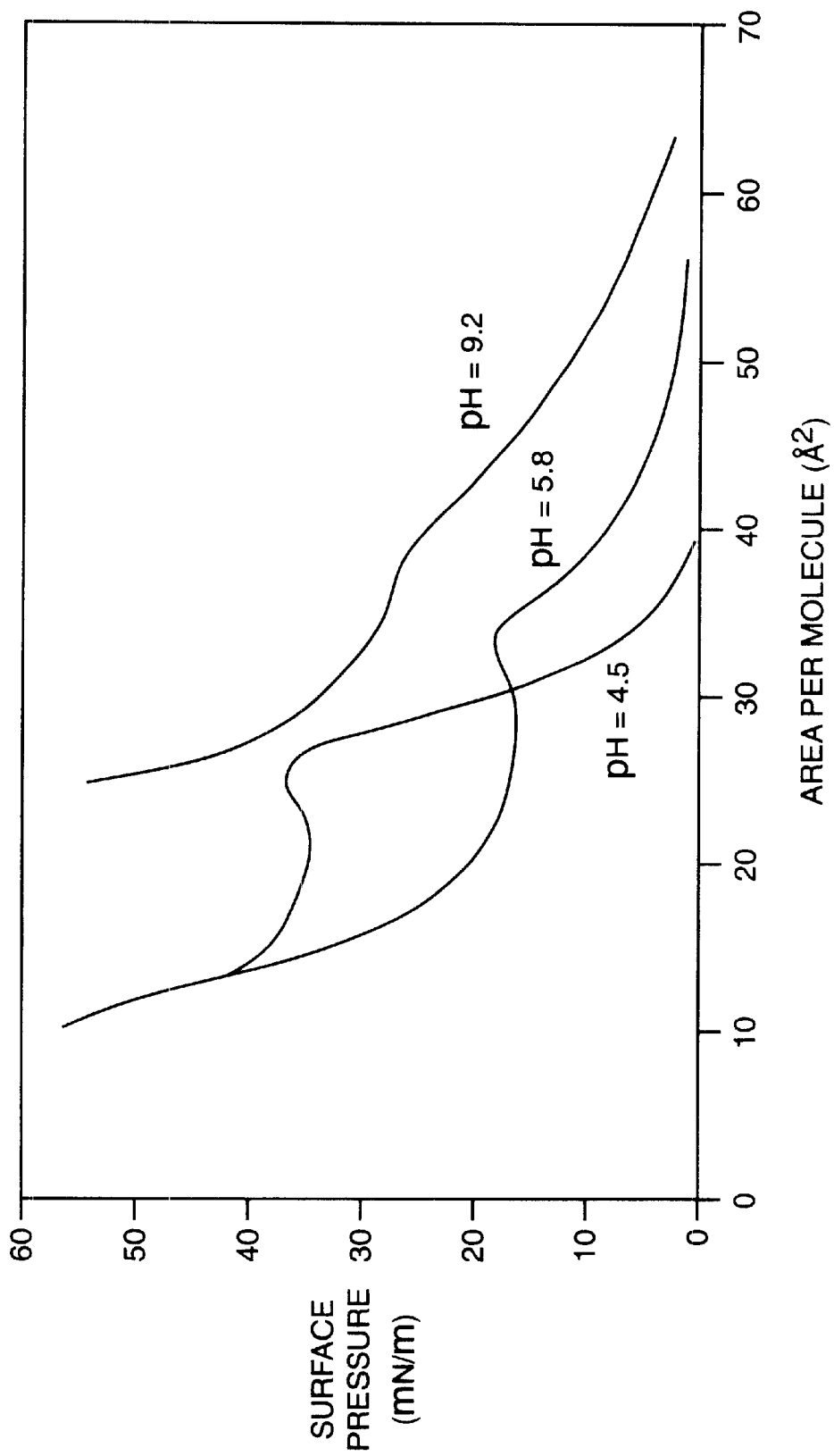
FIG. 23 shows the isotherms of 5% $G_{M1}$/5% SA-PDA/ 90% PDA at pH 4.5, 5.8, and 9.2.

For acidic molecule PDA, an increase in pH resulted in the ionization of PDA molecules and consequently introduced substantial charge along the monolayer interface. FIG. 23 shows the isotherms of 5% $G_{M1}$/5% SA-PDA/90% PDA at pH 4.5, 5.8, and 9.2. At high pH (pH 9.2), the film became very expanded as a result of electrostatic repulsion between the adjacent PDA molecules. Compression of such a film to form a monolayer was difficult. Additionally, distinct segments of individual molecules were observed, pointing to an immiscible trend in the mixed monolayer that tends to form segregated domains. Evidently, high charge density at the monolayer interface created unfavorable interactions on the aqueous surface. It can be expected that the addition of compounds such as $G_{M1}$ (i.e., which is acidic) into the PDA mixture at this pH will be unfavorable. The isotherm of the ternary system at low pH exhibits normal peak behavior. The collapse pressure is significantly larger than at neutral pH, indicating a more stable film formed at low pH. Suppression of ionization of the PDA molecules at this pH contributes to the enhancement of film stability, which can consequently stabilize the incorporation of $G_{M1}$, molecules in the PDA films.

IV. Optimization of Subphase Temperature

Figure 24:
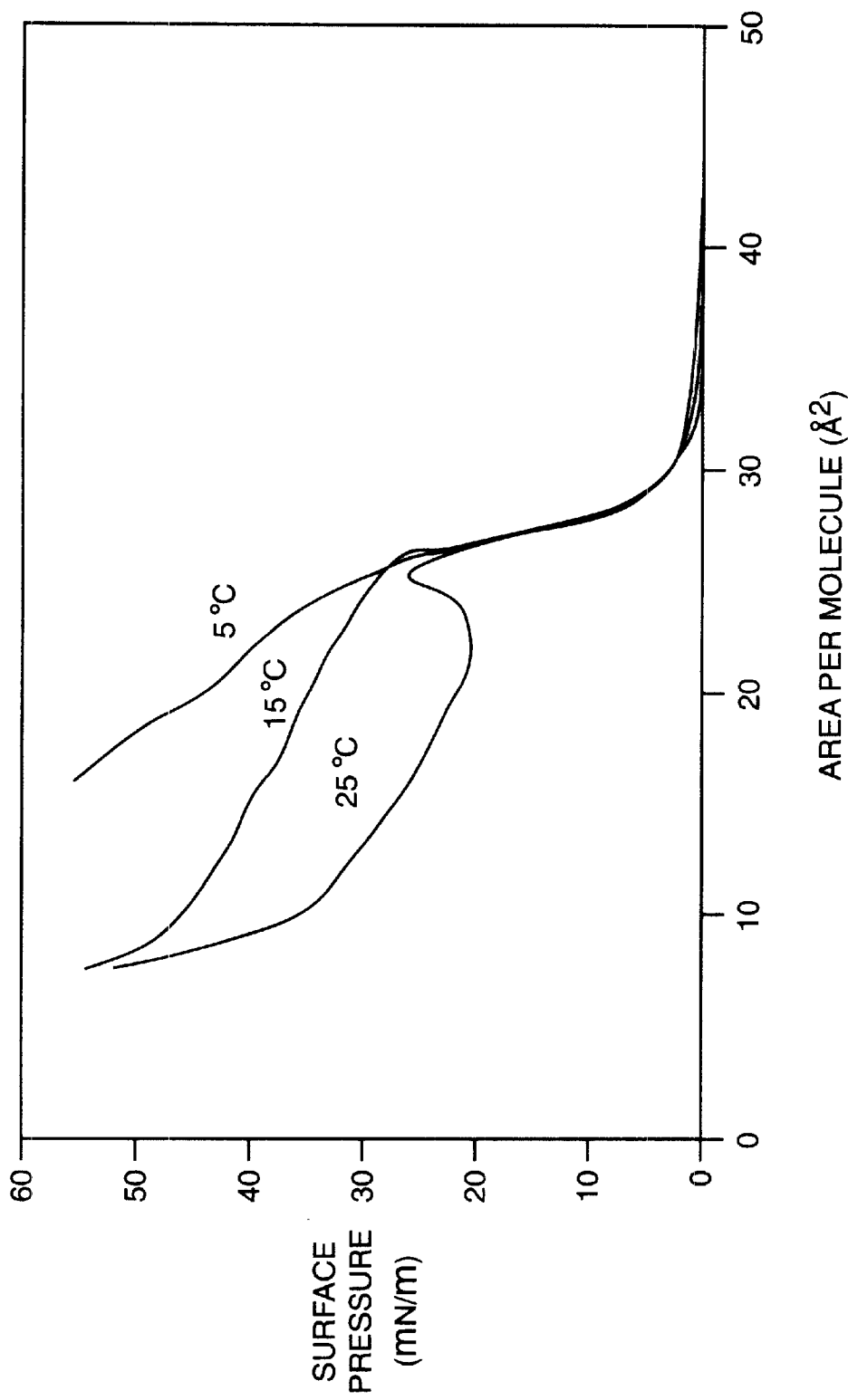
FIG. 24 shows the temperature effect on the isotherms of 100% PDA, 5%SA-PDA/95% PDA, and 5% $G_{M1}$/5% SA-PDA/90% PDA.

During film production, an increase in temperature usually results in higher surface pressure, an enlargement of the expanded region, and a shift in the phase transition point towards the low molecular area direction in $\pi/A$ isotherms (Birdi, *Lipid and Biopolymer Monolayers at Liquid Interfaces*, Plenum Press, New York [1989]). This effect stems from the higher flexibility of hydrocarbon tails of lipids at high temperature as a result of thermal agitation, and can be analyzed with the two-dimensional Clausius-Clapeyron equation (Birdi, supra). Monolayer films containing PDA, however, typically experience film collapse during compression. Consequently, the evaluation of the subphase temperature effect has to take this phenomenon into consideration. FIG. 24 displays the temperature effect on the isotherms of 100% PDA, 5%SA-PDA/95% PDA, and 5% $G_{M1}$/ 5% SA-PDA/90% PDA. With decrease in subphase temperature, the surface pressure increased and the isotherm shape changed. Isotherms at low temperature exhibited more and more liquid-solid phase transition features, as indicated by the disappearance of the peak and occurrence of the smooth curve at the transition region. All the $\pi$-A isotherms obtained for the three monolayers display similar characteristics. The major difference between these figures is the position of collapse point, which is a function of film composition.

V. Position of the Monomer Polymerizable Group

A comparison of the colorimetric responses of 10,12-pentacosadiynoic acid liposomes and 5,7-docosadiynoic acid (a gift from Alice Deckert of Holy Cross College) liposomes to analyte was conducted to determine the effect of the position of the polymerizable group within the self-assembling monomers. $G_{M1}$ ligands were incorporated into each type of liposome to analyze the detection of cholera toxin. The ganglioside $G_{M1}$ was mixed at 5 mol % with the diacetylene "matrix lipid" monomers. Liposomes were prepared using the probe sonication method and polymerized by UV irradiation (254 nm).

Figure 25:
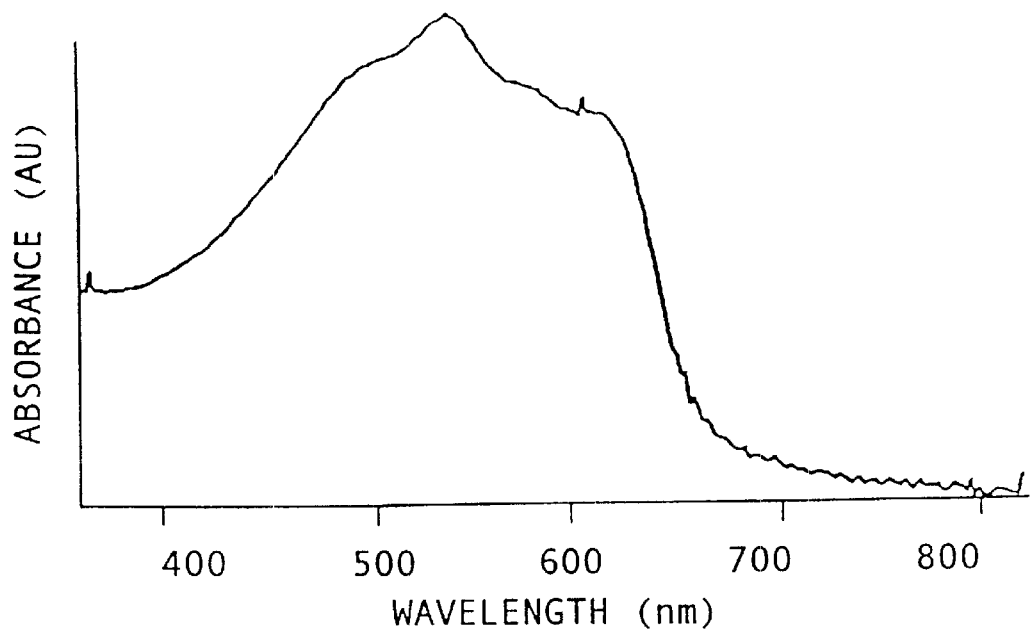
FIG. 25 shows the visible absorption spectrum of "blue phase" 5% $G_{M1}$ and 95% 5,7-docosadiynoic acid liposomes.
Figure 26:
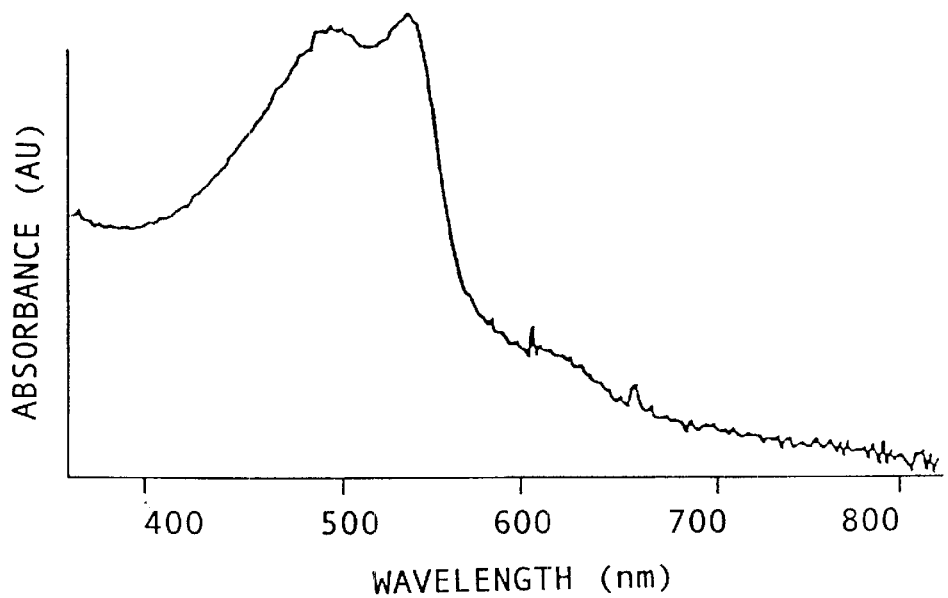
FIG. 26 shows the visible absorption spectrum of the liposomes of FIG. 25 following exposure to cholera toxin.

The conjugated ene-yne backbone of polydiacetylene liposomes resulted in the appearance of a deep blue/purple solution. The visible absorption spectrum of the freshly prepared purple liposomes is shown in FIG. 25. When cholera toxin was added to the liposomes composed of 5% $G_{M1}$ and 95% 5,7-docosadiynoic acid, the solution immediately changes to an orange color, and the "red phase" absorption of polydiacetylene dominates, as shown in FIG. 26. When the ganglioside $G_{M1}$ was mixed with a matrix lipid composed of 10,12-pentacosadiynoic acid instead of 5,7-docosadiynoic acid, the calorimetric response was significantly reduced. Although it is not necessary to understand the mechanism in order to use the present invention, and it is not intended that the present invention be so limited, it is contemplated that the enhanced sensitivity observed with the 5,7-docosadiynoic acid liposomes arises from the positioning of the optical reporter group nearer to the interface (i.e., three methylene units compared to eight). It has been shown by Fourier transform IR spectroscopy that small rotations about the C—C bond β to the polymer backbone are sufficient to change the effective conjugated length (Berman et al., Science 259: 515 [1995]). These conformational changes are more easily transduced through shorter alkyl chain length.

Example 4

Incorporation, Optimization, and Properties of Dopants

Each time a new sensor system is designed, the amount of PDA, dopant, and ligand (e.g., ganglioside) are varied to create the optimal sensor. Although 0–100% amounts are typically used for testing, optimal systems appear to use 5–15% ligands, 0–95% PDA, and 0–95% dopant. The percent of each component depends on the system, the needed stability, and the needed sensitivity. Certain embodiments of the present invention may incorporate more than one type of dopant into the biopolymeric material.

I. Incorporation of Dopant into Biopolymeric Material

Amino-acid derivatized diacetylene dopants were incorporated into colorimetric liposomes. The lipids (i.e., the dopants and the diacetylene monomers) were first dissolved in chloroform, and an aliquot was transferred to the reaction vial. The organic solvent was blown out by use of $N_2$ gas, and an appropriate amount of water was added to bring the lipid concentration to approximately 1 mM. Bath sonication was used to break down the white precipitate to form liposomes. Typical sonication times varied from 1 hour to 5 hours, dependent on the type of dopants used. During sonication, the temperature was carefully raised to approximately 80° C. to facilitate the formation of the liposomes. The sonication continued until the solutions became clear. The hot solutions were immediately filtered though a 5 $\mu$M Millipore Millex-SV filter to remove any impurity that may be present in the solution. The obtained solutions were stored at 4° C. overnight before use.

Following polymerization, deep blue colored liposomes were obtained. The final liposomes contained the amino-acid derivatized diacetylene dopant.

II. Optimization of Dopant Concentration

Films comprising PDA, $G_{M1}$ (i.e., the ligand) and sialic acid-derived PDA (i.e., the dopant) were generated as described in Example 3, Section I for the detection of cholera toxin. Colorimetric assays demonstrated that all three components were required for optimal calorimetric response. For the optimal detection of cholera toxin, both SA-PDA and $G_{M1}$ need be present in the films, otherwise the films are either too unstable or they do not change color well, depending on the concentration of all three components. Although it is not necessary to understand the mechanism in order to use the present invention, and it is not intended that the present invention be so limited, it is contemplated that the function of SA-PDA is to provide the metastable state of the films for biomolecular recognition through a stress-induced mechanism (Charych et al, Chem. and Biol. 3: 113 [1996]). A film consisting of 1% $G_{M1}$/1% SA-PDA/98% PDA was also investigated. The CR turned out to be low and it did not yield a useful calorimetric biosensor. As shown in FIG. 21, the optimal colorimetric sensor was determined to be 5% $G_{M1}$/5% SA-PDA/90% PDA. Thus, a 5% molar content of the dopant SA-PDA provides the best sensor for detection of cholera toxin.

III. Properties of Derivatized Diacetylene Dopants

Hydrophobic amino acids linked to diacetylenes can be used to lower the solubility of the biopolymeric material as well as the stability of the films or liposomes. These derivatized PDA's can be useful in the assembly of complex systems to fine tune the stability and sensitivity, two factors that are directly coupled to one another. Using the hydrophobic PDA's with the hydrophilic PDA's, the stability of films and liposomes can be greatly increased, under a variety of environmental conditions. Although a large gain in stability is seen, it is at a cost to sensitivity. A balance between sensitivity and stability has to be optimized.

Acidic and basic amino acids linked to diacetylenes can be used to increase the solubility of the material. Specifically, these changes allowed polydiacetylene lipids to mix with water soluble biological molecules. Ordinarily, PDA is not water soluble and organic solvents are necessary (i.e., which can be destructive to biological molecules). By placing acidic or basic head groups onto the PDA molecule, the solubility of the derivatized PDA's were greatly enhanced. They also produced much brighter colors and were more consistent in the assembly of sensors. These results were likely due to the increase in water solubility and homogeneity of mixing between all components. The acid/base PDA's were by far the most sensitive of the amino acid-derived diacetylenes.

Attaching histidine to amine-coupled PDA created materials that could easily turn color, but that could also be re-generated. The particular advantage to this approach is that ordinarily polymerized PDA's turn color, but cannot be used again. The near-neutral pKa of the head group of the histidine materials allows for this advantage.

By placing fluorescent PDA head groups onto the PDA amine-coupled system, calorimetric biosensors can be made with the addition of fluorescent properties. This provides a multi-purpose and more sensitive sensor.

Example 5

Attachment of Ligands

Ligands can be covalently linked to the head groups of self-assembling monomers (e.g, sialic acid linked to diacetylene monomers), can be covalently linked to the surface of polymerized materials (e.g., proteins and antibodies with multiple amine and thiol linkages to the material surface), or can be non-covalently incorporated into the biopolymeric material (e.g., ganglioside incorporated into the membrane of films and liposomes).

The self-assembling monomers can be synthesized to contain a large variety of chemical head-group functionalities using synthesis techniques common in the art. In some embodiments, the ligands are then joined to the self-assembling monomers through chemical reaction with these functionalities using synthesis methods well known in the art. The functionalities include, but are not limited to, esters, ethers, amino, amides, thiols, or combinations thereof. Alternately, many ligands can be incorporated into the self-assembling matrix without covalent linkage to the surfactants (e.g, membrane proteins and molecules with hydrophobic regions such as gangliosides and lipoproteins).

Specific applications of the presently claimed invention are described below to illustrate the broad range of ligands that can be associated with the inventive biopolymeric material. These examples are intended to merely illustrate the broad applicability of the present invention and are not intended to limit the present invention to these particular embodiments.

I. Sialic Acid

Sialic acid was attached as a ligand to diacetylene monomers. Several synthesis methods well known in the art can be used, many of which have general applicability to the attachment of carbohydrates to the inventive biopolymeric materials. In one embodiment, PDA (1.0 g, 2.7 mmol in chloroform) was reacted with N-hydroxy succinimide (NHS) (0.345 g, 3.0 mmol) and 1-(3-dimethylaminopropyl)-3-ethylcarbodiimide hydrochloride (EDC) (0.596 g, 3.1 mmol). The solution was stirred for 2 hours followed by evaporation of the chloroform. The residue was extracted with diethyl ether and water. The organic layer was dried with magnesium sulfate ($MgSO_4$) and filtered. The solvent was then evaporated by rotary evaporation to give 1.21 g of N-succinimidyl-PDA (NHS-PDA). Ethanolamine (0.200 ml, 2.9 mmol) was added to a solution of NHS-PDA (1.21 g in 50 ml of chloroform), followed by triethylamine (0.350 ml, 2.5 mmol) and stirred for two hours at room temperature. The solvent was evaporated and the residue purified by silica gel chromatography (2:1 EtOAc:hexane, $R_f$=0.15) to give 0.99 g of N-(2-hydroxyethyl)-PDA.

Tetraethylene glycol diamine (1.26 g, 6.60 mmol) in 25 ml of chloroform was added to a solution of N-succinimidyl-PDA (0.603 g, 1.28 mmol) in 20 ml of chloroform, dropwise, with stirring, over a period of 30 minutes. The reaction was stirred for an additional 30 minutes before removal of the solvent by rotary evaporation. The residue was dissolved in EtoAc and extracted twice with water. The organic layer was dried with $MgSO_4$, and the solvent removed by rotary evaporation. The extract was purified by silica gel chromatography (20:1 $CHCl_3$:MeOH, $R_f$=0.20) to give 3.72 g of N-(11-amino-3,6,9-trioxyundecanyl)-PDA.

Two ml of acetic anhydride was added to a cooled solution of ethyl-5-N-acetyl-2,6-anhydro-3,5-dideoxy-2-C-(2-propenyl)-D-erythro-L-mannononomate (0.47 g, 1.30 mmol) in 1.7 ml of pyridine under nitrogen, with stirring. The reaction was allowed to warm to room temperature overnight. After 18 hours, the solvents were removed under reduced pressure at ambient temperature, to yield a crude viscous oil. The oil was solidified by repeated evaporation from toluene. The crude solid was flash chromatographed over silica with ethylacetate as eluent, producing 0.58 g of ethyl-5-N-acetyl-4,7,8,9-tetra-O-acetyl-3,5-dideoxy-2-C-(2-propenyl)-D-erythro-L-manno-nononate.

A solution of ethyl-5-N-acetyl-4,7,8,9-tetra-O-acetyl-3,5-dideoxy-2-C-(2-propenyl)-D-erythro-L-manno-nononate (0.38 g, 0.72 mmol) in 10 ml of acetone was cooled to −78° C. while protected from moisture with a $CaCl_2$ drying tube. Ozone was aspirated into the solution until the characteristic blue color persisted for 5 minutes. The reaction was purged with $O_2$ to dissipate the excess $O_3$, followed by warming to 5° C. Excess Jones' reagent (7 drops) was added until a rust orange color persisted, then the reaction was warmed to ambient temperature. After several minutes, ethanol was added dropwise to consume the excess oxidant. The green precipitate was filtered and washed with acetone several times. The combined filtrates were evaporated in vacuuo and dissolved in ethylacetate. The solution was extracted with saturated aqueous $NaHCO_3$ solution three times. The combined aqueous layers were acidified with concentrated HCl and extracted 5 times with methylene chloride. The combined methylene chloride extracts were dried with $MgSO_4$, filtered and evaporated in vacuuo to give ethyl-5-N-acetyl-4,7,8,9-tetra-O-acetyl-3,5-dideoxy-2-C-(acetic acid)-D-erythrol-manno-nonate.

Ethyl-5-N-acetyl-4,7,8,9-tetra-O-acetyl-3,5-dideoxy-2-C-(acetic acid)-D-erythro-L-manno-nonate (0.194 g, 0.35 mmol) was added to a cooled solution (5° C.) NHS (0.058 g, 0.50 mmol) and EDC (0.096 g, 0.50 mmol) in 2 ml of chloroform, under nitrogen. The reaction was warmed to ambient temperature with stirring for 5 hours. The reaction was then diluted with 15 ml of chloroform and washed with 1 N HCl (aq.), twice; saturated (aq.) sodium bicarbonate, twice; and saturated (aq.) sodium chloride, once. The organic layer was dried over $MgSO_4$, filtered, and evaporated to form ethyl-5-N-acetyl-4,7,8,9-tetra-O-acetyl-3,5-dideoxy-2-C-(N-succinimidylacetate)-D-erythro-L-manno-nononate.

Ethyl-5-N-acetyl-4,7,8,9-tetra-O-acetyl-3,5-dideoxy-2-C-(Nsuccinimidylacetate)-D-erythro-L-manno-nononate (0.143 g, 0.22 mmol) and N-(11-amino-3,6,9-trioxyundecanyl)-PDA (0.133 g, 0.24 mmol) were dissolved in 2 ml of chloroform and the reaction was sealed and stirred for 56 hours. The solution was diluted with 15 ml of chloroform and washed with sodium chloride saturated 1N HCl (aq.), twice; saturated (aq.) sodium bicarbonate, twice; and saturated (aq.) sodium chloride, once. The organic layer was dried over $MgSO_4$, filtered, and evaporated to a crude semi-solid. The material was flash chromatographed over silica (20:1 $CHCl_3$:MeOH), producing ethyl-5-N-acetyl-4,5,8,9-tetra-O-acetyl-3,5-dideoxy-2-C-[(N-11'-(PDA)-3',6',9'-trioxyundecanyl) acedamido]-D-erythro-L-manno-nononate.

The sialic acid derived-PDA was formed by dissolving ethyl-5-N-acetyl-4,5,8,9-tetra-O-acetyl-3,5-dideoxy-2-C-[(N-11'-(PDA)-3',6',9'-trioxyundecanyl)acedamido]-D-erythro-L-manno-nononate (0.20 g, 0.19 mmol ) in a solution of 4 ml of water and 0.5 ml of methanol containing 0.1 g dissolved sodium hydroxide. The solution was stirred for 3 hours, and ion exchange resin (Biorad AG 50W-X4 H+ form) was added until the solution was acidic to pH paper. The solution was filtered and the filtrate evaporated in vacuo, producing sialic acid derived-PDA.

II. Carbohydrates

In other embodiments, carbohydrates (i.e., including sialic acid) can be modified by a three-step procedure to produce N-allyl glycosides. The N-allyl glycosides can then be easily linked to other molecules (e.g., PDA) using simple chemical synthesis methods known in the art. This method provides a means to incorporate a broad range of carbohydrates into biopolymeric material (and thus provides a means to detect a broad range of analytes). First, oligosaccharides are dissolved in neat allyl amine (water may be added if necessary and does not adversely affect the yield) producing a 0.5–0.1 M solution. The reaction is stopped and stirred for at least 48 hours. Upon complete conversion of the starting material into amino glycoside product, the solvent is removed by evaporation and the crude solid is treated with toluene and evaporated to dryness several times. The solid is then chilled in an ice bath and a solution of 60% pyridine, 40% acetic anhydride is added to give a solution containing five hundred mole percent excess of acetic anhydride. The reaction is protected from moisture, stirred and allowed to warm to ambient temperature overnight. The solvents are removed by evaporation and the residue is dissolved in toluene and dried by evaporation several times. The crude product is purified by flash chromatography producing the peracetylated NAc-allyl glycoside form of the free sugars.

The peracetylated NAc-allyl glycosides are then dissolved in anhydrous methanol to give a 0.1–0.01 M solution. Several drops of 1 N NaOMe in MeOH are added and the reaction stirred at ambient temperature for 3 hours. Enough Dowex 50 resin (H+ form) is added to neutralize the base, then the solution is filtered and evaporated to dryness (purification by recrystallization can be conducted if desired). The products are the N-allyl glycoslamide form of the carbohydrates. These synthesis reactions have produced the N-allyl glycoslamide forms of a variety of carbohydrates, including, but not limited to, glucose, NAc-glucosamine, fucose, lactose, tri-NAc-Chitotriose, Sulfo Lewis$^x$ analog, and Sialyl Lewis$^x$ analog. Skilled artisans will appreciate the general applicability of this method to the attachment of a broad range of carbohydrates to diacetylene lipids.

III. Ganglioside $G_{M1}$

Ganglioside $G_{M1}$ presents an example of incorporation of a ligand without covalent attachment to the self-assembling monomers. Ganglioside $G_{M1}$ was introduced in the biopolymeric material by combining a solution of methanol dissolved ganglioside $G_{M1}$ (Sigma) with chloroform dissolved PDA, and dried. The ganglioside contains a hydrophobic region that facilitates its incorporation into self-assembling surfactant structures. Thus, when the dried solutions were resuspended in deionized water, the resulting structures contained a mixture of ganglioside and PDA. Liposomes and other forms were produced from the resuspended mixture as described in Example 1. Although the ganglioside does not contain a polymerizable group, the ganglioside became embedded in the polymerized matrix created by the cross-linking of the diacetylenes. Similar methods can be used for the incorporation of other ligands that contain hydrophobic regions (e.g., transmembrane proteins and lipoproteins).

IV. Proteins

The NHS-PDA, as generated above, thiol-linked PDA, and other methods known in the art provide functional groups for the attachment of proteins and antibodies. The NHS or thiol-linked monomers are incorporated into the desired aggregate and polymerized. The NHS or thiol functional groups then provide a surface reaction site for covalent linkage to proteins and antibodies using chemical synthesis reactions standard in the art. In another embodiment, a hydrazide functional group can be placed on PDA, allowing linkage to aldehydes and ketone groups of proteins and antibodies. These embodiments provide a means to incorporate an extremely broad array of proteins and antibodies onto the biopolymeric material. Specific examples are provided below. These examples are intended to merely illustrate the broad applicability of the present invention and are not intended to limit the present invention to these particular embodiments.

A. Hexokinase

NHS-PDA lipid was synthesized as described above. In brief, 1.00 g 10,12-pentacosadiynoic acid (Farchan, Gainesville, Fla.) was dissolved in $CHCl_3$, to which 0.345 g N-hydroxysuccinimide (NHS) and 0.596 g 1-(3-dimethylaminopropyl)-3-ethylcarbodiimide hydrochloride were added. The solution was stirred at room temperature for two hours, followed by removal of $CHCl_3$ using a rotavap. The residue was extracted with EtOAC and water. After separation, the organic layer was dried with $MgSO_4$ and filtered, followed by solvent removal. The raw product was then recrystallized twice with $CHCl_3$, and confirmed by FT-IR.

The 1:1 (molar ratio) PDA/NHS-PDA chloroform solution was spread on the aqueous subphase on a Langmuir-Blodgett trough (KSV mini-trough, KSV Instruments, Inc., Finland) by using a microsyringe (subphase temperature was maintained at 5° C.). The organic solvent was allowed to evaporate by resting the solution for 20 min. The films were compressed to compact monolayer level and then transferred by vertical deposition to glass slides coated with octadecyl-trichlorosilane (OTS). The compression and dipping speed was maintained at 5 mm/min. Three layers were deposited onto the glass slide to provide enough colorimetric signal for detection after polymerization and to ensure the hydrophilic surface was exposed to solution.

The preparation of stable PDA monolayer films before enzyme immobilization is critical for low background and enhanced reproducibility of the sensors. The Langmuir monolayer trough provides a method to measure film stability through the evaluation of the surface collapse pressure of the monolayers. It was found that the mixed films (i.e., films with PDA and NHS-PDA) appear to be much more stable than the monolayers consisting of one component and thus more suitable for enzyme immobilization. For instance, the collapse pressure for 1:1 NHS-PDA/PDA monolayer at 5° C. was 57 mN/m, while NHS-PDA and PDA monolayers collapsed at 34 and 28 nN/m, respectively. Although it is not necessary to understand the mechanism in order to use the present invention, and it is not intended that the present invention be so limited, it is contemplated that the interactions are more favorable in these mixed monolayers, presumably due to the optimal spatial arrangements that allow head groups of different size to pack closely.

Besides mechanical stability, the monolayers should possess desirable optical properties (i.e., high color intensity) to be suitable as sensors. Film quality, in this particular case color intensity, was studied at different deposition pressures. It was found that films made at 40 mN/m gave the best transfer rate and color intensity. Therefore, the 1:1 NHS-PDA/PDA films obtained at this transfer pressure were selected for modification with hexokinase.

Yeast hexokinase suspension (E.C. 2.7.1.1, from Boehringer Mannheim GmbH, Germany) was spun in a microcentrifuge to remove saturated ammonium sulfate. The protein was resolubilized in 0.1 M phosphate buffer (pH 8.0) to give approximately 1 mg/ml concentration, and dialyzed against the same buffer using a Slide-A-Lyzer dialysis cassette (Pierce) for 3 hours. The PDA monolayer slides were cut into 0.7 cm×2.5 cm rectangular pieces, and incubated in the hexokinase solution at 4° C. for 1 hr. Prolonged incubation was found to result in decreased color intensity, presumably due to the shedding of LB monolayers during the chemical cross-linking reaction. The monolayer chips were then rinsed with deionized water and immersed into 0.1 M ethanolamine for 10 min to terminate the reaction. The chips were rinsed again with deionized water and air dried. Polymerization was conducted by irradiating the films with a hand held UV lamp. The irradiation time was 6 min. each side. Extended irradiation results in irreversible color change to red.

B. Antibodies

Commercially obtained diacetylene was first filtered to remove the insoluble impurities (e.g., polymerized form) and converted chemically to NHS-PDA as described above. Appropriate amounts of NHS-PDA and other forms of PDA derivatives (e.g., dopants or ligands) were mixed to give the desired molar ratio. The solution was dried using $N_2$ gas, so a thin layer of white material deposited on the bottom of the vial. Deionized water was added to bring the total concentration of lipid to approximately 1 mM. The solution was sonicated by using either a probe sonicator for approximately 20 minutes or a bath sonicator for over 2 hours until a clear solution was obtained. The solution was filtered through 5 μm filter while hot, then stored at 4° C. overnight.

Prior to cross linking, 0.1 M phosphate buffer (pH 8.5) was added to the liposome solution. Antibody dissolved in a similar buffer was then added, and the solution was stored at 4° C. overnight. Excess antibody was removed by either centrifugation or dialysis. When centrifugation was used, the pellet was resonicated gently using an ice bath. Following association of the antibody to the sonicated material, polymerization was conducted as described for liposomes in Example 1.

Antibodies can also be attached to biopolymeric material by hydrazides. In some embodiments, this may be preferred to NHS-coupling because NHS may react at the Fab' region of the antibody, blocking binding to analytes. The hydrazide method causes attachment of the Fc region of the antibodies to the biopolymeric material, leaving available, the binding region. In the hydrazide method, hydrazide-PDA lipids were produced, and unpolymerized liposomes are generated (e.g., 20% hydrazide PDA/80% TRCDA). Using Centricon 50 filters, 500 μl of stock antibody solution was washed by adding an equal volume of 123 mM sodium citrate (pH 5.5) and spun down at 4000 rpm for 9 minutes. The filtering step was repeated two more times. Four hundred microliters of the antibodies in citrate buffer were then oxidized by incubating with 25 μl of sodium periodate for 2 hours at 22° C. After the 2 hours, the reaction was quenched by adding 50 μl of N-acetylmethionine. Next, 300 μl of liposomes, 150 μl citrate buffer, 400 μl water, and 200 μl of oxidized antibodies were incubated overnight at 22° C. Uncoupled antibodies are removed from the liposomes by using Centricon 500 filters and washing with 900 μl Tris buffer (pH 9.0) and centrifugation at 4000 rpm for 2 minutes. After multiple washes, the sample is dilute (if necessary) with Tris buffer to make a 0.2 mM (or less) liposome solution.

V. Others (Amino Acids, Nucleotides, Etc.)

As described above and shown in FIG. 9, the attachment of amino acids though amine linkage to diacetylenes has been accomplished. A variety of other means of attaching amino acids to lipids are also known in the art.

The generation of PDA-linked ligands containing a variety of different chemical head-group species is described in Example 7, for VOC detection. These examples demonstrate the derivation of PDA with a broad range of chemical head groups such as hydrophilic uncharged hydroxyl groups, primary amine functionalities, amino acid derivatives, and hydrophobic groups. These and other modifications are generated by synthesis methods known in the art.

In other embodiments, various other surfactant-linked ligands can be prepared using condensation reactions involving an activated carboxylic acid group and a nucleophilic amino or hydroxy. PDA can be activated with trimethylacetylchloride under anhydrous conditions to form an active asymmetric anhydride. The anhydride can be treated with excess ethylene diamine or ethanolamine to form ethylenediamino-PDA (EDA-PDA) or ethanolamine-PDA (EA-PDA), respectively. One and a half mole equivalents of triethylamine are added as a catalytic base and reactions are allowed to proceed for three hours at room temperature. EDA-PDA and EA-PDA are chromatographically purified using a silica gel column and a chloroform/methanol gradient. The EDA-PDA or EA-PDA are then be condensed with free carboxylic acid containing ligands (chemically activated as above) to form the ligand-linked polymerizable surfactants. Representative examples of ligands that can be prepared by this method include, but are not limited to, carbohydrates, nucleotides, and biotin.

The art contains numerous other examples of successful linkage or association of molecules to lipids and membranes. The self-assembling monomers associated with ligands can be of modified chain length or may consist of double or multiple chains. These various combinations of ligands and monomers provide an extremely broad array of biopolymeric materials appropriate for the interaction with a broad range of analytes, with the desired colorimetric response, selectivity, and sensitivity.

Example 6

Colorimetric Analysis

I. Visual Detection

In preferred embodiments, the colorimetric changes of the biopolymeric materials of the present invention are detected though simple observation by the human eye. Because of the simplicity of the observation, this function can be accomplished by an untrained observer such as an at-home user.

II. Visible Absorption Spectroscopy

In some embodiments it may be preferred to obtain accurate quantitative data of the calorimetric responses or to record subtle changes or faint signals undetectable by the human eye. Spectroscopy means may be applied to acquire such data.

Visible absorption studies were performed using a Hewlett Packard 8452A Diode array spectrophotometer. For PDA material (i.e., films and liposomes), the calorimetric response (CR) was quantified by measuring the percent change in the absorption at 626 nm (i.e., which imparts the blue color to the material) relative to the total absorption maxima.

In order to quantify the response of a biopolymeric material to a given amount of analyte, the visible absorption spectrum of the biopolymeric material without the analyte was analyzed as $$B_o = I_{626}/(I_{536} + I_{626})$$

where $B_o$ is defined as the intensity of absorption at 626 nm divided by the sum of the absorption intensities at 536 and 626 nm. The biopolymeric material exposed to analytes were analyzed in the same manner as $$B_a = I_{626}/(I_{536} + I_{626})$$

where $B_a$ represents the new ratio of absorbance intensities after incubation with the analyte. The colorimetric response (CR) of a liposome solution is defined as the percentage change in B upon exposure to analyte.

$$CR = [(B_o - B_a)/B_o] \times 100\%$$

Example 7

Detection of Analytes

The broad range of biopolymeric materials taught by the present invention allow for the detection of numerous analytes. Such analytes range from complex biological organisms (e.g., viruses, bacteria, and parasites) to simple, small organic molecules (e.g., alcohols and sugars). Specific applications of the presently claimed invention are described below to illustrate the broad applicability of the invention to a range of analyte detection systems and to demonstrate its specificity, and ease of use. These examples are intended to merely illustrate the broad applicability of the present invention. It is not intended that the present invention be limited to these particular embodiments.

I. Detection of Influenza Virus

The presently claimed invention provides superior means of detecting influenza compared to currently available technology. Immunological assays are limited because of the antigenic shift and drift exhibited by the virus. The presently claimed invention detects all varieties of influenza and thus a determination of a patient's exposure to influenza will be definitive, and not limited to a particular strain. Indeed, even newly evolved, uncharacterized influenza strains can be detected.

Figure 27:
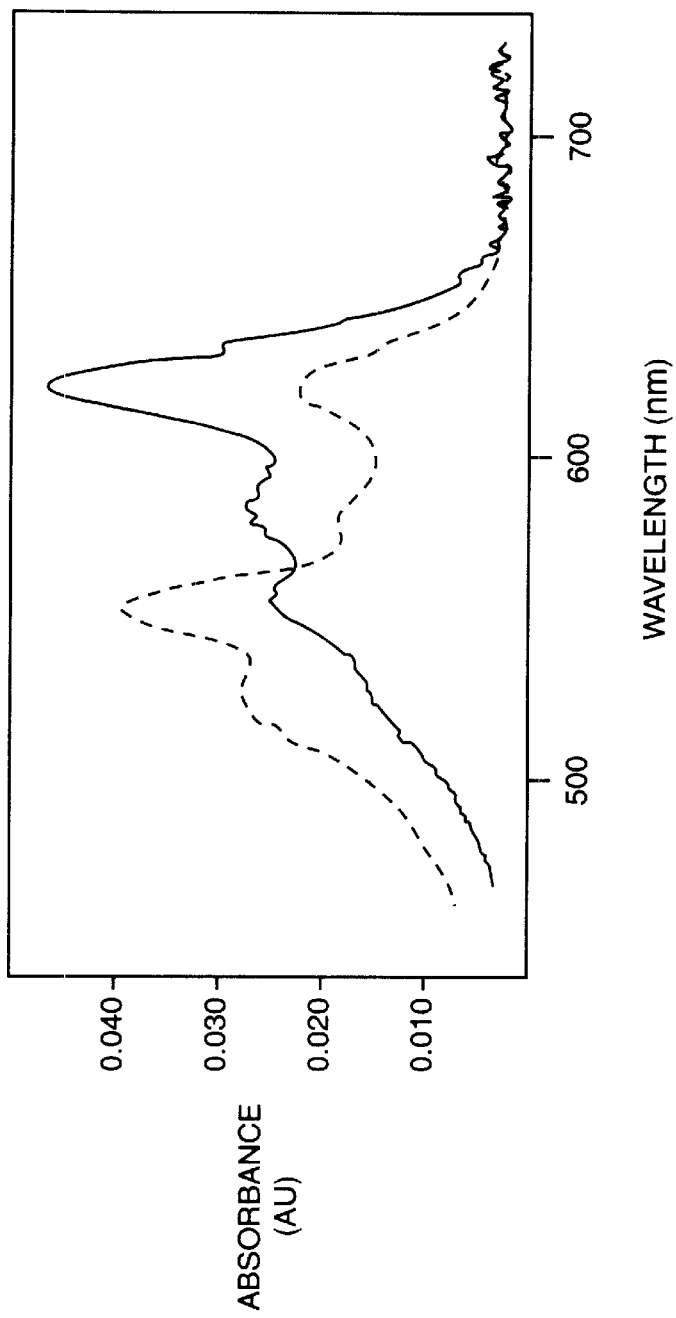
FIG. 27 shows the visible absorption spectrum for sialic-acid containing films before (solid line) and after (dashed line) exposure to influenza virus.
Figure 28:
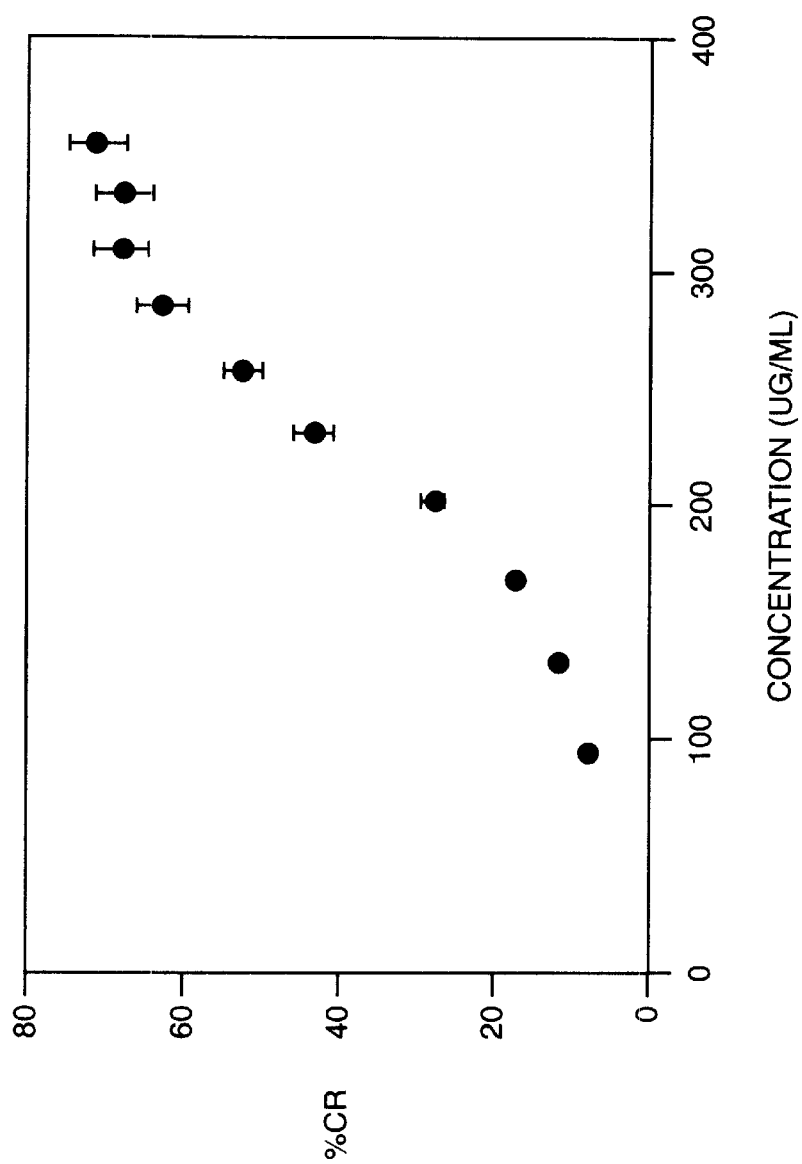
FIG. 28 shows the color transition of ganglioside $G_{M1}$-containing liposomes in response to varying concentrations of cholera toxin.

Sialic acid-linked biopolymeric material was generated as described in Examples 1 and 5. The materials were exposed to influenza virus and colorimetric information was observed visually or with spectroscopy as described in Example 6, and shown in FIG. 27 for blue (solid line) and red phase (dashed line) material, respectively. For liposomes, a 1–10% mixture of sialic acid-linked PCA was incorporated, as previous studies indicated that optimum viral binding occurs for mixtures of 1–10% in liposomes (Spevak et al., J. Am. Chem. Soc. 161: 1146 [1993]).

For silicate glass-entrapped liposomes (i.e., liposomes prepared by the sol-gel method), it was found that 5,7-DCDA provided a more vivid calorimetric response than 10,12-PCA. It is believed that the improved response with 5,7-DCDA was related to the size restrictiveness of the sol-gel material and the topochemical nature of the conformational changes responsible for the chromatic transitions, although an understanding of the mechanism is not required to practice the present invention.

In one experiment, irradiation of a sialic acid-linked PCA containing liposome solutions for 5–10 minutes resulted in the formation of deeply blue colored liposomes, while polymerization for between 10 and 30 minute resulted in a purple color. When influenza virus was added to the liposomes, the material changed to a pink or orange color, depending on whether the initial preparation was blue or purple, respectively. These color changes were readily visible with the naked eye.

Competitive inhibition experiments were conducted to demonstrate the specificity of the ligand-analyte interaction. Experiments were performed as described above, but with a slight excess of a-O-methyl-neuramatic acid, a known inhibitor for influenza virus hemagglutination. The presence of the inhibitor resulted in no detectable color change of the biopolymeric material.

It is contemplated that the influenza virus detection system include additional ligands that recognize and differentiate influenza strains or serotypes from one another and from other pathogens.

The sialic-acid containing biopolymeric materials of the present invention provide means of detecting many other pathogens. In addition to influenza virus, sialic acid has the capability of detecting other analytes including, but not limited to, HIV, chlamydia, reovirus, *Streptococcus suis*, Salmonella, Sendai virus, mumps, newcastle, myxovirus, and *Neisseria meningitidis*.

II. Detection of Cholera Toxin

Cholera toxin is an endotoxin of the Gram-negative bacterium *Vibrio cholerae* that causes potentially lethal diarrheal disease in man. Cholera toxin is composed of two subunits: A (27 kDa) and B (11.6 kDa) with the stoichiometry $AB_5$. The B components bind specifically to $G_{M1}$ gangliosides on cell surfaces, ultimately leading to translocation of the $A_1$ fragment through the membrane. Cholera toxin can be recognized by $G_{M1}$-containing supported lipid membranes and polymerized Langmuir-Blodgett films containing $G_{M1}$ and a carbohydrate 'promoter' lipid (ie., sialic acid-derived diacetylenes) as shown by Pan and Charych (Langmuir 13: 1365 [1997]).

Ganglioside $G_{M1}$, cholera toxin from *Vibrio Cholerae*, human serum albumin, and wheat germ agglutinin were purchased from Sigma. 5,7-docosadiynoic acid was synthesized. Deionized water was obtained by passing distilled water through a Millipore μF ultrapurification train. Solvents used were reagent grade. The ganglioside $G_{M1}$ was mixed at 5 mol % with the diacetylene "matrix lipid" monomers. Liposomes were prepared using the probe sonication method and polymerized by UV irradiation (254 nm). The conjugated ene-yne backbone of polydiacetylene liposomes results in the appearance of a deep blue/purple solution The visible absorption spectrum of the freshly prepared purple liposomes is shown in FIG. 25.

For the colorimetric assay, cholera toxin was diluted to 1 mg/ml in 50 mM Tris buffer, pH 7.0. In a 500 μl glass cuvette, blue phase liposomes produced as above were diluted 1:5 in 50 mM Tris buffer, pH 7.0. The liposomes were pre-incubated in the buffer for 15–30 minutes to ensure stability of the blue phase prior to the addition of cholera toxin. No color changes were observed during this period.

Cholera toxin was added to the cuvette by the method of successive additions. After each addition, the contents were mixed and the visible absorption spectrum was recorded as a function of time. Typically, 95% of the absorption changes were observed to occur within the first 2 minutes after addition of toxin as shown in FIG. 26. After each experiment, the contents of the cuvette were transferred to a single well of a white microtiter plate. The pink-orange color of the cholera-treated liposomes was verified visually with a blue negative control.

A negative response was observed if the ganglioside $G_{M1}$ ligand was removed from the liposomes. Similarly, negative responses were obtained when comparable quantities of other proteins besides cholera toxin were added to the $G_{M1}$-containing liposomes. These include human serum albumin, avidin, and wheat germ agglutinin.

Kinetic experiments indicate that greater than 95% of the color change occurs within the first two minutes of adding the toxin. As shown in FIG. 28, the color transition is not an all or nothing effect but depends on the quantity of toxin titrated into the solution. The sigmoidal behavior suggest cooperativity of the colorimetric transition. Although it is not necessary to understand the mechanism in order to use the present invention, and it is not intended that the present invention be so limited, it is contemplated that this may indicate that the binding itself is cooperative in the sense that binding of toxin to the $G_{M1}$ ligand makes the binding of subsequent toxins more favorable. Alternatively this result might more appropriately be understood in terms of the lipid-polymer side chain conformation and its result on the effective conjugated length of the polydiacetylene backbone. Once the effective conjugated length is reduced as a result of toxin binding, subsequent perturbation of the remainder of the lipid-polymer backbone becomes more favorable.

III. Detection of *E. Coli* Toxin

Liposomes were prepared with 5% by mole of $G_{M1}$ and 95% 5,7-DCDA. For the colorimetric assay, *E.coli* toxin (Sigma) was spun through a 30 K molecular weight cutoff filter at 2000×g at 15° C. to remove salts. The protein was re-diluted in 50 mM Tris buffer pH 7.0 to a final concentration of 1 mg/ml.

FIG. 29 shows the visible absorption spectrum of the polymeric liposomes containing 5% $G_{M1}$ ligand and 95% 5,7-DCDA prior to exposure to *E. Coli* toxin. The liposomes were diluted in 50 mM Tris buffer, pH 8.0 to a final concentration of 0.2 mM in a plastic disposable cuvette. The solution in the cuvette appeared purple to the naked eye.

Figure 29:
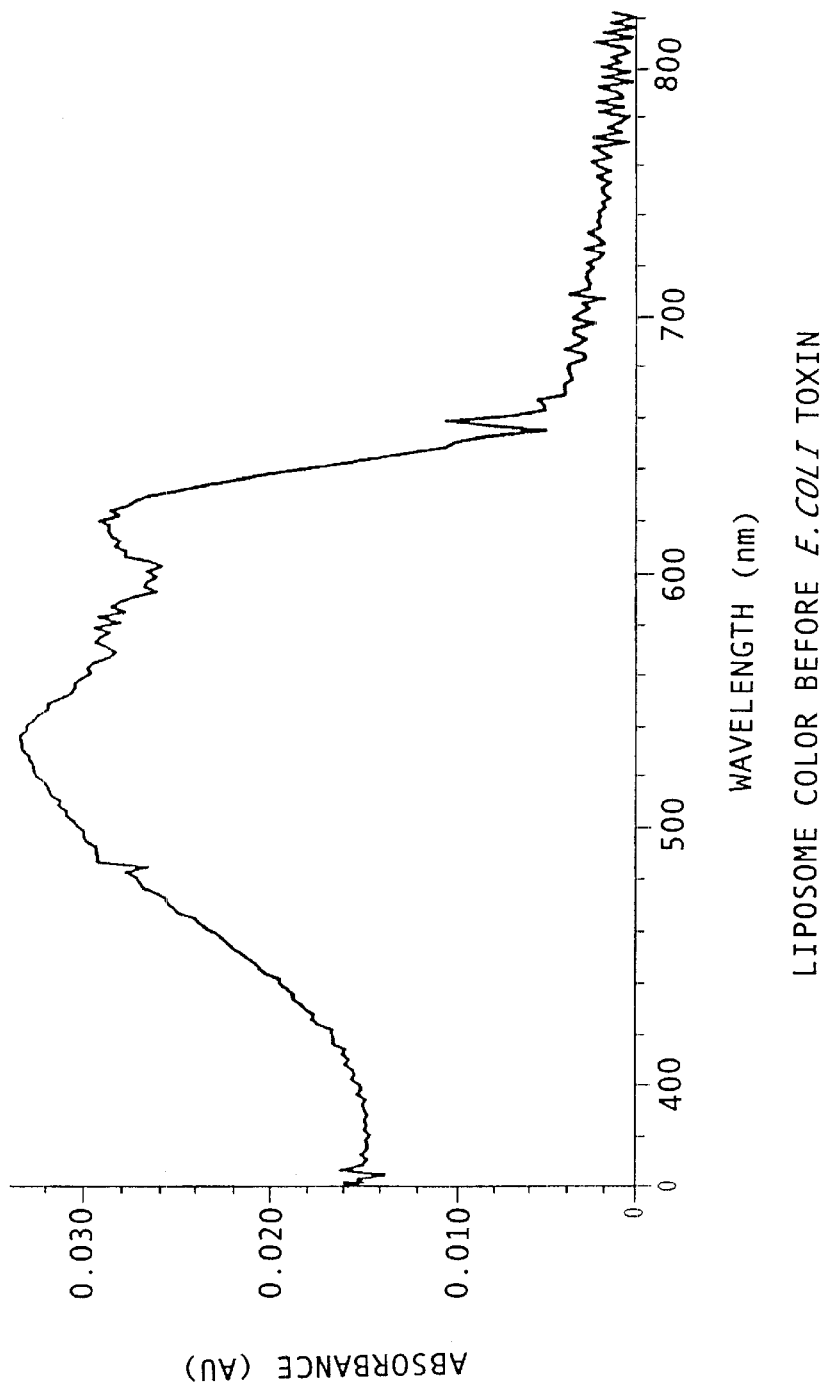
FIG. 29 shows the visible absorption spectrum of the polymeric liposomes containing 5% $G_{M1}$ ligand and 95% 5,7-DCDA.
Figure 30:
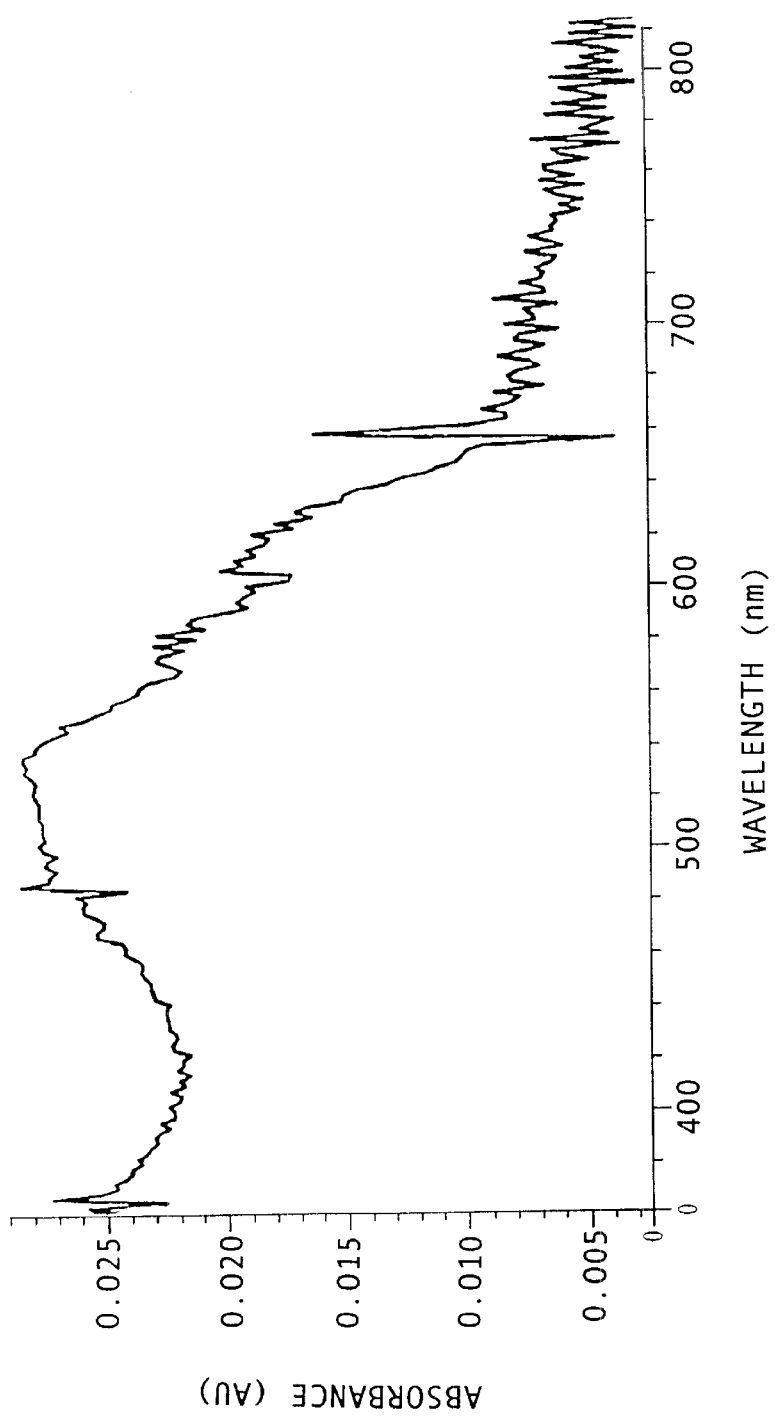
FIG. 30 shows the visible absorption spectrum of the material in FIG. 29 following exposure to *E. coli* toxin.

To the liposomes solution in the cuvette, 40 μl of the above *E. coli* toxin was added and the sample allowed to incubate for 10 minutes. The visible absorption spectrum was again recorded as shown in FIG. 30. The solution in the cuvette appeared pink to the naked eye after the addition of the toxin compared to a purple color before the addition. The absorption spectra of FIGS. 29 and 30 confirm the color changes observed.

IV. Detection of Other Pathogens

The present invention may also be used to detect a variety of other pathogens. Ligands, specific for a large number of pathogens (e.g., carbohydrates, proteins, and antibodies) can be incorporated into the biopolymeric material using routine chemical synthesis methods described above and known in the art. Some of the examples of pathogen detection systems are presented below to demonstrate the variety of methods that can be applied using the present invention and to demonstrate the broad detecting capabilities of single ligand species (e.g., sialic acid).

The sialic acid derivated material of the present invention has been used to detect the presence of parasites such as Plasmodium (i.e., the etiologic agent that causes malaria). In these embodiments, the genetically conserved host binding site was utilized. PDA films containing sialic acid as described above were exposed to solutions containing malaria parasites and erythrocytes. After overnight exposure to the parasites, the films became pink in color. The color response (CR) in each case was nearly 100%. It is contemplated that the system be used in conjunction with other testing material (e.g., arrays of biopolymeric material with various ligands) to identify and differentiate the presence of particularly virulent species or strains of Plasmodium (e.g., *P. falciparum*) or other pathogens.

In yet other embodiments, antibodies were used as ligands to successfully detect the presence of *Neisseria gonorrhoeae* and *Vibrio vulnificus*. The incorporation of the antibodies into the biopolymeric material is described in Example 5.

As is clear from these examples, the present invention provides a variety of means to detect a broad range of pathogens, including bacteria, viruses, and parasites.

V. Detection of Volatile Organic Chemicals (VOCs)

Certain embodiments of the presently claimed invention provide means to calorimetrically detect volatile organic compounds (VOCs). Most of the current methods of VOC detection require that samples be taken to laboratory facilities where they are analyzed by gas chromatography/mass spectroscopy. Some of the on-site methodologies require large, bulky pieces of equipment such as that used in spectroscopic analysis. While these methods are excellent for providing quantitation and identification of the contaminant, they cannot ensure the safety of the individual worker. In one embodiment, the present invention provides a badge containing immobilized biopolymeric material that signals the presence of harmful VOCs and provides maximum workplace safety within areas that contain VOCs. The badge is easy and simple to read and requires no expertise to analyze on the part of the wearer. The color change of the badge signals the individual to take appropriate action. The badges reduce costs and improve the efficiency of environmental management and restoration actions, significantly reducing down-time due to worker illness by preventing over-exposure to potentially harmful substances.

Two main approaches toward VOC detection have been adopted by various groups. The first involves traditional analytical techniques such as GC/MS that have been modified for VOC detection (i.e., an instrument-based approach) (Karpe et al., J. Chromatography A 708: 105 [1995]). However, these methods are expensive, complicated, and do not lend themselves to field or home use. The second involves the coupling of lipid membranes to detector surface (s) (i.e., an organic-device approach). In the past decade, several sensor devices that involve the coating of a piezoelectric mass balance with an organic film have been investigated. Because of the non-selective nature of the coating, these have been investigated in an array. These sensors, such as the quartz crystal microbalance (QCM) and the surface acoustic wave (SAW) devices (See e.g., Rose-Pehrsson et al., Anal. Chem. 60: 2801 [1988]), have linear frequency changes with applied mass. By applying a polymer or other coating to the crystal, a sensor based on the QCM or SAW is constructed. The complex electronics involved in the use of SAW, QCM, and electrode based systems makes these approaches less amenable to use as personal safety devices.

The present invention differs from these methods in that signal transduction is an integral part of the organic layer structure rather than signal transduction to an electronic device. In addition, embodiments of the present invention facilitate optical detection of the signal rather than electronic detection. Furthermore, the present invention provides flexibility in material design, allowing easy immobilization into a small cartridge (e.g., a badge) rather than being burdened with the need for electronic equipment.

Figure 31:
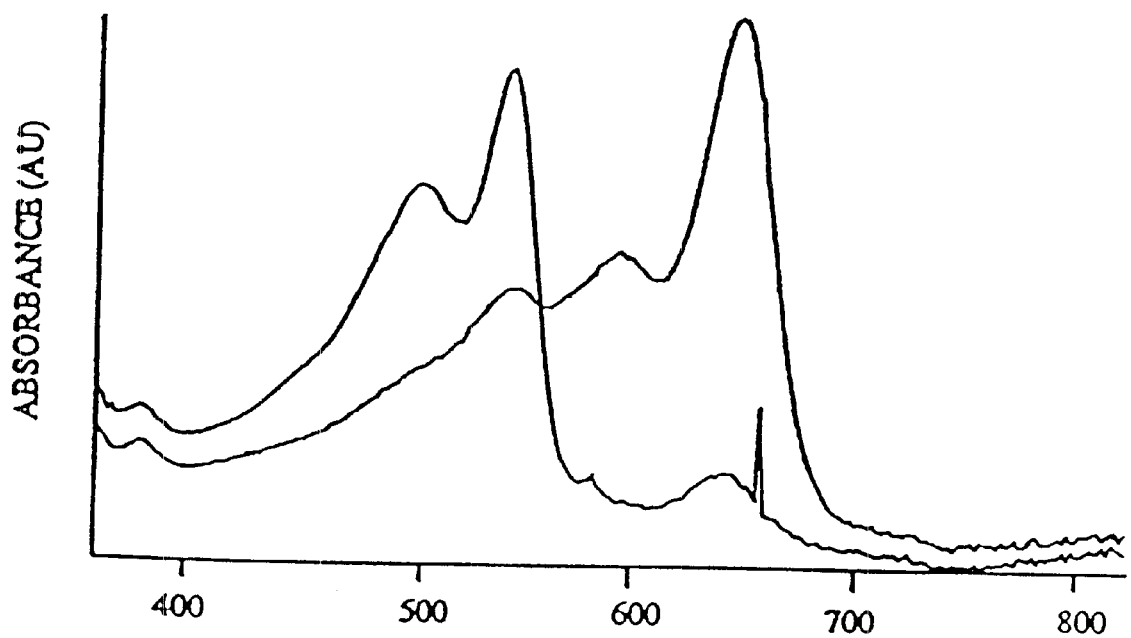
FIG. 31 shows the absorption spectrum of a PCA film in before (line a) and after exposure to 1-octanol dissolved in water (line b).
Figure 32:
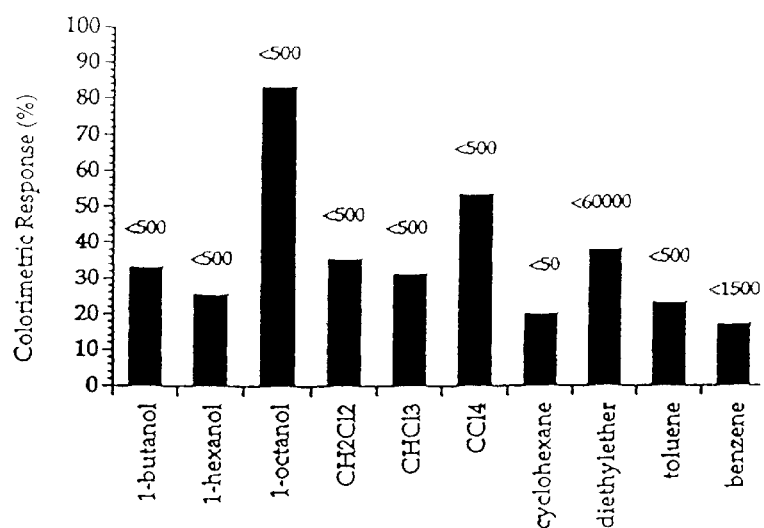
FIGS. 32A and 32B shows a bar graph indicating colorimetric responses of PDA material to various VOCs (A) and a table showing the concentration of the VOCs (B).

During the development of the present invention, it was observed that the interaction of volatile organic solvents with certain lipid-polymer membranes produced a strong blue to red color transition. FIG. 31, curve a, shows the absorption spectrum of a PCA film in blue phase. The film changes to red phase PCA, curve b, upon exposure to approximately 500 ppm of 1-octanol dissolved in water. For a variety of solvents analyzed, the degree of color change was generally dependent upon the concentration of the solvent and also increased with the extent of halogenation and aromaticity. In this study, a single component thin membrane film of PCA was prepared and polymerized to the blue state by UV exposure (254 nm). These materials were more sensitive to water-immiscible solvents than to water-miscible solvents. For the miscible alcohols, it was found that the response increased dramatically for isopropanol compared to ethanol, perhaps because of a greater extent of solvent intercalation into the membrane. For the water-immiscible solvents, measurable color changes were obtained at 0.05 wt % (500 ppm). Within this group, a similar trend was observed with increased alcohol chain length, as well as with increased extent of chlorination. A wide variety of water-immiscible solvents were examined at their water-saturation concentration, as shown in FIG. 32A and B. As indicated in section B, each concentration is different. In FIG. 32A, the y-axis represents the colorimetric response, or the extent of blue-to-red conversion. The numbers above the bar represent an upper limit to the detection in ppm. For many of these solvents, it is clear that solvent concentrations well below 500 ppm can be detected.

Figure 33:
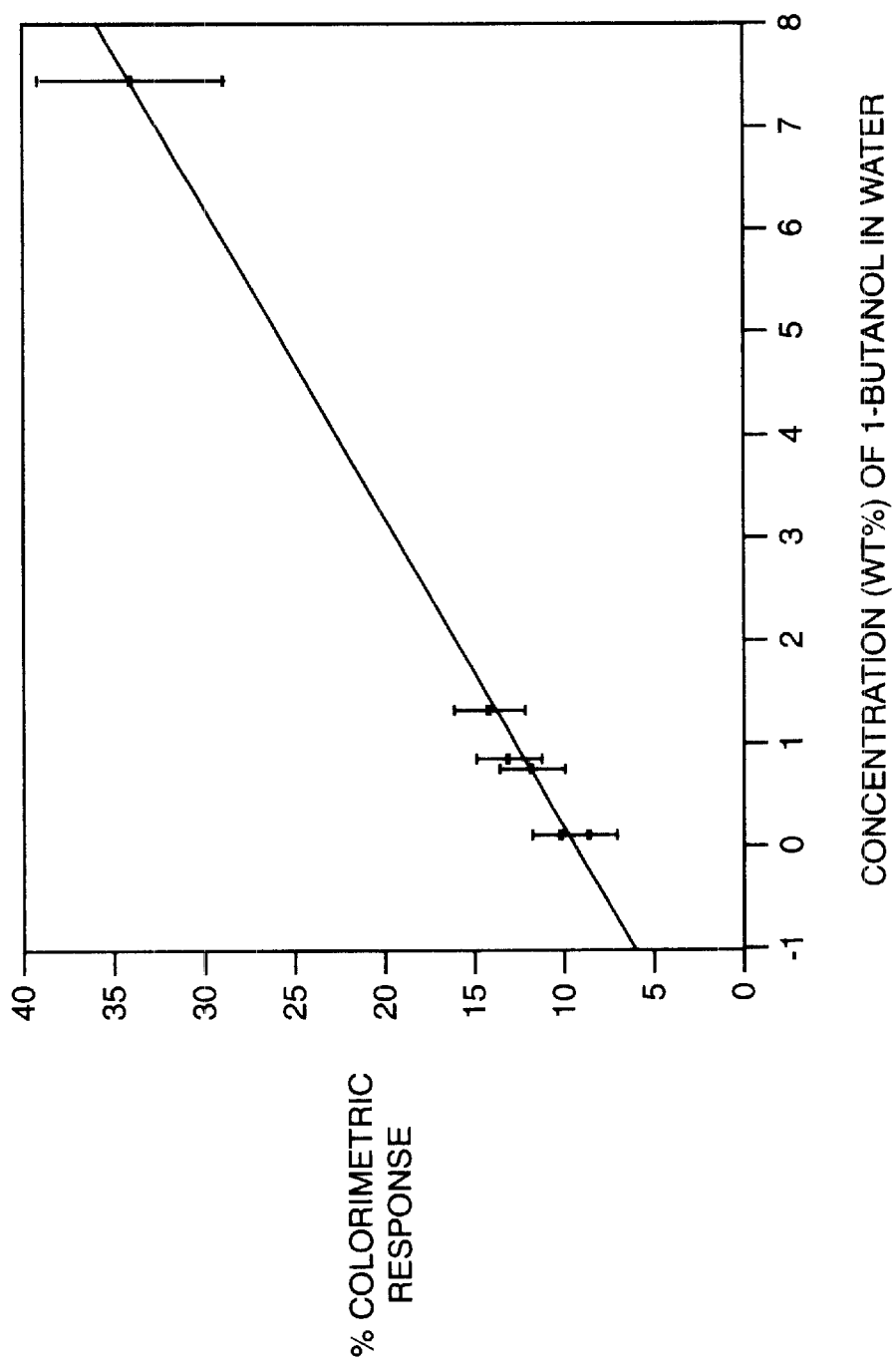
FIG. 33 shows a graph comparing calorimetric responses of biopolymeric material to 1-butanol to the concentration of 1-butanol.

For the immiscible solvents that have a relatively high solubility in water, it was possible to examine the effect of solvent concentration on the calorimetric response. A linear relationship was found to exist between the colorimetric response and solvent concentration in water in the range of 0.05–8 wt % as shown in FIG. 33 for 1-butanol.

The pharmaceutical industry has an ongoing need for solvent sensors, as pharmaceutical compounds are typically manufactured through organic chemical reactions that take place in the presence of solvents. Before packaging of a drug for use in humans or other animals, the solvent must be completely driven off (Carey and Kowalski, Anal. Chem. 60: 541 [1988]). The currently used method for detecting these VOCs uses energy intensive dryers to blow hot air across the drug and piezoelectric crystal arrays to analyze the evaporation of the various solvents (Carey, Trends in Anal. Chem. 13: 210 [1993]). The presently claimed invention provides a calorimetric based approach that greatly simplify these measurements.

In addition, interest in analytical methods for the quantitation of VOCs in non-industrial indoor air environments has increased dramatically in the last several years. This is due primarily to a heightened awareness of emissions from common household appliances or office equipment, as well as trends in controlled building ventilation. Companies that produce consumer products have an interest in serving this increased need by providing indoor air monitors that can deduce the presence of hazardous VOCs in-situ, without the need for air sampling and subsequent laboratory analysis. The presently claimed invention provides embodiments to achieve such means. Indeed, embodiments of the present invention provide for enhanced air sampling, and the cartridges may be connected to small, portable, battery-operated pumps for personal or general air sampling.

VI. Detection of Other Small Organic Molecules

Figure 34:
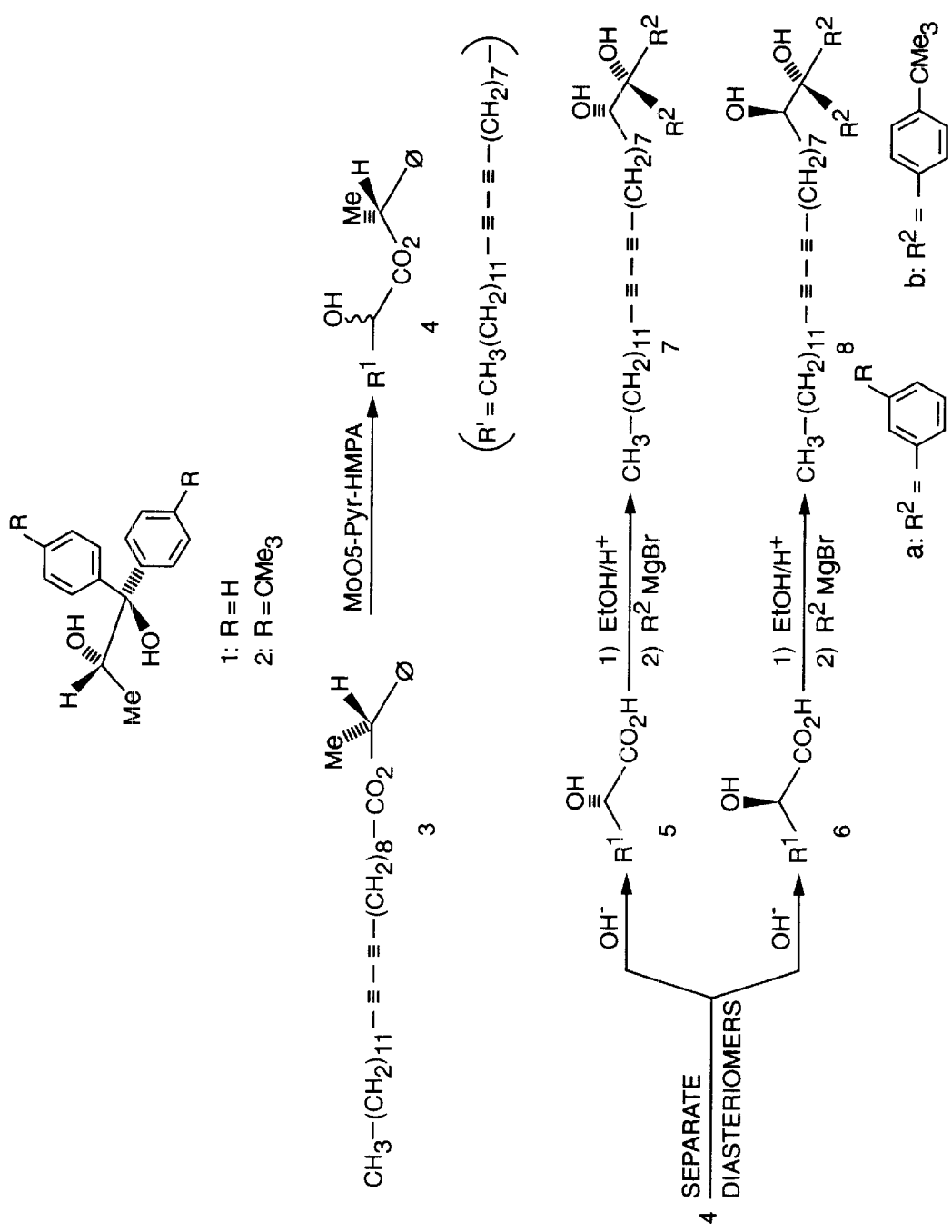
FIG. 34 shows compounds and synthesis schematics for producing PDA derivatives for the detection of small organic compounds.
Figure 35A:
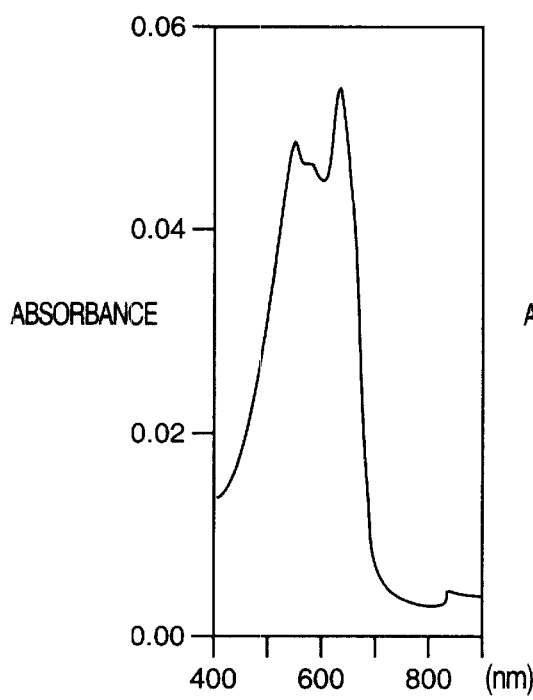
FIGS. 35A–35D show the UV-Vis spectra of a hexokinase modified PDA monolayer upon addition of glucose as a function of incubation time at (A) background, (B) t=0.02 min, (C) t=30, and (D) at t=60 min.
Figure 35B:
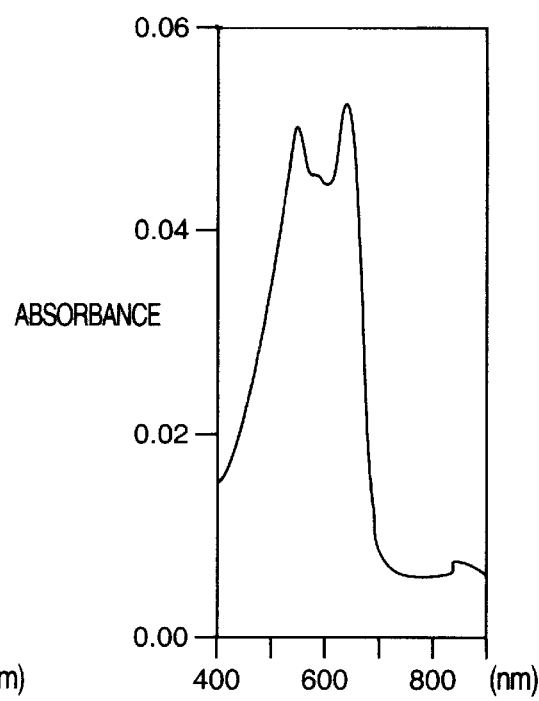
Figure 35C:
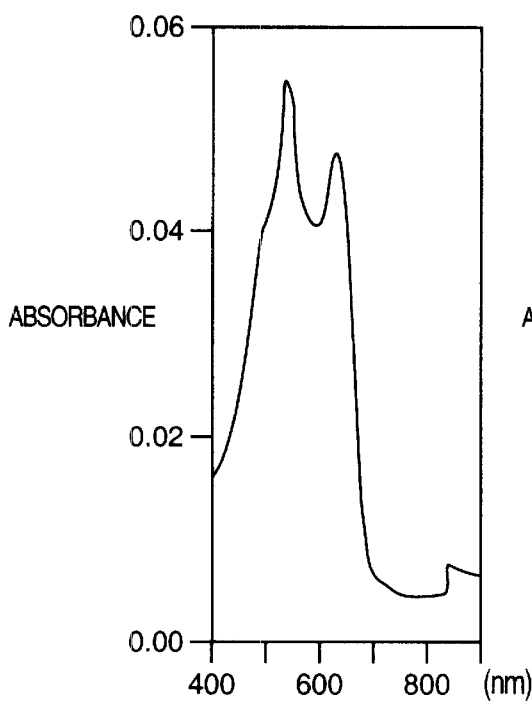
Figure 35D:
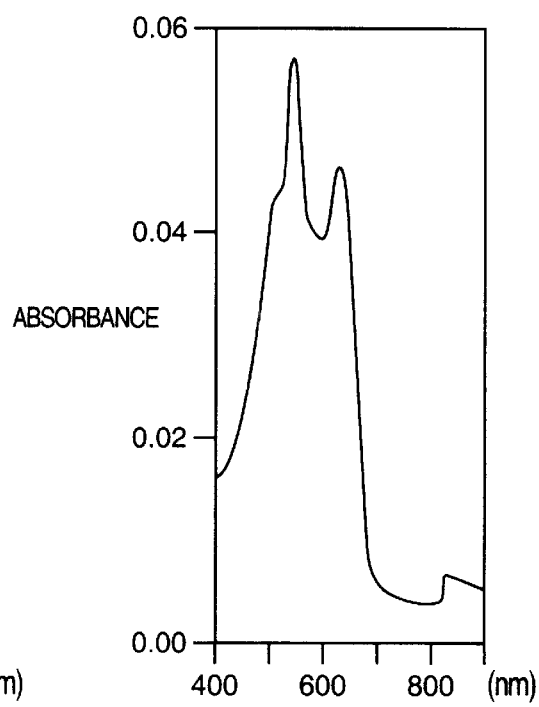

Certain inclusion compounds, or clathrates, such as compounds 1 and 2 in FIG. 34 have been shown to be highly selective sorbents for organic solvent vapors (Ehlen, et al., Angew, Chem. Int. Ed. Engl. Vol. 32, p. 110 [1993]). For example, compound 1 has a pronounced affinity for dioxane and little affinity for butanol, acetone, methanol, 2-propanol, cyclohexane, toluene, and water. Compound 2 on the other hand, shows a pronounced affinity for 1-butanol over the same group of solvents.

The purpose of this example is to show the development of a new class of functional materials that specifically trap small organic compounds and report the entrapment event by a colorimetric change which can be detected visually. These material act as simple color-based sensor devices that detects the presence of compounds such as solvents or other toxic pollutants in air or water streams.

The first step involves the synthesis of lipid diacetylene analogs of compounds 1 and 2 as shown in FIG. 34. In this figure, the enantiometrically pure ester of PDA (pentacosadiynoic acid) 3 is hydroxylated via molybdenum peroxide oxidation to alcohol 4. Diasteriomers are separated and the ester is hydrolyzed to chiral lactate analogs 5 and 6. The ethyl esters are formed and treated with Grignard reagents to give the desired chiral lipid analogs 7 and 8. Variation in the R groups result in a wide variety of new materials in which the specific entrapment capabilities are reviewed.

The monomer-lipid clathrate is ordered and compressed on the water surface using a Langmuir-Blodgett film apparatus. Polymerization of the monolayer by UV irradiation yields the blue colored material as described above. The film is lifted onto a hydrophobized microscope slide. Exposure of these materials to analytes (e.g., 1-butanol or dioxane) produces a colorimetric response.

VII. Detection of Glucose with Hexokinase Ligands

For the calorimetric measurements, the hexokinase modified films, as described above, were placed onto silanized glass cover slides for the purpose of measuring the optical properties. The biosensor coated glass cover slides were placed in glass cuvettes and the UV-Vis spectra of hexokinase modified films were recorded in 0.1 M phosphate buffer (pH 6.5). Measurements taken in this buffer condition were considered background. Addition of glucose, or other sugar substitutes, occurred directly in the cuvettes. FIG. 35 shows the UV-Vis spectra of a hexokinase modified PDA monolayer upon addition of glucose as a function of incubation time, showing (A) background (0.1 M phosphate buffer, pH 6.5); (B) at t=0.02 min after addition of 10.0 mM glucose; (C) at t=30 min after addition of 10.0 mM glucose; and (D) at t=60 min after addition of 10.0 mM glucose.

It is clear that addition of glucose provokes an immediate response as reflected by the increase in absorbance at 550 nm. The response increases with time, reaching its peak at 60 minutes. The colorimetric response (CR), defined above, was 5.2, 13.7, and 17.1% for t=0.02, 30, and 60 minutes, respectively. The color change was irreversible under these conditions.

Figure 36:
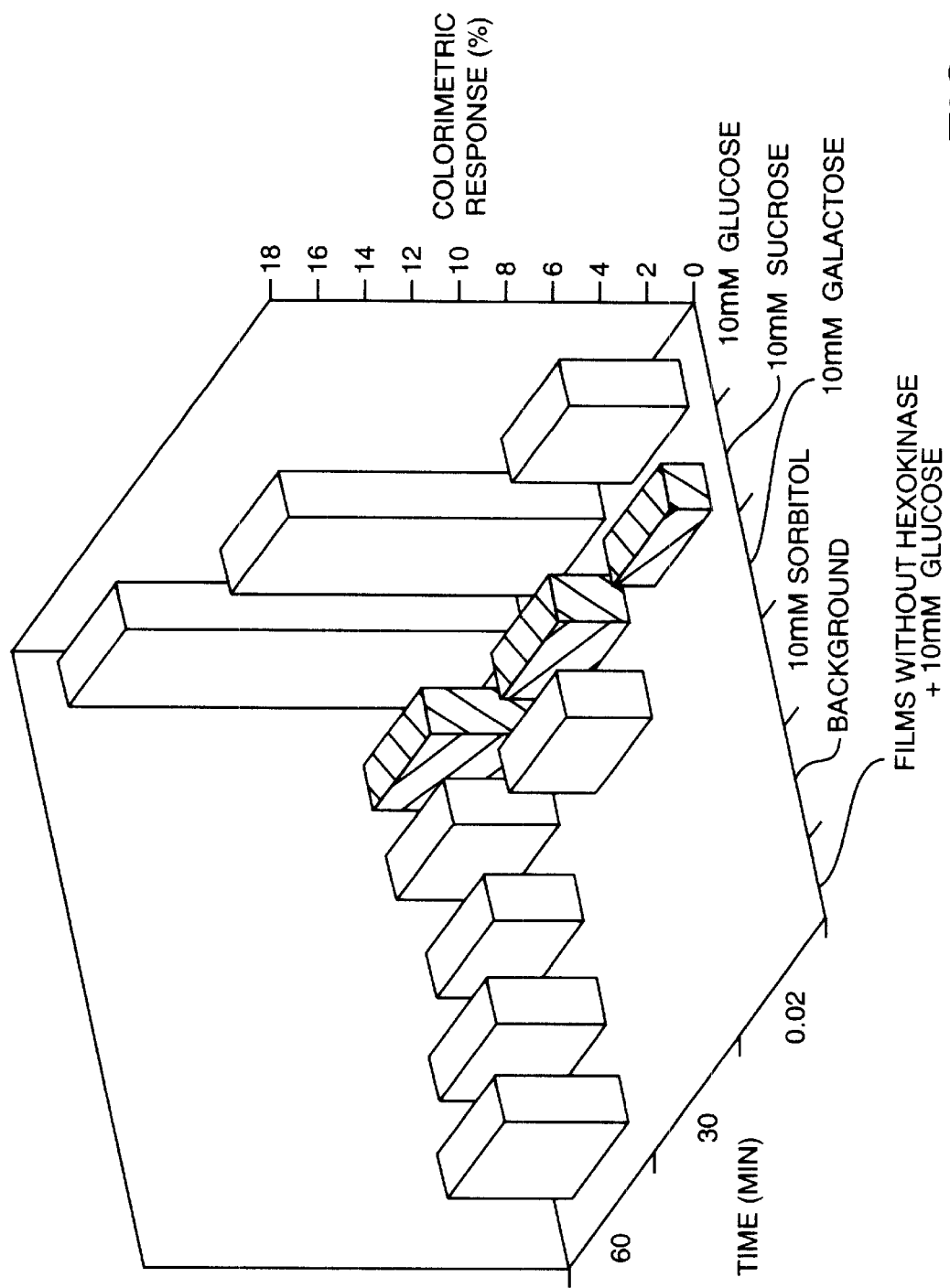
FIG. 36 shows the colorimetric response of hexokinase containing biopolymeric material to a variety of sugars.

The selectivity of the glucose sensor was studied using sugar compounds structurally similar to glucose as shown in FIG. 36. All tests were made in 0.1 M phosphate buffer (pH 6.5). The second to the last column on the right represents the glucose agitation on the PDA monolayers without immobilized hexokinase. The sampling number (n) for the glucose is n=6, while for the rest n=3. Addition of 10.0 mM sorbitol, galactose, and sucrose did not trigger the sensor, suggesting that the sensor is very specific for the sugar glucose. To further examine the mechanism of activation of the sensor, a PDA monolayer without immobilized hexokinase was tested. No significant response was observed, as the CR at t=60 minutes was comparable to the background of the hexokinase-conjugated PDA monolayer. The result demonstrated that glucose by itself cannot induce the color change in the PDA films. The presence of immobilized hexokinase was required to allow the sensor to respond to glucose.

VIII. Other Examples

The examples provided above demonstrate the broad range of analytes detectable by the presently claimed invention, ranging from complex biological organisms (e.g., viruses, bacteria, and parasites) to simple, small organic molecules (e.g., alcohols). A number of other analytes have been successfully detected using ligands linked to biopolymeric material including, but not limited to botulinum neurotoxin detected with ganglioside incorporated PDA (Pan and Charych, Langmuir 13: 1367 [1997]). It is contemplated that numerous ligand types will be linked to self-assembling monomers using standard chemical synthesis techniques known in the art to detect a broad range of analytes. Additionally, numerous other ligand types can be incorporated into the biopolymeric matrix without covalent attachment to self-assembling monomer. These materials allow for the deflection of small molecules, pathogens, bacteria, membrane receptors, membrane fragments, volatile organic compounds, enzymes, drugs, and many other relevant The presently claimed invention also finds use as a sensor in a variety of other applications. The color transition of PDA materials is affected by changes in temperature and pH. Thus, the methods and compositions of the presently claimed invention find use as temperature and pH detectors.

Ligands can also be used in the present invention when they function as competitive binders to the analyte. For example, by measuring the colorimetric response to an analyte in the presence of a natural receptor for the analyte, one can determine the quantity and/or binding affinity of the natural receptor. Application of competition or inhibition techniques allow the testing of very small, largely unreactive compounds, as well as substances present in very low concentrations or substances that have a small number or single valiancy. One application of this technique finds use as a means for the development and improvement of drugs by providing a screening assay to observe competitive inhibition of natural binding events. The compositions of the presently claimed invention further provide means for testing libraries of materials, as the binding of desired material can be colorimetrically observed and the relevant biopolymeric material with its relevant ligand separated from the others by segregating out a particular polymeric structure.

Example 8

Immobilization of Biopolymeric Material

I. Immobilization to Silicon Chips and Gels

The silicon gel or wafers are acid cleaned in 1:1 HCl/methanol, rinsed in water, and placed in concentrated sulfuric acid. After a thorough water rinse, the wafer chips or gel is boiled in doubly distilled deionized water, allowed to cool and dry and then silanized under inert atmosphere in a 2% solution of 3-mercaptopropyl trimethoxysilane prepared in dry toluene. Next, the chips or gels are placed in a 2 mM solution of either GMBS (N-succinimidyl 4-maleimidobutyrate) or EMCS (N-succinimidyl 6-maleimidocaproate) prepared in 0.1 M phosphate buffer (the cross linker is first dissolved in a minimal amount of dimethylformamide). After rinsing with phosphate buffer, the chips are placed in a 0.05 mg/ml solution of the liposomes prepared in pH 8.0 phosphate buffer. Finally, the chips or gels are thoroughly rinsed with, and then stored in, the buffer solution prior to their use. The liposomes should have an —$NH_2$ functionality for the cross-linking with GMBS or EMCS to work.

II. Sol-Gel Entrapment of Biopolymeric Material

A silica sol was prepared by sonicating 15.25 g of tetramethylorthosilicate (TMOS), 3.35 g of water, and 0.22 ml of 0.04 N aqueous hydrochloric acid in a chilled bath until the solution was one phase (approximately 20 minutes). Chilled MOPS buffer solution (50% v/v) was then added to the acidic sol making sure that the solution was well cooled in an ice bath to retard gelation. A variety of materials are appropriate for generating silica sols, including, but not limited to, any tetraalkoxysilane or organically modified silane (e.g., ormosil). Additionally, tetraethylorthosilicate (TEOS), methyltriethoxysilane (MeTEOS), aryl silsesquioxanes, and other metal oxides find use in generating sol-gel glass.

For encapsulating liposomes, a polymerized liposome solution (2.5 ml) (as generated in Example 1) was then mixed into the buffered sol (10 ml) and the mixture poured into plastic cuvettes, applied as a film on a flat surface, or poured into any other desired formation template, sealed with Parafilm, and allowed to gel at ambient temperature. Gelation of the samples occurred within a few minutes resulting in transparent, monolithic solids (18 mm×10 mm×5 mm) in the case of cuvette formed gels and as violet colored monoliths with p-PDA liposomes. Slight shrinkage of aged monoliths was observed due to syneresis.

The encapsulation of other biopolymeric material shapes (i.e., film and other nanostructures) can be conducted as described above. The materials must be generated or sectioned into small (i.e., nanoscopic) sized portions if not already so, and incorporated into a solution to be mixed with the buffered sol.

Example 9

Generation of Arrays

In some embodiments, the presently claimed invention contemplates the generation of a large palette of polymerizable lipids of different headgroup chemistries to create an array. Lipids containing head groups with carboxylic acid functionalities (imparting a formal negative charge), hydrophilic uncharged hydroxy groups, primary amine functionalities (that may acquire a formal positive charge), amino derivatives (with positive, negative or zwitterionic charge), and hydrophobic groups among others can be generated. In some embodiments of the present invention, the combination of these materials into a single device facilitates the simultaneous detection of a variety of analytes or the discrimination of a desired analytes from background interferants. In some embodiments, biopolymeric materials comprising varying dopant materials are used to provide a different color pattern for each portion of the array.

Figure 37:
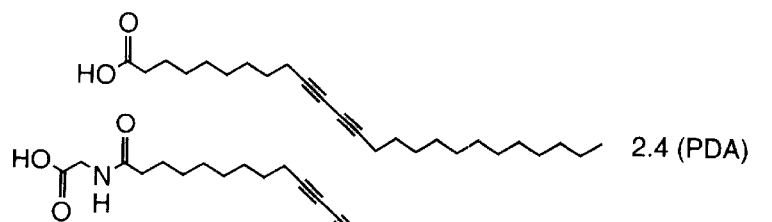
FIG. 37 shows derivations of PDA for use in detection arrays.
Figure 37:
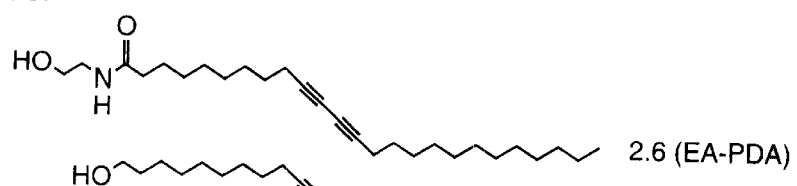
Figure 37:
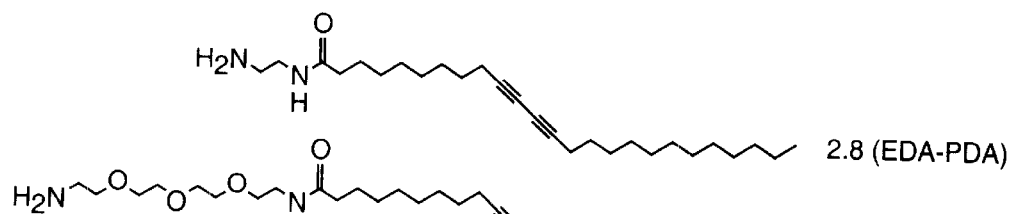
Figure 37:
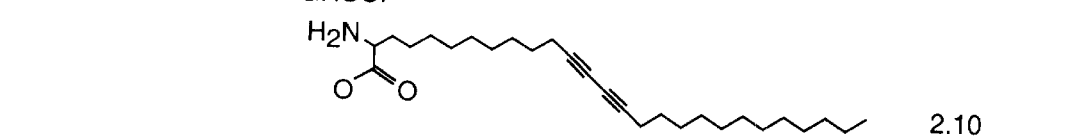
Figure 37:
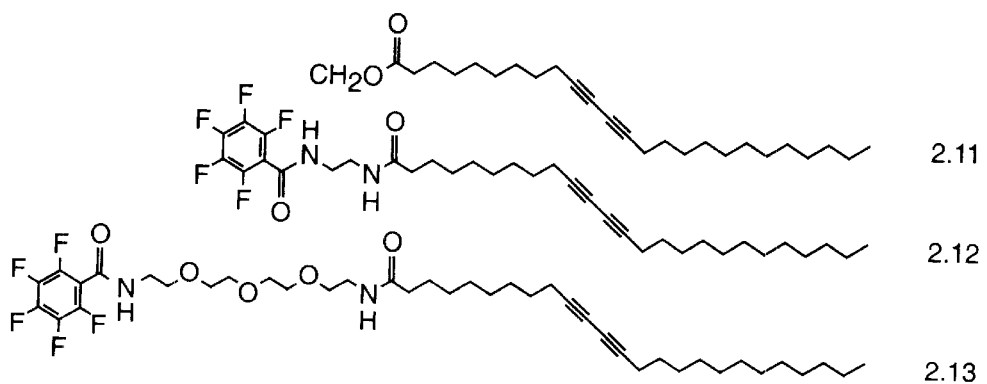

For example, a large palette of polymerizable lipids of different headgroup chemistries can be generated to create an array. For example, FIG. 37 depicts lipids with various head group chemistries. These may be categorized into five groups based upon their head group functionality. Compounds 2.4 and 2.5 contain carboxylic acid functionalities, imparting a formal negative charge. Compounds 2.6 and 2.7 contain a hydrophilic uncharged hydroxyl group. Compounds 2.8 and 2.9 have primary amine functionalities that may acquire a formal positive charge. The amino acid derivative 2.10 may exist with positive, negative or zwitterionic charge. Compounds 2.11–2.13 have hydrophobic head groups.

Figure 38:
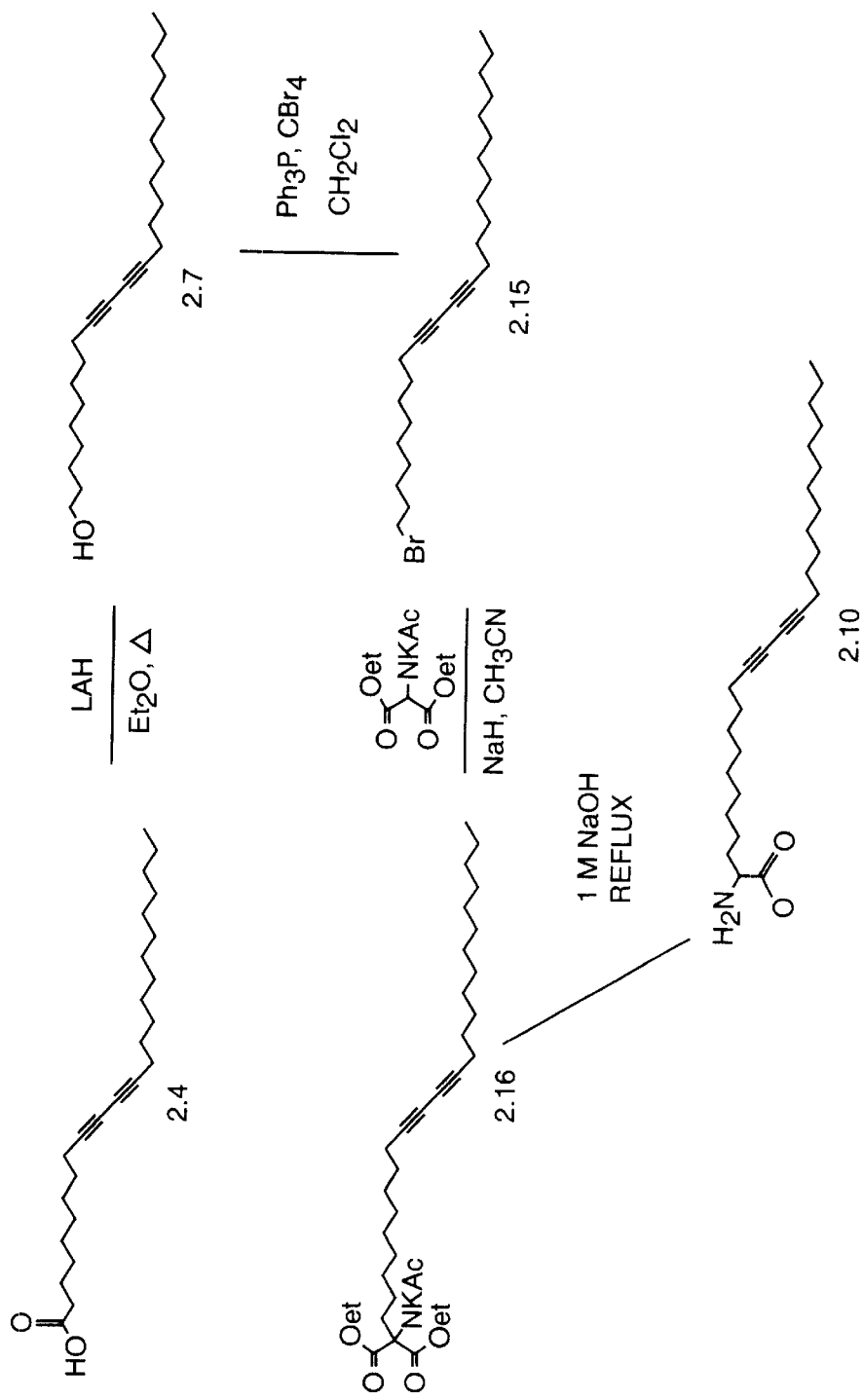
FIG. 38 shows the organic synthesis of compound 2.10 from FIG. 37.

The synthesis of these lipids begins with commercially available PDA (2.4). Synthesis of all but 2.10, 2.12, and 2.13 can be carried out by coupling the respective head group to PDA utilizing the activated N-hyroxysuccinimidyl ester of PDA (NHS-PDA) as described above. The amino acid lipid 2.10 can be prepared in four steps from PDA as shown in FIG. 38, using lithium aluminum hydride and transformation of the alcohol to the corresponding bromide derivative. The bromide is converted to the protected amino acid by reaction with diethyl N-acetimidomalonate in acetonitrile with sodium hydride, followed by deprotection. The fluorinated lipids 2.12 and 2.13 can be prepared by the reaction of pentafluorobenzoyl chloride with amino lipids 2.8 and 2.9.

Materials prepared as above, can be deposited into chambers of a device or immobilized to specific portions of a device. By generating biopolymeric materials with different properties (e.g., analyte or reaction detection capabilities, colors, analytes affinities) within a single apparatus (e.g., a badge), an array is generated with the ability to identify, distinguish, and quantitate a broad range of reactions and analytes.

Example 10

Detection of Membrane Rearrangements

I. Phospholipase $A_2$

Biopolymeric liposomes were prepared by probe sonication of a mixture of polymerizable matrix lipid 10,12-tricosadiynoic acid and various mole fractions (0%–40%) of $PLA_2$ substrate lipid (e.g., DMPC) in water, followed by polymerization with 1.6 $\mu J/cm^2$ ultraviolet radiation, 254 nm. Analysis by transmission electron microscopy indicated an average vesicle size of approximately 100 nm.

In their initial state, the vesicles appeared deep blue to the naked eye and absorb maximally at around 620 nm. Polymerized vesicles composed of 40% DMPC/60% PDA, 1 mM total lipid, were diluted 1:10 in 50 mM Tris buffer pH 7.0 to a final volume of 0.5 ml in a standard cuvette and the spectrum recorded using a Hewlett Packard Spectrophotometer Model 9153C. Bee venom phospholipase A$_2$ (Sigma) was dissolved in a 10 mM Tris, 150 mM NaCl, 5 mM CaCl$_2$ buffer pH 8.9 to yield a final concentration of 1.4 mg/ml PLA$_2$. 50 μl of this solution was added to the cuvette and the spectrum was recorded after 60 minutes. Upon addition of PLA$_2$ to the DMPC/PDA vesicles, the suspension rapidly turned red (i.e., within minutes) and exhibited a maximum absorption at approximately 540 nm as shown in FIG. 13, described above.

Figure 17:
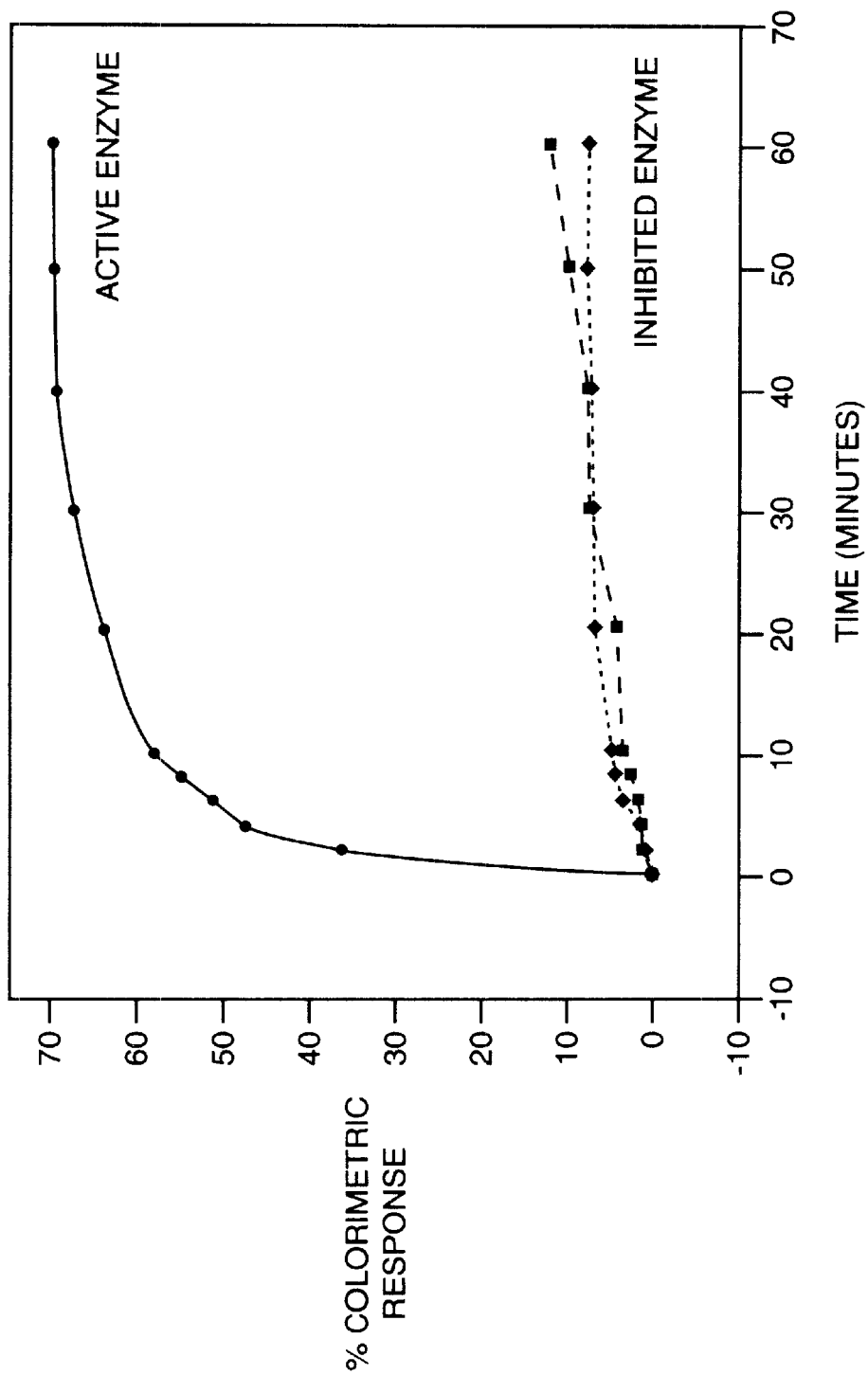
FIG. 17 shows the colorimetric response of DMPC containing liposomes in the presence of PLA$_2$ (circles), and PLA$_2$ with inhibitors (squares and diamonds).

Liposomes containing a range of mole % DMPC were tested for their ability to produce a colorimetric response. Five microliters of 1.4 mg/ml PLA$_2$ was added to 50 μl of DMPC/PDA vesicles (0.1 mM final total lipid concentration). The experiment was carried out in a standard 96-well plate using a Molecular Devices UV Max kinetic microplate reader. The absorption of the vesicle solution was monitored as a function of time at 620 nm and 490 nm wavelengths. The data was then plotted as colorimetric response (CR) versus time to yield the color response curves as shown in FIG. 17, described above.

In order to confirm that biocatalysis was occurring at the DMPC/PDA vesicles, PLA$_2$ activity was independently measured using a labeled lipid analog incorporated into the PDA matrix, allowing simultaneous measurement of product formation and calorimetric response of the vesicles. The analog used was thioester 1,2-bis-(S-decanoyl)-1,2-dithio-sn-glycero-3-phosphocholine (DTPC). Five microliters of 40% DTPC/PDA vesicles diluted with 45 μl 40 mM Tris pH 7.0 and 5 μl of 6 mM DTNB were incubated with 10 μl of 1.4 mg/ml PLA$_2$. The absorbance at 412 nm was monitored over time.

NMR experiments were conducted to further verify the occurrence of interfacial catalysis by PLA$_2$, and provide information of the fate of the enzymatic reaction products. The spectra were taken at a magnetic field of 11.7 Tesla on a Bruker DMX500 NMR spectrometer. The Block-decay pulse sequence was used with 2048 acquisition data points. 40 000 free induction decays were accumulated in each experiment with 2 second recycle delays. 0.1 M phosphoric acid was used as an external reference. FIG. 16 shows the $^{31}$P NMR spectra of A) Mixed DMPC/PDA vesicles, 0.1 mM total lipid; B) the same vesicle suspension after addition of PLA$_2$ (200 ng).

II. Phospholipase C and D

The assays for phospholipase D and C were run under similar conditions as the phospholipase PLA$_2$ assays. In all assays, 1 mM 40% DMPC/60% 10,12-tricosadiynoic acid (TRCDA) liposomes were used. Aqueous stock solutions of phospholipase D and C were prepared by dissolving the enzymes at 1 mg/ml concentration in 50 mM Tris, 150 mM NaCl, 5 mM CaCl$_2$ PH 8.9 buffer and 20 mM sodium borate, 150 mM NaCl, 5 mM CaCl$_2$ pH 8.9 buffer, respectively. The assays were then performed by adding 5 μl of liposomes, 45 μl 50 mM Tris pH 7.0 (or 20 mM sodium borate pH 7.0 when testing PLC), and 5 μl of enzyme. Controls for the assays consisted of 5 μl of buffer instead of enzyme. The assays were monitored at 620 nm and 490 nm every two minutes for the first ten minutes, and then every ten minutes for the remaining 50 minutes.

III. Bungarotoxin

Assays were conducted under similar conditions to the experiments described above. Ten microliters of 1 mM 40% DMPC/60% TRCDA liposomes, 35 μl of 50 mM Tris pH 7.4, 15 μl BUTX (Molecular Probes B-3459) were dissolved in 50 mM Tris, 150 mM NaCl, 5 mM CaCl$_2$ pH 7.4 to make a 2 mg/ml solution. Spectra were monitored every 2 minutes for the first 10 minutes of the incubation and every 10 minutes for the remaining 50 minutes. Absorbance at 490 and 620 nm were monitored using a UV max microplate reader.

IV. Inhibitor Screening

Inhibitors were used to block the calorimetric event initiated by PLA$_2$. DMPC/PDA vesicles containing 0.6% MJ33 were polymerized and incubated with 5 μl of 1.4 mg/ml PLA$_2$. Five microliters of unpolymerized liposomes were combined with 40 μl of 50 mM Tris pH 7.0, 5 μl MJ33 (0.006 M dissolved in water), 5 μl of 50 mM Tris, 150 mM NaCl, 5 mM CaCl$_2$ pH 8.9, and incubated for 15 minutes. The liposomes were then polymerized in 96 well plates and absorption spectrum were recorded at 490 nm and 620 nm. Five microliters of PLA$_2$ were added and spectra at specific time intervals were monitored for one hour. For Zn$^{2+}$ inhibition, the enzyme was dissolved in 10 mM Tris, 150 mM NaCl, 0.1 mM ZnCl$_2$ pH 8.9.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A method for detecting an enzymatic reaction, comprising:

a) providing:
      i) a biopolymeric material comprising an enzyme substrate and a plurality of polymerized self-assembling monomers, and
      ii) an enzyme that enzymatically modifies said enzyme substrate such that said enzymatic modification of said enzyme substrate causes a conformational change in said biopolymeric material;

b) exposing said enzyme said biopolymeric material comprising said enzyme substrate such that said conformational change in said biopolymeric material is produced resulting in a color change of said biopolymeric material; and c) detecting said color change in said biopolymeric material, wherein said color change indicates at least a partial occurrence of said enzymatic reaction.

2. The method of Claim 1, further comprising the step of quantifying said color change in said biopolymeric material.

3. The method of claim 1, wherein said biopolymeric material is selected from the group consisting of liposomes, films, and tubules.

4. The method of claim 1, wherein said self-assembling monomers comprise diacetylene monomers.

5. The method of claim 1, wherein said self-assembling monomers comprise diacetylene monomers selected from the group consisting of 5,7-docosadiynoic acid, 5,7-pentacosadiynoic acid, and 10,12-pentacosadiynoic acid.

6. The method of claim 1, wherein said self-assembling monomers are selected from the group consisting of acetylenes, alkenes, thiophenes, polythiophenes, siloxanes, poly-silanes, anilines, pyrroles, polyacetylenes, poly (para-phylenevinylene), poly (para-phylene), and vinylpyridinium.

7. The method of claim 1, wherein said biopolymeric material further comprises one or more ligands.

8. The method of claim 7, wherein said one or more ligands is selected from the group consisting of proteins, antibodies, carbohydrates, nucleic acids, lipids and glycolipids.

9. The method of claim 7, wherein said one or more ligands have affinity for said enzyme.

10. The method of claim 1, wherein said biopolymeric material further comprises one or more dopants.

11. The method of claim 10, wherein said one or more dopants is a diacetylene derivative selected from the group consisting of sialic acid-derived diacetylene, lactose-derived diacetylene and amino acid-derived diacetylene.

12. The method of claim 1, wherein said biopolymeric material further comprises a support, and wherein said biopolymeric material is immobilized to said support.

13. The method of claim 12, wherein said support is selected from the group consisting of polystyrene, polyethylene, teflon, mica, sephadex, sepharose, polyacrynitriles, filters, glass, gold, silicon chips, and silica.

14. The method of claim 1, wherein said enzyme substrate comprises a lipid.

15. The method of claim 1, wherein said enzyme is a lipase.

16. The method of claim 15, wherein said lipase is selected from the group consisting of phospholipase $A_2$, phospholipase C, and phospholipase D.

* * * * *